(12) United States Patent
Donde et al.

(10) Patent No.: US 9,546,162 B2
(45) Date of Patent: Jan. 17, 2017

(54) COMPOUNDS AND METHODS FOR SKIN REPAIR

(71) Applicant: Allergan, Inc., Irvine, CA (US)

(72) Inventors: Yariv Donde, Dana Point, CA (US); Jeremiah H. Nguyen, La Puente, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/498,380

(22) Filed: Sep. 26, 2014

(65) Prior Publication Data

US 2015/0094330 A1    Apr. 2, 2015

Related U.S. Application Data

(60) Provisional application No. 61/883,637, filed on Sep. 27, 2013, provisional application No. 62/024,218, filed on Jul. 14, 2014.

(51) Int. Cl.

| | | |
|---|---|---|
| *C07D 209/08* | (2006.01) | |
| *C07D 209/12* | (2006.01) | |
| *C07D 215/06* | (2006.01) | |
| *C07D 231/56* | (2006.01) | |
| *C07D 405/06* | (2006.01) | |
| *C07D 409/06* | (2006.01) | |
| *C07C 65/26* | (2006.01) | |
| *A61K 31/404* | (2006.01) | |
| *A61K 31/405* | (2006.01) | |
| *A61K 31/416* | (2006.01) | |
| *A61K 31/47* | (2006.01) | |
| *A61K 31/498* | (2006.01) | |
| *A61K 31/192* | (2006.01) | |
| *C07D 215/48* | (2006.01) | |
| *C07D 209/18* | (2006.01) | |
| *C07D 209/22* | (2006.01) | |
| *C07D 209/26* | (2006.01) | |
| *C07D 209/44* | (2006.01) | |
| *C07C 65/28* | (2006.01) | |

(52) U.S. Cl.
CPC ............ *C07D 409/06* (2013.01); *C07C 65/26* (2013.01); *C07C 65/28* (2013.01); *C07D 209/08* (2013.01); *C07D 209/12* (2013.01); *C07D 209/18* (2013.01); *C07D 209/22* (2013.01); *C07D 209/26* (2013.01); *C07D 209/44* (2013.01); *C07D 215/06* (2013.01); *C07D 215/48* (2013.01); *C07D 405/06* (2013.01)

(58) Field of Classification Search
CPC ... C07D 209/42; C07D 209/08; C07D 209/12; C07D 209/14; C07C 251/72
USPC ................................. 548/492, 454; 514/311
See application file for complete search history.

(56) References Cited

FOREIGN PATENT DOCUMENTS

| | | |
|---|---|---|
| EP | 2172447 | 7/2010 |
| WO | 2007-121578 | 11/2007 |
| WO | 2010-121382 | 10/2010 |
| WO | 2011-019634 | 2/2011 |

OTHER PUBLICATIONS

Liu, X., and C. Che "Highly Efficient and Regioselective Platinum(II)-Catalyzed Tandem Synthesis of Multiply Substituted Indolines and Tetrahydroquinolines" Angew. Chem. Int. Ed., 2009, 48: pp. 2367-2371.*
Beak, P., et al., α-Lithioamine synthetic equivalents from dipole-stabilized carbanions: The t-BOC group as an activator for α-Lithiation of carbamates, Tetrahedron Letters 1989, 30, 1197-1200.
Molander, G., et al., Suzuki-Miyaura Cross-Coupling Reactions of Potassium Vinyltrifluoroborate with Aryl and Heteroaryl Electrophiles, Journal of Organic Chemistry 2006, 71: 9681-9686.
Wolfe, J., et al., A Highly Active Catalyst for the Room-Temperature Amination and Suzuki Coupling of Aryl Chlorides, Angew. Chem. Int. Ed. 1999, 38: 2413-2416.
Iwao, M. et al., Directed Lithiation of 1-(tert-Butoxycarbonyl)Indolines. A Convenient Route to 7-substitued Indolines, Hetero. 1992, 34: 1031-1038 (5).
Transmittal of International Search Report & Written Opinion mailed Dec. 1, 2014 for PCT/US14/57870 filed on Sep. 26, 2014 in the name of Allergan, Inc.

* cited by examiner

*Primary Examiner* — Alicia L Otton
*Assistant Examiner* — Sagar Patel
(74) *Attorney, Agent, or Firm* — Jonathan Bass

(57) ABSTRACT

The invention provides compositions and methods for wound healing and scar reduction. The compositions and methods of the invention include at least one EP4 agonist set forth herein. Wounds and or scars that can be treated by the compositions and methods of the invention can arise from events such as surgery, trauma, disease, mechanical injury, burn, radiation, poisoning, and the like.

31 Claims, No Drawings

COMPOUNDS AND METHODS FOR SKIN REPAIR

CROSS REFERENCE TO RELATED APPLICATIONS

This application claims priority to U.S. Provisional Patent Application No. 61/883,637, filed Sep. 27, 2013 and U.S. Provisional Patent Application No. 62/024,218, filed Jul. 14, 2014, the disclosures of each of which is hereby incorporated by reference in its entirety.

FIELD OF THE INVENTION

The invention relates generally to compositions and methods for wound healing, and particularly to the use of EP4 agonists for treatment in wound healing, scar reduction, and skin repair.

BACKGROUND OF THE INVENTION

Prostanoid EP4 receptor is a G protein-coupled receptor that mediates the actions of prostaglandin E2 (PGE2) and is characterized by the longest intracellular C terminus loop when compared to other prostanoid receptors. Mainly, EP4 receptors couple to Gs and mediate elevations in cAMP concentration, although they do participate in other pathways as well. There are some redundancies in function between EP2 and EP4 receptors. For example, both receptors induce PGE2-mediated RANKL through cAMP. However, EP2 is involved in cumulus expansion in ovulation and fertilization, whereas EP4 regulates closure of the ductus arteriosus. Expression of EP4 receptors is controlled by various physiological and pathophysiological processes as these receptors participate in ovulation and fertilization, induce bone formation, protect against inflammatory bowel disease, facilitate Langerhans cell migration and maturation and mediate joint inflammation in a model of collagen-induced arthritis, among others Skin blemishes such as flesh wounds, scars and wrinkles can occur on any area of the body. Scarring may occur in all parts of adult body, following local or systemic traumas such as mechanical injury, surgery, burn, radiation and poisoning, and represents a failure of homeostatic processes to restore normal structure at the wound sites. Wrinkles occur for a variety of reasons and are a common sign of aging. Both scars and signs of aging can typically considered undesirable.

Accordingly, an agent that safely and effectively treats or prevents such skin blemishes is highly desirable.

SUMMARY OF THE INVENTION

The invention provides compositions and methods for wound healing and scar reduction. The compositions and methods of the invention include at least one EP4 agonist set forth herein. Wounds and or scars that can be treated by the compositions and methods of the invention can arise from events such as surgery, trauma, disease, mechanical injury, burn, radiation, poisoning, and the like.

In one embodiment of the invention, there are provided compounds having the structure:

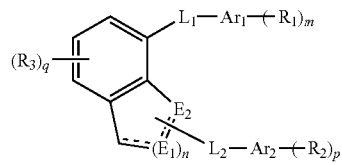

wherein:
the dashed lines represents optional bonds, provided that only one optional bond to $E_1$ is present;
$E_1$ and $E_2$ are each independently C or N;
$L_1$ is a bond, $C_1$-$C_4$ alkylene, $C_2$-$C_4$ alkenylene, or $C_2$-$C_4$ alkynylene;
$L_2$ is a bond, $C_1$-$C_4$ alkylene,

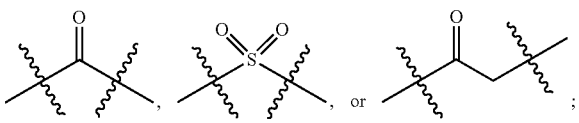

$Ar_1$ and $Ar_2$ are each independently aryl or heteroaryl;
$R_1$, $R_2$ and $R_3$ are each independently —$CO_2H$, halogen, —$CF_3$, alkoxy, benzyloxy, $C_1$-$C_4$ alkyl, —OH, —$OCH_2CO_2H$, —CH=$CHCO_2H$ or $NR_aR_b$, wherein $R_a$ and $R_b$ are each independently H or lower alkyl;
n is 1 or 2;
m and p are each independently 1 to 5; and
q is 0 to 3.

In another embodiment of the invention, there are provided compounds having the structure:

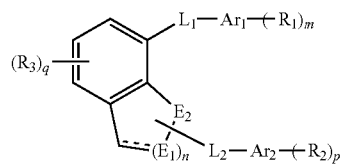

wherein:
the dashed line represents an optional bond;
$E_1$ and $E_2$ are each independently C or N;
$L_1$ is $C_1$-$C_4$ alkylene, alkenylene, or alkynylene;
$L_2$ is $C_0$-$C_4$ alkylene,

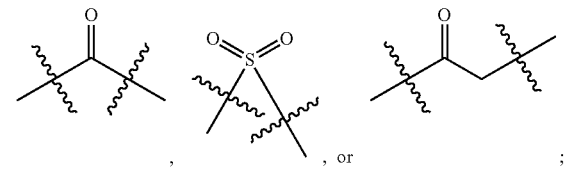

$Ar_1$ and $Ar_2$ are each independently aryl or heteroaryl;
$R_1$, $R_2$ and $R_3$ are each independently —$CO_2H$, halogen, —$CF_3$, alkoxy, benzyloxy, $C_1$-$C_4$ alkyl, —OH, or $NR_aR_b$, wherein $R_a$ and $R_b$ are each independently H or lower alkyl;
n is 1 or 2;
m and p are each independently 1 to 5; and
q is 0 to 3.

In another embodiment of the invention, there are provided pharmaceutical compositions including at least one compound of the invention in a pharmaceutically acceptable carrier therefor.

In another embodiment of the invention, there are provided methods of treating a skin blemish. Such methods can be performed for example, by administering to a subject in need thereof a therapeutically effective amount of a composition of the invention.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. As used herein, "alkyl" includes substituted alkyl groups bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —CH$_2$O$R_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. In some embodiments in which a numerical range of carbon atoms is not provided, "alkyl" refers to alkyl moieties having from 1 to about 12 carbon atoms. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atom. As used herein, "alkenyl" includes substituted alkenyl groups bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms. As used herein, "alkynyl" includes substituted alkynyl groups bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and includes cycloalkyl groups bearing one or more substituents as set forth above.

As used herein, "aryl" refers to aromatic groups having in the range of 5 up to 14 carbon atoms and includes substituted aryl groups bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms) includes substituted heteroaryl groups bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and includes heterocyclic groups bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

Disclosed herein are compositions and methods for treating skin blemishes, wound healing and scar reduction. In one embodiment of the invention, there are provided compounds of formula (I):

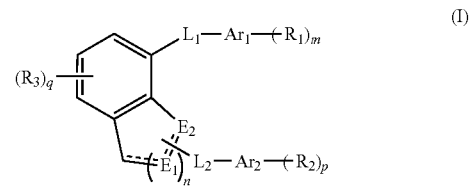

wherein:
the dashed lines represents optional bonds, provided that only one optional bond to $E_1$ is present;
$E_1$ and $E_2$ are each independently C or N;
$L_1$ is a bond, $C_1$-$C_4$ alkylene, $C_2$-$C_4$ alkenylene, or $C_2$-$C_4$ alkynylene;
$L_2$ is a bond, $C_1$-$C_4$ alkylene,

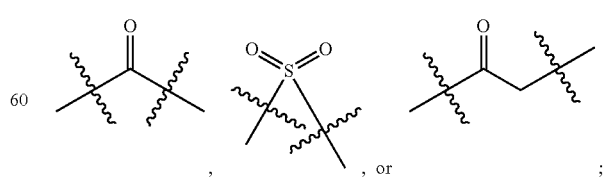

$Ar_1$ and $Ar_2$ are each independently aryl or heteroaryl;
$R_1$, $R_2$ and $R_3$ are each independently —CO$_2$H, halogen, —CF$_3$, alkoxy, benzyloxy, $C_1$-$C_4$ alkyl, —OH, —OCH$_2$CO$_2$H, —CH=CHCO$_2$H or NR$_a$R$_b$, wherein R$_a$ and R$_b$ are each independently H or lower alkyl;

n is 1 or 2;

m and p are each independently 1 to 5; and q is 0 to 3.

Also provided herein are compounds of formula (I) above, wherein L$_2$ is C$_0$-C$_4$ alkylene,

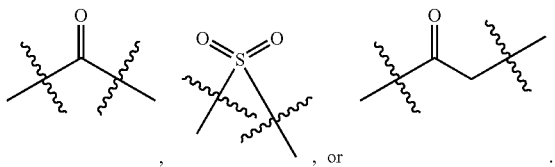

In another embodiment of the invention, there are provided compounds of formula (II):

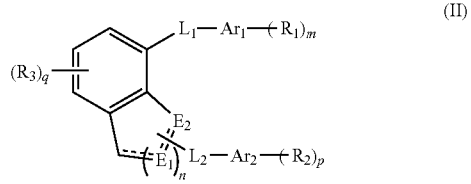

wherein:
the dashed line represents an optional bond;
E$_1$ and E$_2$ are each independently C or N;
L$_1$ is C$_1$-C$_4$ alkylene, alkenylene, or alkynylene;
L$_2$ is C$_0$-C$_4$ alkylene,

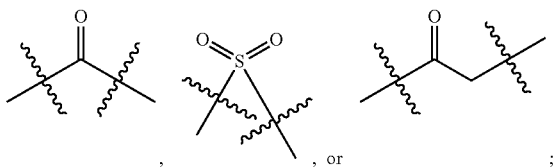

Ar$_1$ and Ar$_2$ are each independently aryl or heteroaryl;

R$_1$, R$_2$ and R$_3$ are each independently —CO$_2$H, halogen, —CF$_3$, alkoxy, benzyloxy, C$_1$-C$_4$ alkyl, —OH, or NR$_a$R$_b$, wherein R$_a$ and R$_b$ are each independently H or lower alkyl;

n is 1 or 2;

m and p are each independently 1 to 5; and q is 0 to 3.

In some embodiments, L$_1$ is C$_1$-C$_4$ alkylene, C$_2$-C$_4$ alkenylene, or C$_2$-C$_4$ alkynylene. In some embodiments, L$_1$ is C$_2$ alkylene.

In some embodiments, L$_2$ is C$_1$-C$_4$ alkylene. In other embodiments, L$_2$ is C$_1$ alkylene.

In some embodiments, Ar$_1$ is aryl, such as for example, phenyl or naphthyl.

In some embodiments, Ar$_1$ is heteroaryl, such as for example, is furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl thiophenyl, furylene, pyridinylene, oxazolylene, or thiazolene.

In some embodiments, Ar$_2$ is aryl. In other embodiments, Ar$_2$ is phenyl or naphthyl.

In some embodiments, Ar$_2$ is heteroaryl. Heteroaryl moieties contemplated for use in the practice of the invention include, but are not limited to, benzo[d][1,3]dioxole, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl thiophenyl, furylene, pyridinylene, oxazolylene, or thiazolene. In certain embodiments, Ar$_2$ is benzo[d][1,3]dioxole.

In some embodiments, m and p are each independently 1 or 2.

In some embodiments, R$_1$ is —CO$_2$H.

In some embodiments, R$_2$ is halogen. In other embodiments, R$_2$ is F.

In some embodiments, R$_2$ is alkoxy. In other embodiments, R$_2$ is methoxy.

In another embodiment of the invention, there are provided compounds of formula (III):

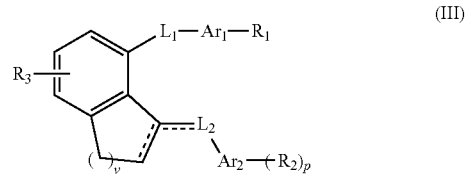

wherein:
the dashed lines represent optional bonds, provided that only one optional bond is present;

L$_1$ is a bond, C$_1$-C$_2$ alkylene, C$_2$ alkenylene, C$_2$ alkynylene, or —OCH$_2$—;

L$_2$ is CH$_2$;

Ar$_1$ and Ar$_2$ are each phenyl;

R$_1$ is —CO$_2$H, —OCH$_2$CO$_2$H or —CH=CHCO$_2$H;

each R$_2$ is independently halogen, —CF$_3$, C$_1$-C$_4$ alkyl, or C$_1$-C$_4$ alkoxy;

R$_3$ is H, halogen, or C$_1$-C$_4$ alkoxy; and p and v are each independently 1 or 2.

In one embodiment of formula (III), L$_1$ is C$_2$ alkylene, R$_1$ is —CO$_2$H, each R$_2$ is halogen, methyl or methoxy, and R$_3$ is H.

In another embodiment of formula (III), L$_1$ is C$_2$ alkylene, R$_1$ is —CO$_2$H, each R$_2$ is halogen, methyl or methoxy, R$_3$ is H, and v is 1.

In another embodiment of formula (III), L$_1$ is C$_2$ alkylene, R$_1$ is —CO$_2$H, each R$_2$ is halogen, methyl or methoxy, R$_3$ is H, p is 2, and v is 1.

In another embodiment of formula (III), L$_1$ is C$_2$ alkylene, R$_1$ is —CO$_2$H, each R$_2$ is methoxy, R$_3$ is H, and v is 1.

Exemplary compounds of the invention include, but are not limited to, compounds having the following structures:

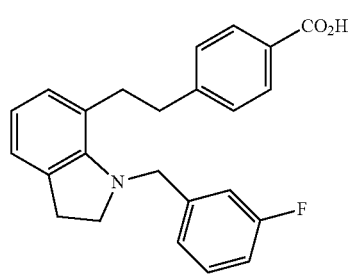 [SMILES: O=C(O)c1ccc(CCc2cccc3c2N(Cc2cccc(F)c2)CC3)cc1]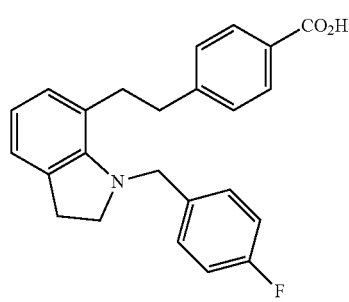 [SMILES: O=C(O)c1ccc(CCc2cccc3c2N(Cc2ccc(F)cc2)CC3)cc1]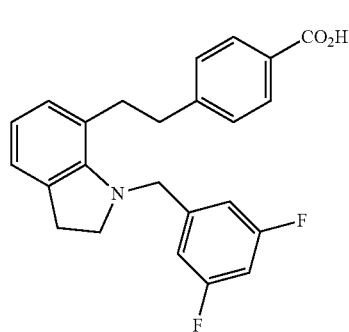 [SMILES: O=C(O)c1ccc(CCc2cccc3c2N(Cc2cc(F)cc(F)c2)CC3)cc1]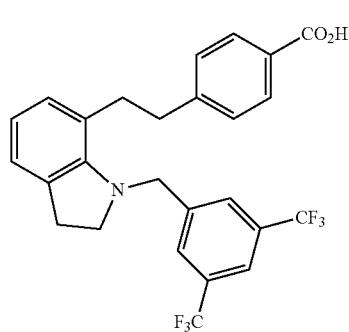 [SMILES: O=C(O)c1ccc(CCc2cccc3c2N(Cc2cc(C(F)(F)F)cc(C(F)(F)F)c2)CC3)cc1]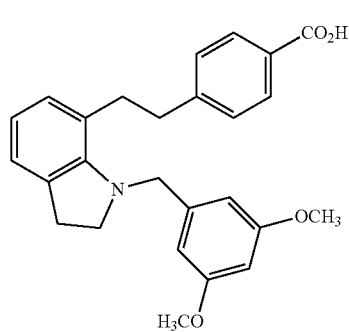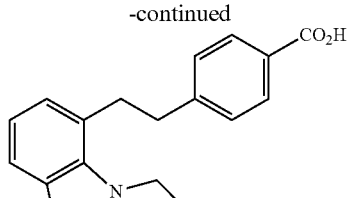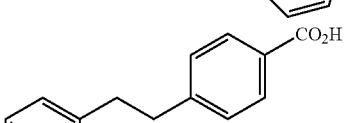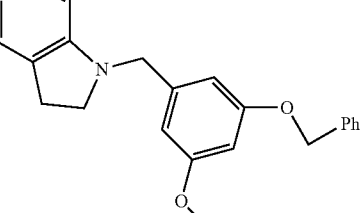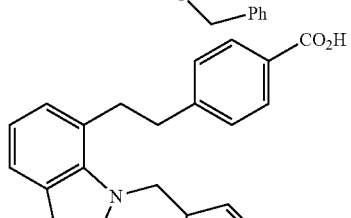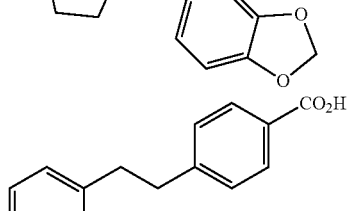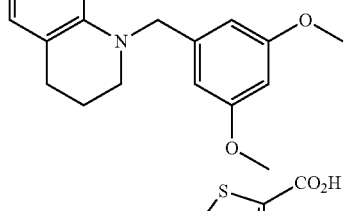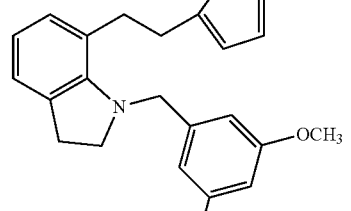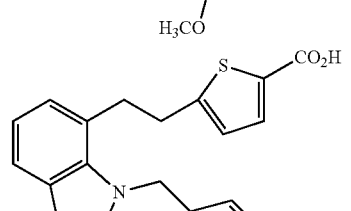

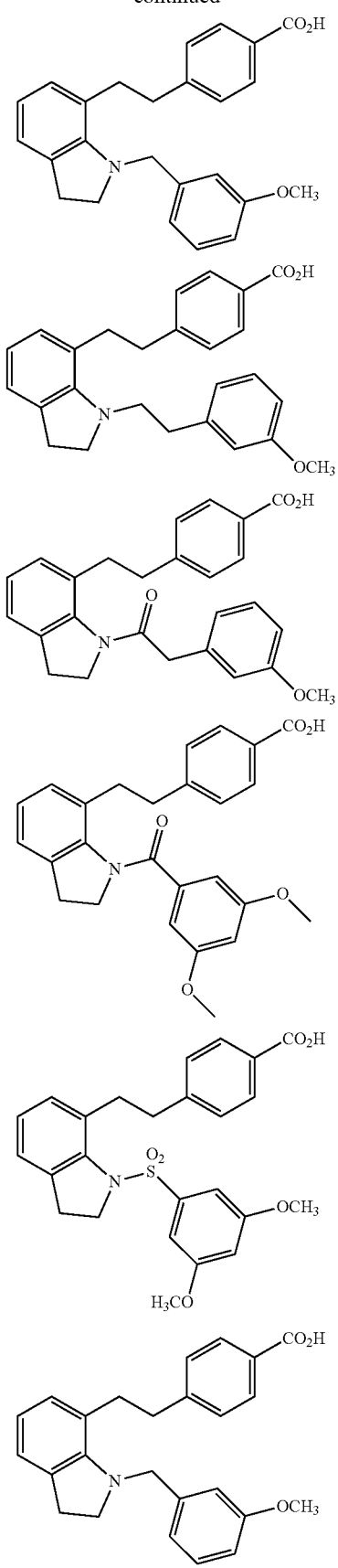
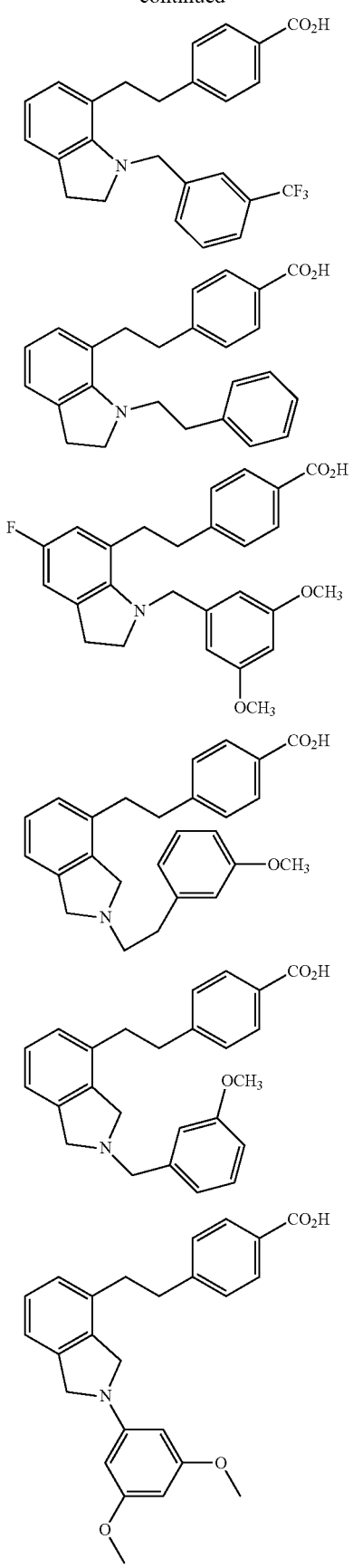

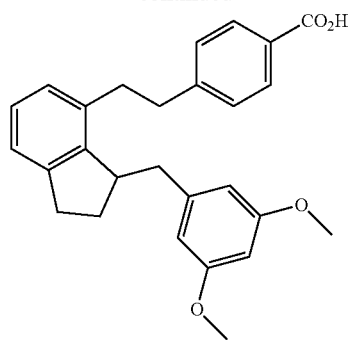
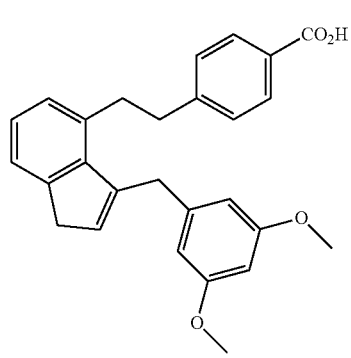
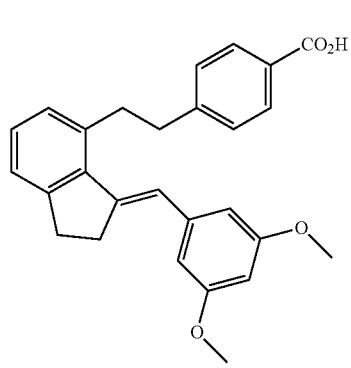
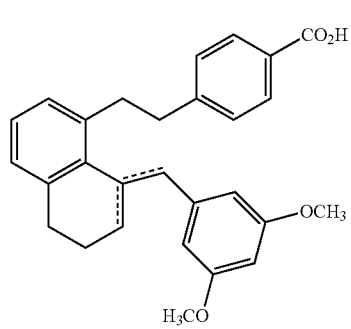
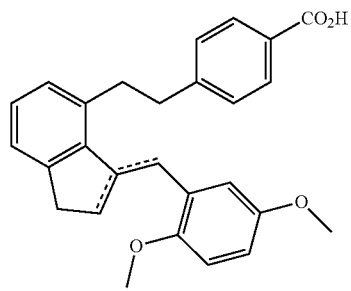
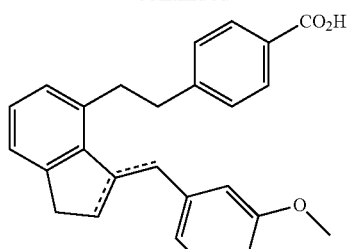
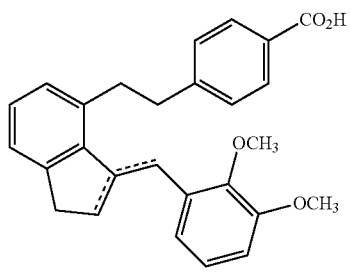
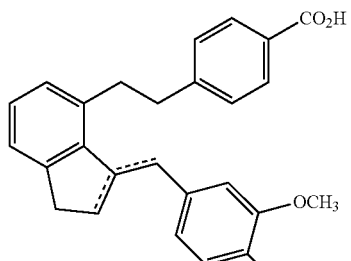
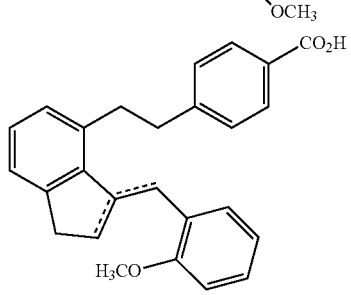
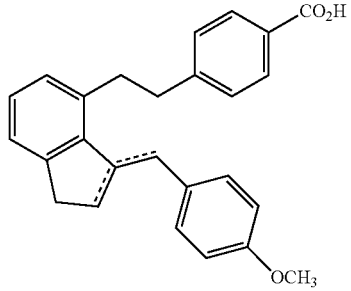
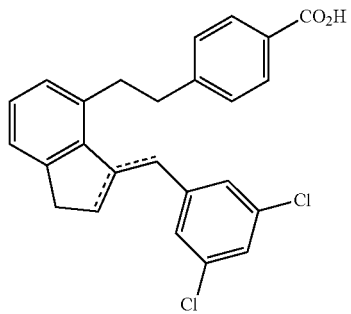

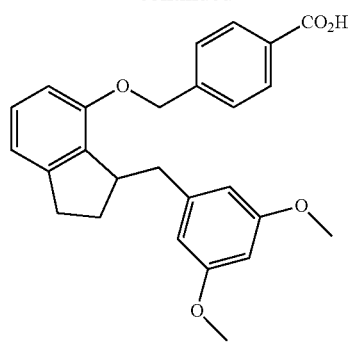
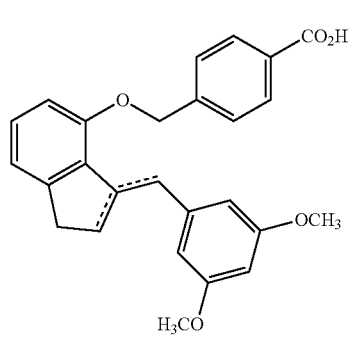
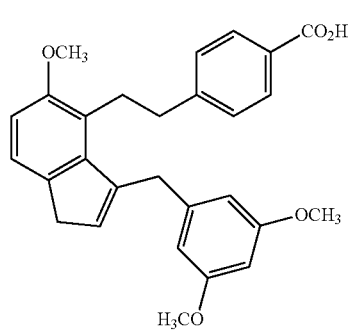
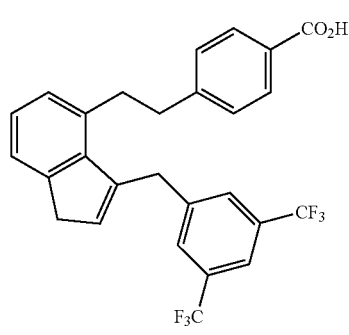
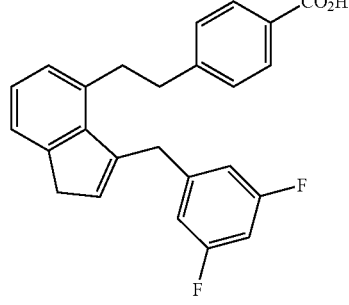
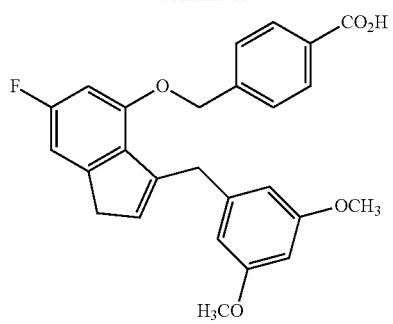
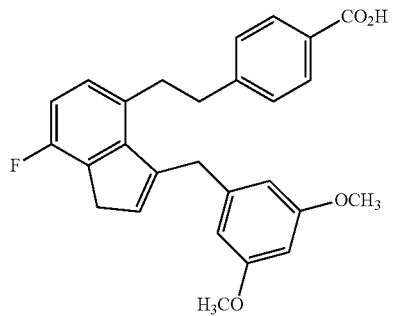
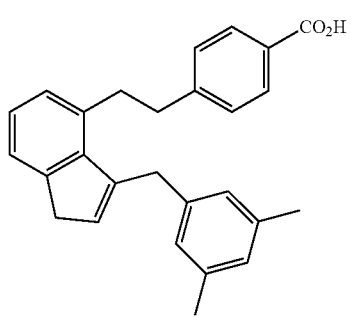
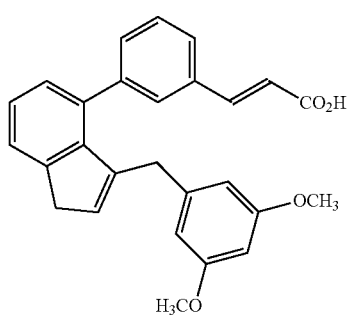
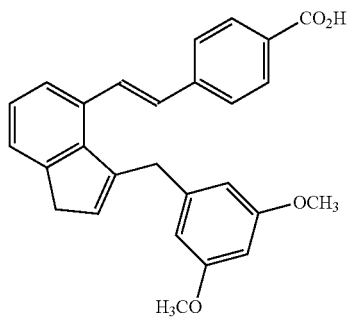

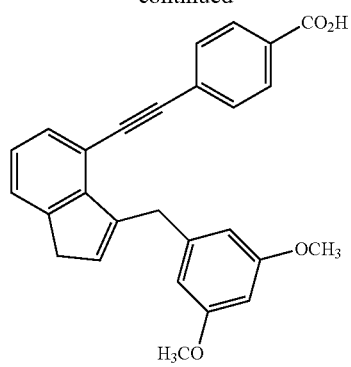
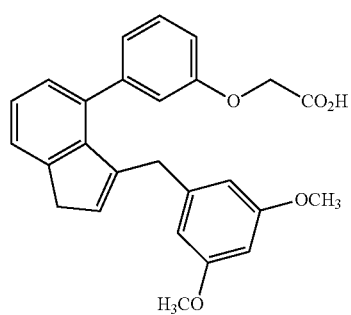
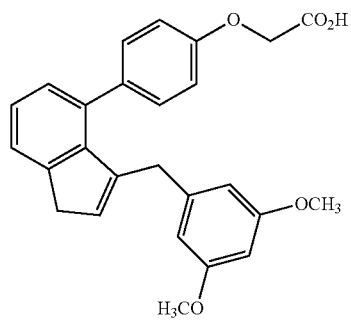
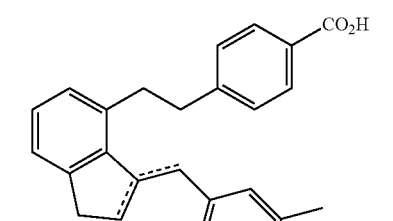
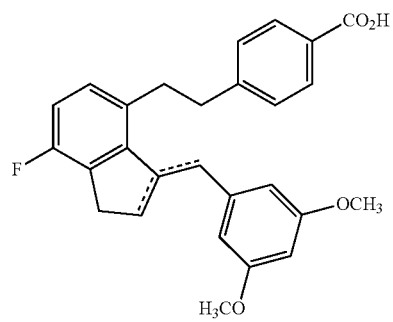
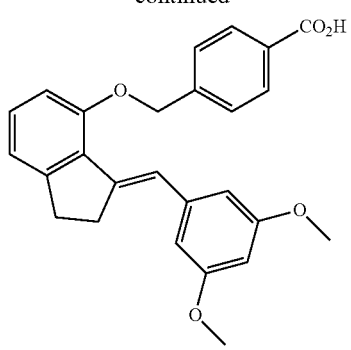
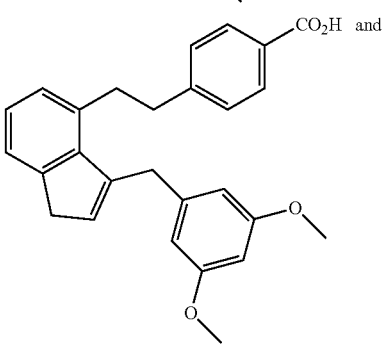
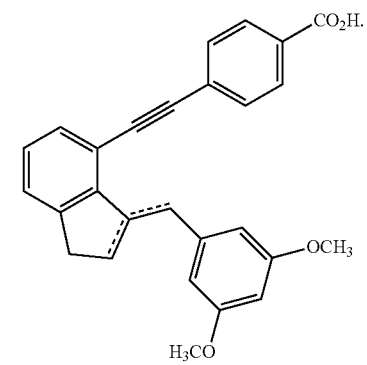
Compounds of the invention may be synthesized in a variety of ways known to those skilled in the art. Scheme 1 set forth below sets forth one synthetic route to certain compounds of the invention.
Scheme 1
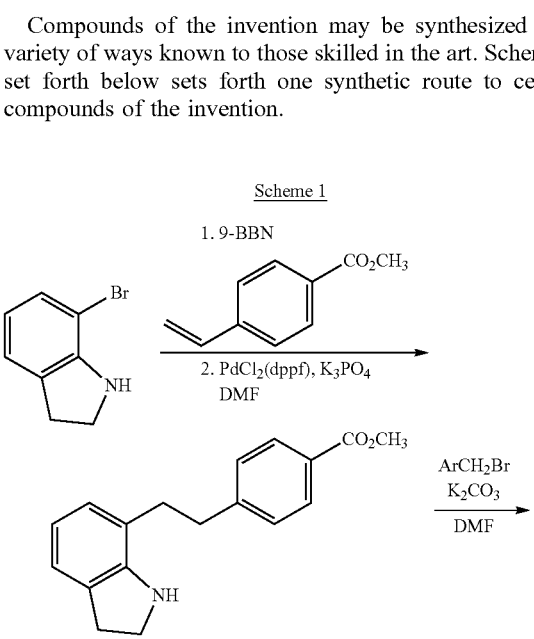

17
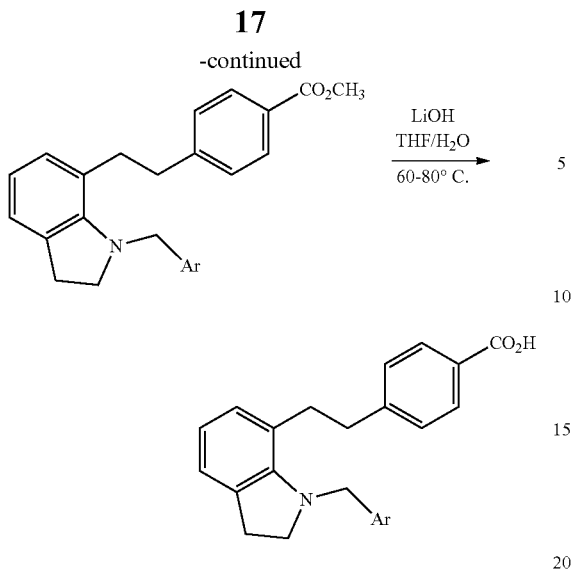
18
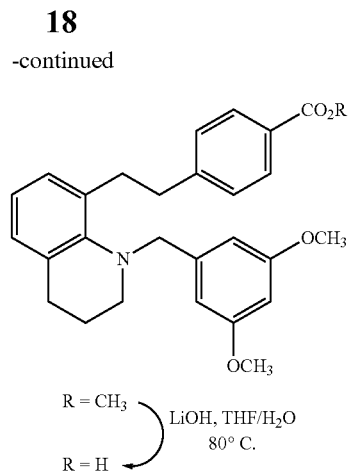
Scheme 2 set forth below sets forth a synthetic route to further compounds of the invention.
Scheme 3 set forth below sets forth a synthetic route to further compounds of the invention.
Scheme 2
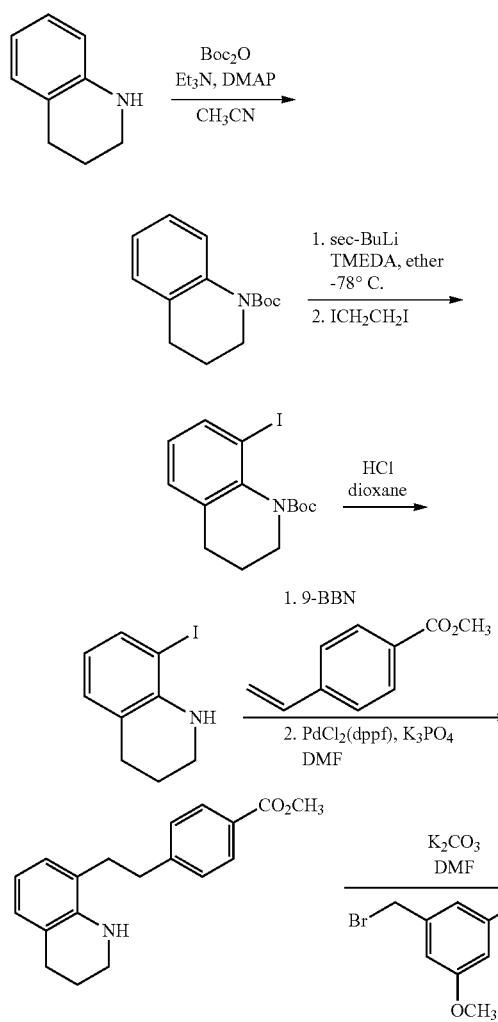
Scheme 3
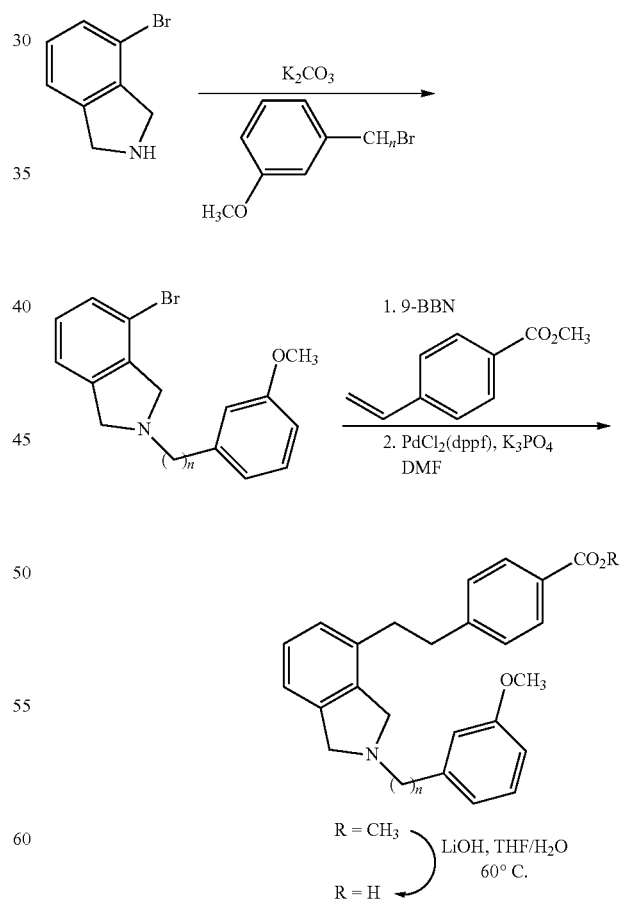
Scheme 4 set forth below sets forth a synthetic route to further compounds of the invention.

Scheme 4
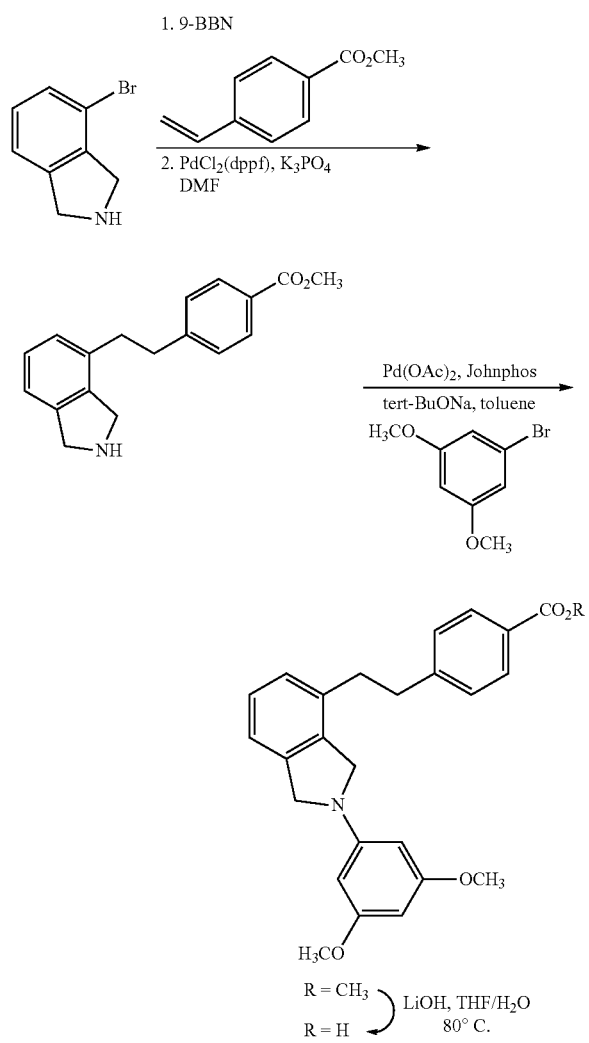
Scheme 5
Scheme 5 set forth below sets forth a synthetic route to further compounds of the invention.
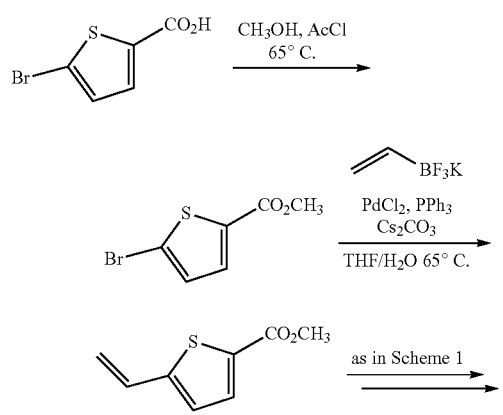
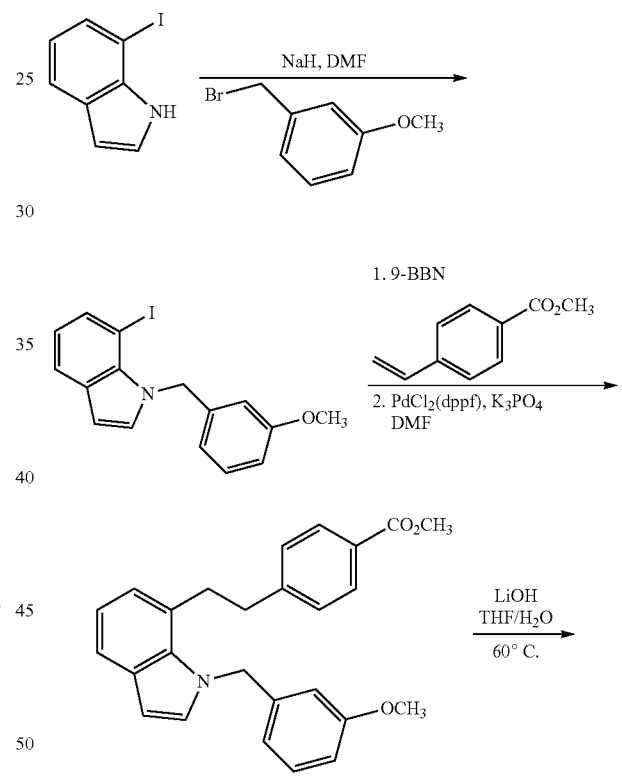
Ar = 3-methoxyphenyl, 3,5-dimethoxyphenyl
Scheme 6 set forth below sets forth a synthetic route to further compounds of the invention.
Scheme 6
Scheme 7 set forth below sets forth a synthetic route to further compounds of the invention.

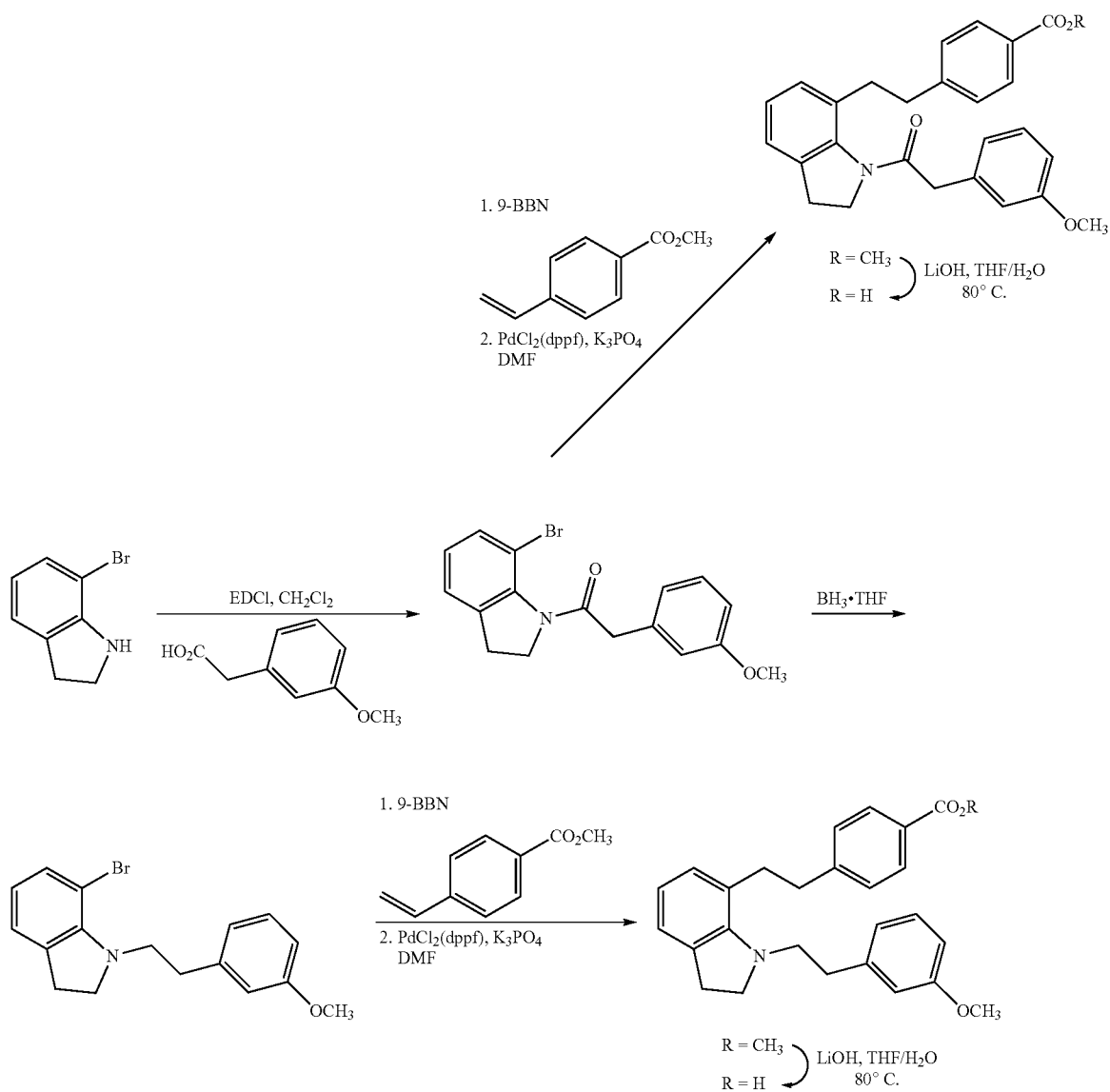
Scheme 8 set forth below sets forth a synthetic route to further compounds of the invention.
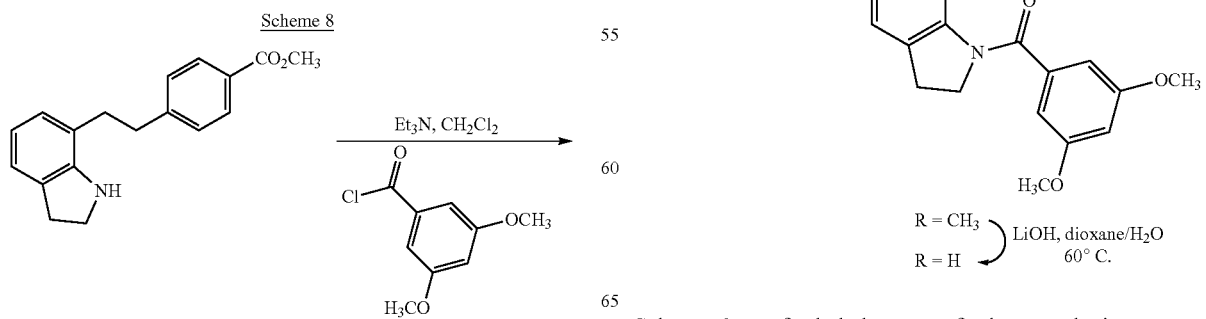
Scheme 9 set forth below sets forth a synthetic route to further compounds of the invention.

Scheme 9
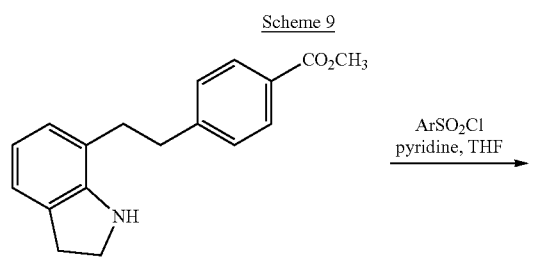
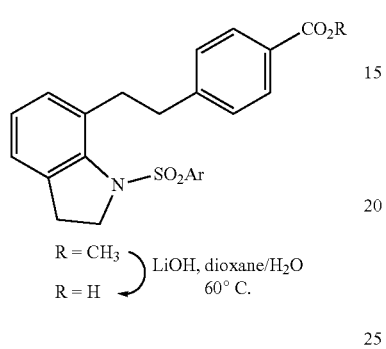
Scheme 10 set forth below sets forth a synthetic route to further compounds of the invention.
Scheme 10
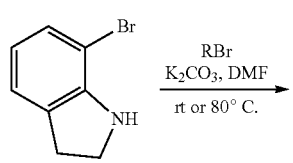
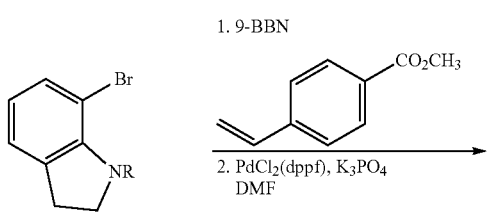
Scheme 11 set forth below sets forth a synthetic route to further compounds of the invention.
Scheme 11
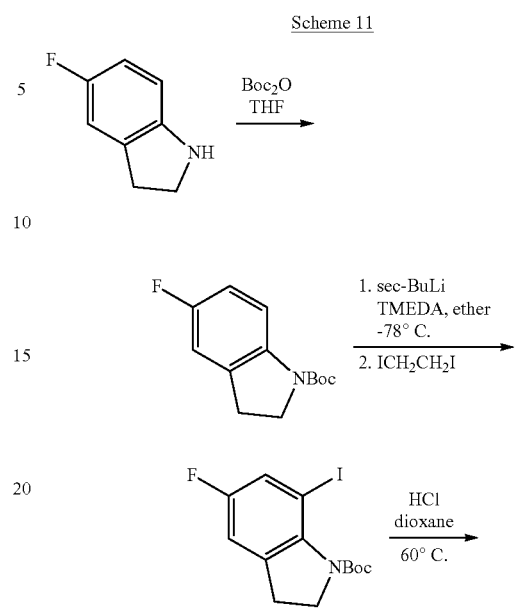
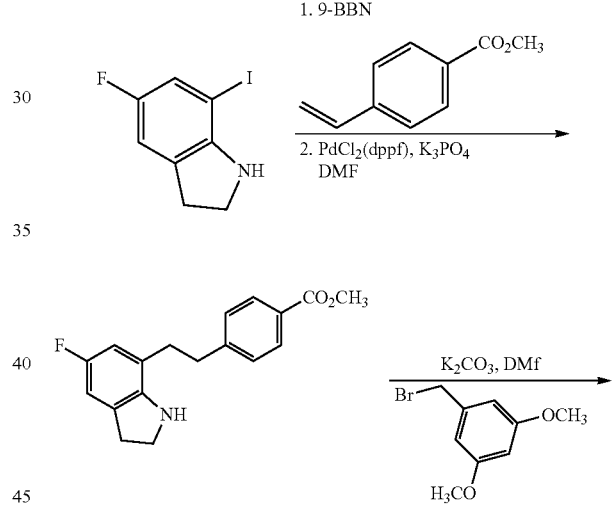
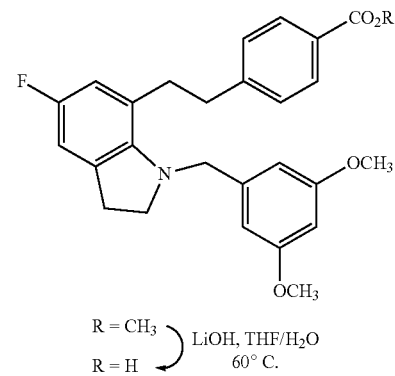
Schemes 12 to 18 below set forth synthetic routes to further compounds of the invention.

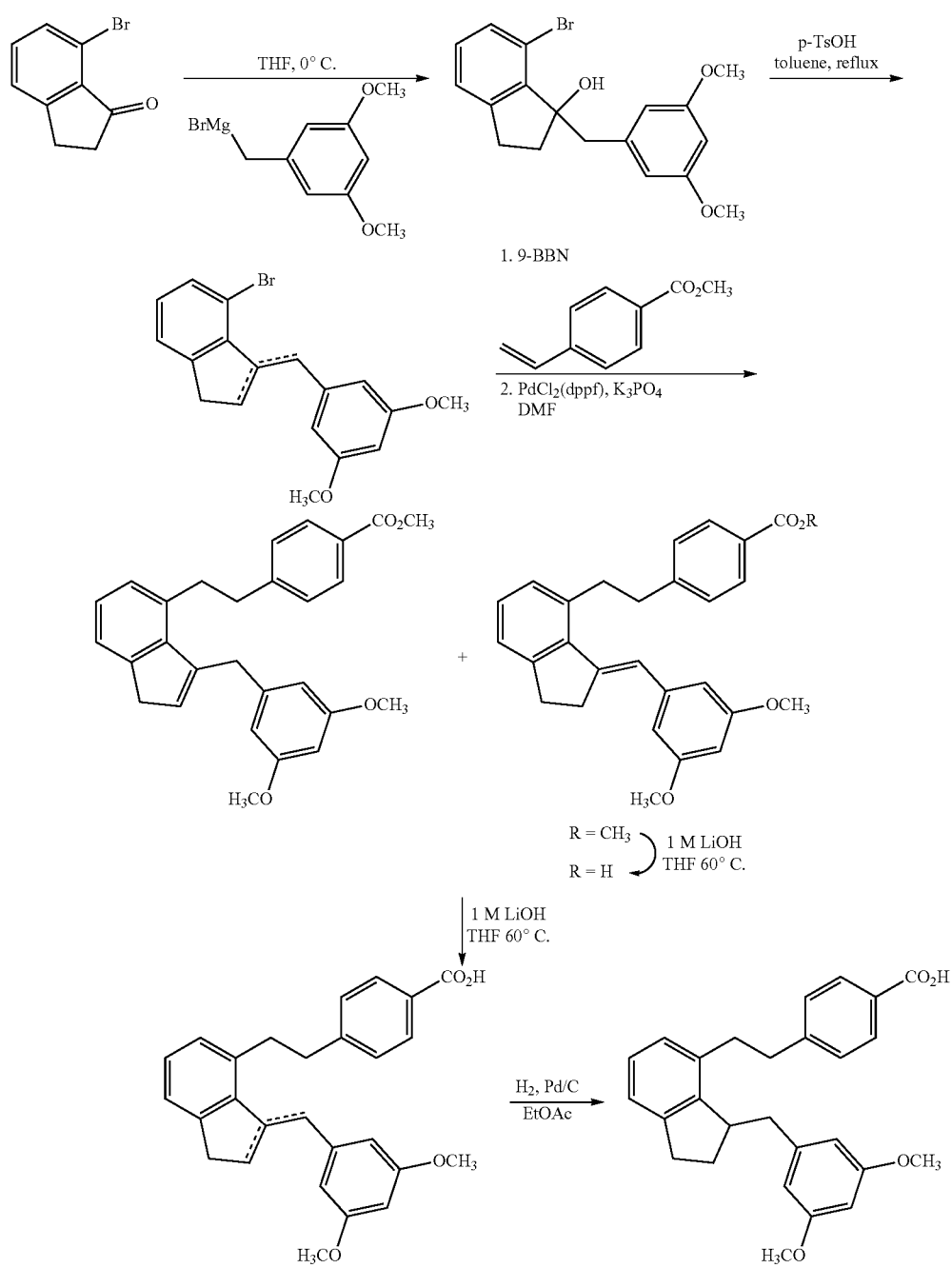
Scheme 12
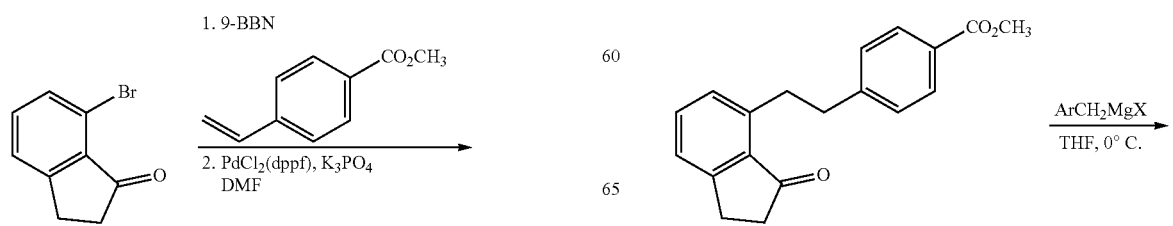
Scheme 13

27
-continued
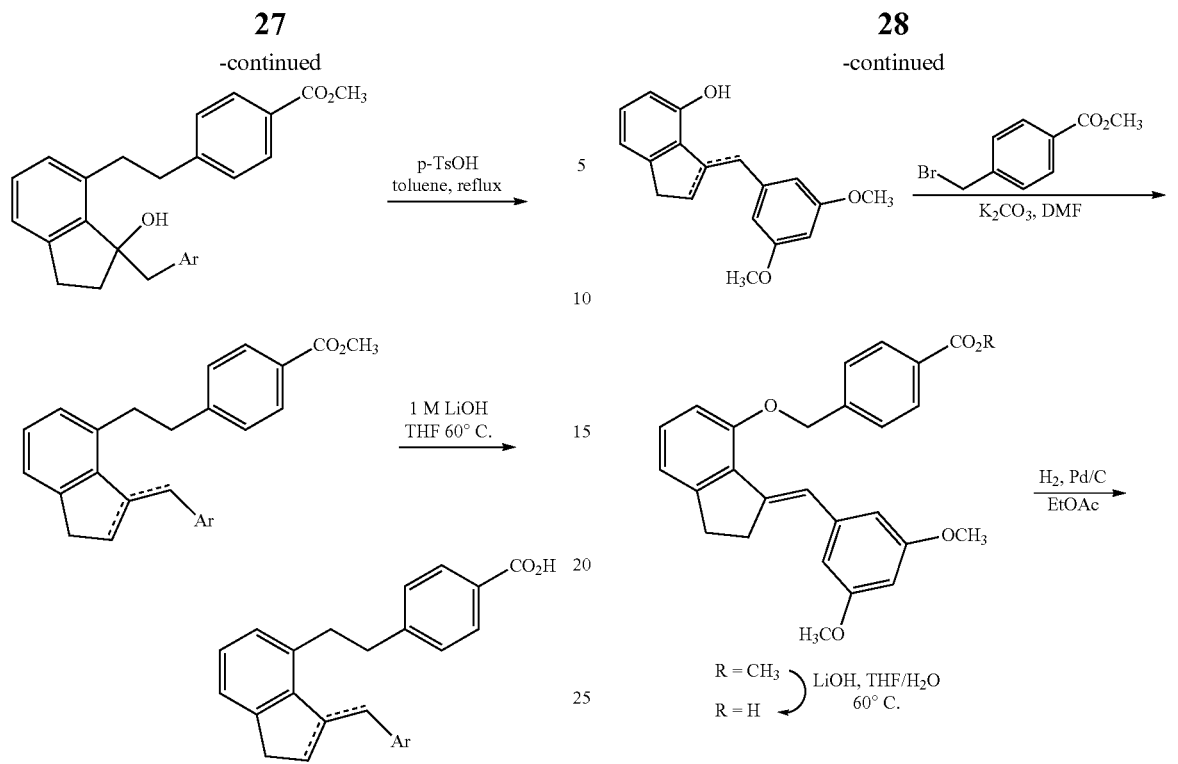
Scheme 14
28
-continued
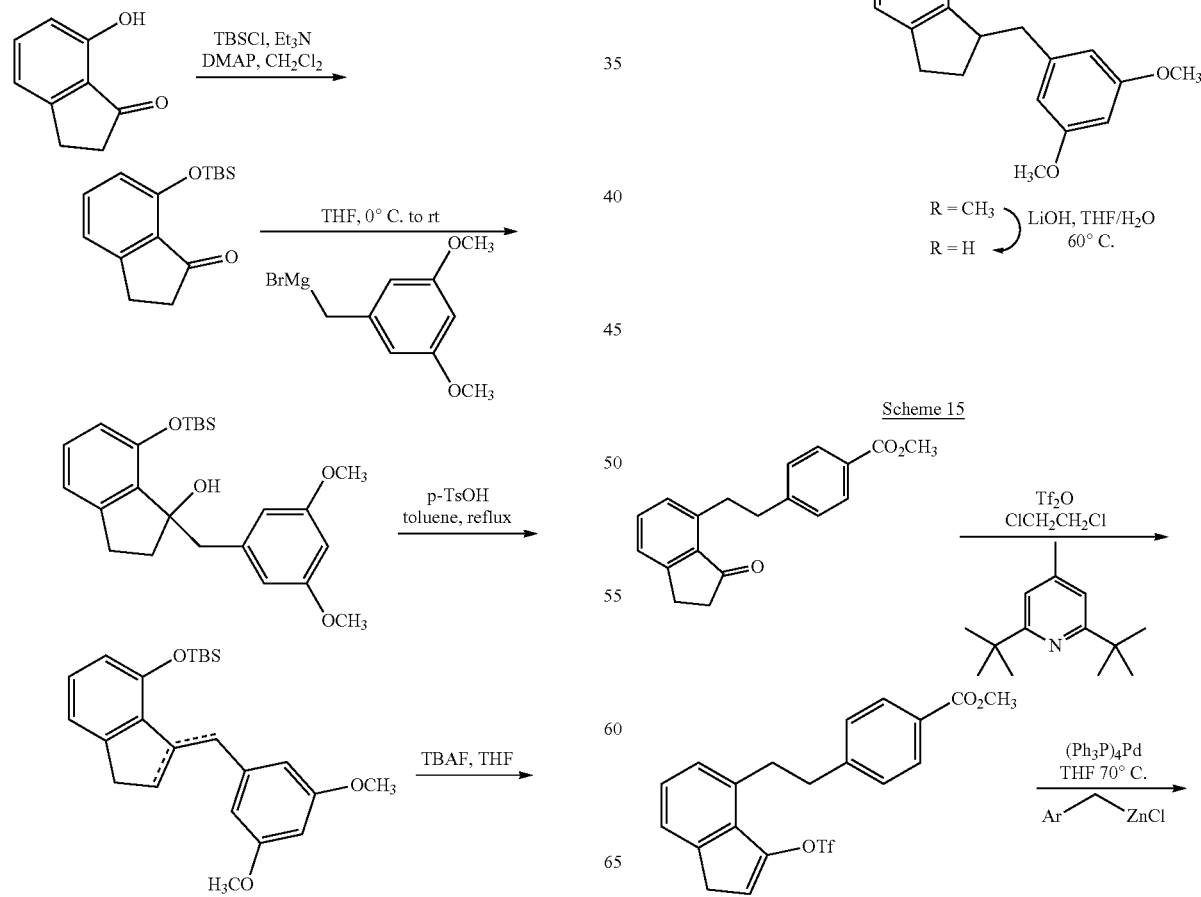
Scheme 15

29
-continued
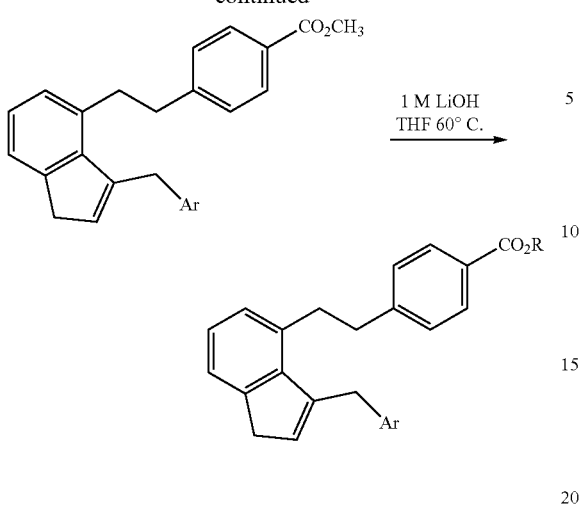
30
-continued
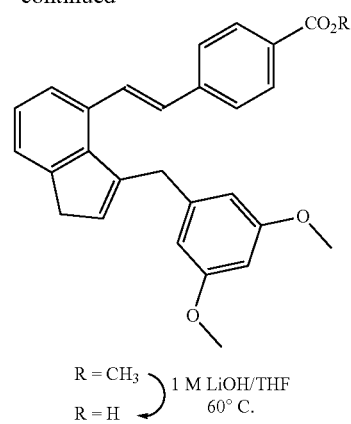
R = CH₃ } 1 M LiOH/THF
R = H      60° C.
Scheme 17
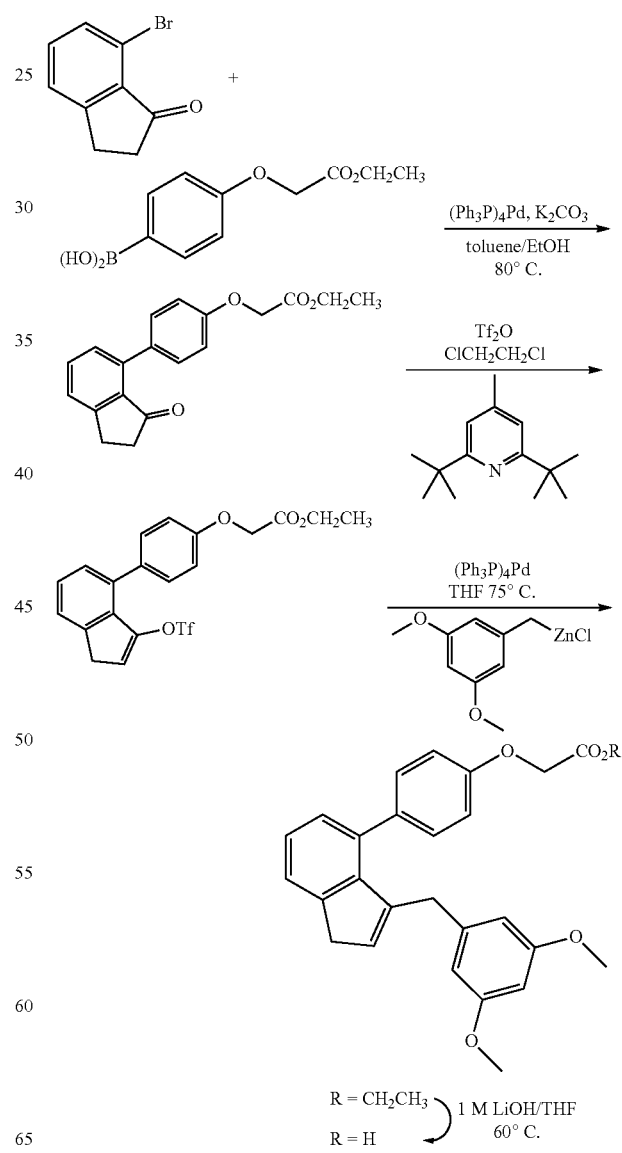
Scheme 16
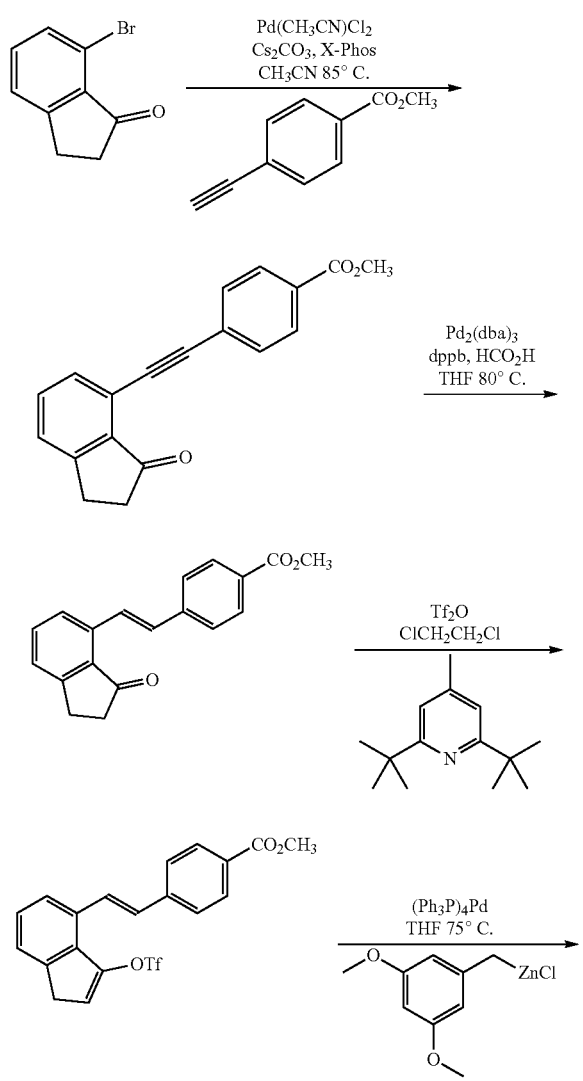

Scheme 18

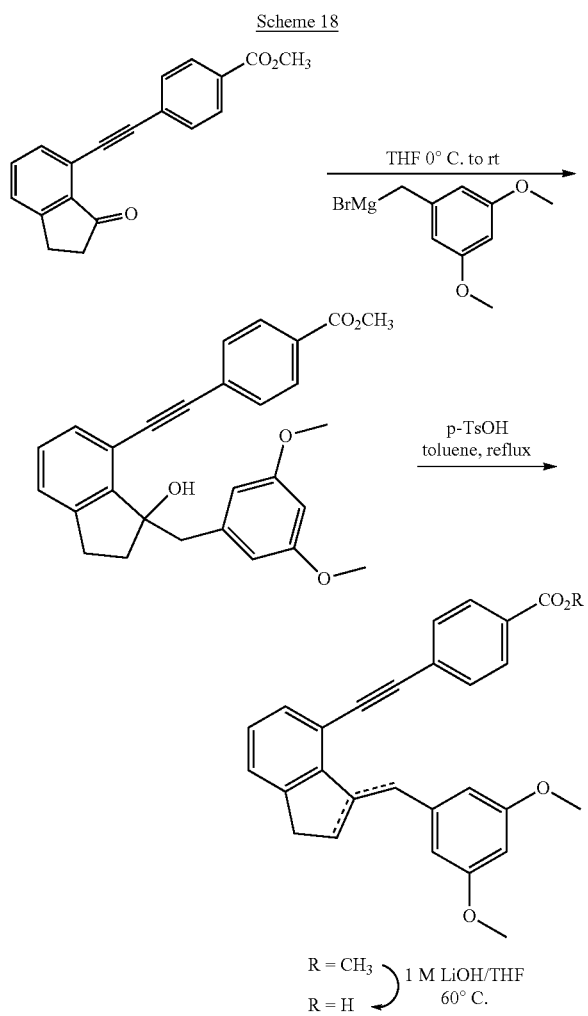

As used herein, the term "skin blemish" includes a flesh wound, scar, or wrinkle on any region of the skin of a body.

A "flesh wound" can be any area in which the structural integrity of the exterior surface of the skin is compromised. A flesh wound can be due to incision, laceration, abrasion, thermal burn, chemical burn, radiation or puncture of the skin. The wound can be superficial or extend to the deeper layers of the dermis, subcutaneous, deep fascia, muscle, bone or other internal organs.

A "scar" is an area of fibrous tissue (fibrosis) that replaces normal skin (or other tissue) after injury or disease. Scar types include hypertrophic scars, recessed scars, and stretch marks. Hypertrophic scars occur when the body overproduces collagen, which causes the scar to be raised above the surrounding skin. An example of a hypertrophic scar is a keloid scar. Atrophic, or recessed scars, have a sunken appearance and result when underlying support structure in the skin is lost. Stretch marks (striae) occur when skin is stretched rapidly (i.e., due to significant weight gain or growth spurt), or when skin is put under tension during the healing process, typically near a joint. As used herein, the term "scar" encompasses any type of scar in the skin due to any cause.

As used herein, the term "wrinkle" is a fold, ridge, crease, furrow, pit, crater, or sunken area in the skin that can be caused by habitual facial expressions, loss of collagen and/or elasticity due to aging, sun damage, smoking, poor hydration, and various other factors. A wrinkle can range from a deep crease to a fine line. Wrinkles occurring on any part of a body, in particular, wrinkles on head or neck of a subject are contemplated herein. Wrinkles that can be treated in accordance with the disclosure include, but are not limited to, a brow furrow, crows feet, nasolabial fold, one or more lines under the eyes or between the eye brows, and combinations thereof.

As used herein, "treatment" means to alleviate (or to eliminate) one or more features of a skin blemish either temporarily or permanently. When the compositions are administered to treat a wound, the compositions promote normal healing compared to a wound without the administration. That is, the size (length, depth, height and/or width), character, color and/or texture of the treated wound more closely resemble normal, non-wounded tissue. In this regard, treatment of a wound with the disclosed compositions can prevent, minimize or improve the appearance of a scar formation resulting from healing of the wound. Further, when the disclosed compositions are administered to treat a wrinkle, the wrinkle is treated if the appearance or prominence of the wrinkle is visibly or clinically diminished. That is the length and/or depth is decreased compared to the wrinkle prior to treatment. Alternatively, treatment can comprise prevention of a wrinkle. In this regard, the disclosed compositions can be applied to a region of the skin that typically develops a wrinkle, such as a forehead, lips, eyelids, nasolabial fold, skin under an eye, or between the eye brows in order to prevent the development of a wrinkle.

The disclosed compositions can be administered to prevent scar formation not associated with a wound, such as a stretch mark, or scars resulting from acne, chicken pox, measles or other disease states. In certain embodiments, the disclosed compositions are administered to the area of skin expansion in order to prevent formation of such scars. In these embodiments, the composition can be administered to any region of a face, abdomen, breasts, arms, legs, buttocks, back, or any other area where the skin is susceptible to developing a scar.

The compositions can be administered prior to, concurrently with, and/or after the development of the skin blemish. For instance, the disclosed compositions can be administered prior to an incision, during a surgical procedure, and/or any time post-operatively, and then additionally administered after the procedure as the healing process occurs. In another example, the compositions can be administered during pregnancy to prevent stretch marks. Alternately, the compositions can be administered after the development of a blemish.

The compositions may be administered between 1 and 7 days a week, for a period of time necessary to achieve the desired results, which may be several days to several months. The compositions can be administered once or several times (2, 3, 4, or more times) a day depending on the desired effect. In certain embodiments, the compositions can be administered every 1, 2, 3, 4, 5, 6, or 7 days. In another embodiment, the compositions can be administered one or more times every 1, 2, 3, or 4 weeks. The administration can be on a monthly or bi-monthly basis. Further, the compositions can be administered for 1, 2, 3, 6, 9, or 12 months or more. In certain embodiments, the compositions can be administered on an ongoing basis to maintain a desired result.

The disclosed compounds can be administered as part of a composition. As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with the presently disclosed compounds in order to provide a desired composition. Those of ordinary skill in the art will recognize a number of carriers that are well known for making specific pharmaceutical and/or cosmetic compositions. Desirably, the carrier is suitable for application to keratinous surfaces or other areas of the body. Upon application, acceptable carriers are substantially free of adverse reactions with skin and other keratinous surfaces. For example, the carriers may take the form of fatty or non-fatty creams, milky suspensions or emulsion-in-oil or oil-in-water types, lotions, gels or jellies, colloidal or non-colloidal aqueous or oily solutions, pastes, aerosols, soluble tablets or sticks. In accordance with one embodiment, the composition includes a dermatologically compatible vehicle or carrier. The vehicle which may be employed for preparing compositions may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

Examples of additional agents which can be included in the present compositions are anti-itch, anti-cellulite, anti-scarring, and anti-inflammatory agents, anesthetics, anti-irritants, vasoconstrictors, vasodilators, as well as agents to prevent/stop bleeding, and improve/remove pigmentation, moisturizers, desquamating agents, tensioning agents, anti-acne agents. Anti-itch agents can include methyl sulphonyl methane, sodium bicarbonate, calamine, allantoin, kaolin, peppermint, tea tree oil and combinations thereof. Anti-cellulite agents can include forskolin, xanthine compounds such as, but not limited to, caffeine, theophylline, theobromine, and aminophylline, and combinations thereof. Anesthetic agents can include lidocaine, benzocaine, butamben, dibucaine, oxybuprocaine, pramoxine, proparacaine, proxymetacaine, tetracaine, and combinations thereof. Anti-scarring agents can include IFN-.gamma., fluorouracil, poly(lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine and derivatives and combinations thereof. Additionally, active agents such as epinephrine, thymidine, cytidine, uridine, antiypyrin, aminocaproic acid, tranexamic acid, eucalyptol, allantoin, glycerin, and sodium selenite, can be included. Formulations can further comprise degradation inhibitors. Degradation inhibitors, include but are not limited to, glycosaminoglycans (e.g., heparin, heparin sulfate, dermatan sulfate, chrondroitin sulfate, o-sulfated HA, lnamarin, and amygdalin), antioxidants (e.g. ascorbic acid, melatonin, vitamin C, vitamin E), proteins (e.g., serum hyaluronidase inhibitor), and fatty acids (e.g. saturated $C_{10}$ to $C_{22}$ fatty acids). In certain embodiments, additional active agent is an antioxidant. In certain embodiments, the antioxidant comprises a vitamin C and/or a vitamin E such as d-alpha-tocopheryl polyethylene glycol 1000 succinate (TPGS).

The disclosed compositions are well suited for topical, subcutaneous, intradermal, subdermal, subcutaneous, and transdermal administration. Topical administration relates to the use of a composition applied to the surface of the skin at the site of a skin blemish for exertion of local action. Accordingly, such topical compositions include those pharmaceutical or cosmetic forms in which the composition is applied externally by direct contact with the skin surface to be treated, such as the face, neck, arms, legs, and/or torso. Conventional pharmaceutical or cosmetic forms for this purpose include ointments, liniments, creams, shampoos, lotions, pastes, jellies, sprays, aerosols, and the like, and may further be applied directly or in patches or impregnated dressings depending on blemish and skin region to be treated. The term "ointment" embraces formulations (including creams) having oleaginous, water-soluble and emulsion-type bases, e.g., petrolatum, lanolin, polyethylene glycols, as well as mixtures of these.

The compositions are appropriate for mesotherapy applications as well. Mesotherapy is a non-surgical cosmetic treatment technique involving intra-epidermal, intra-dermal, and/or subcutaneous injection of a composition. The compositions are administered in the form of small multiple droplets into the epidermis, dermo-epidermal junction, and/or the dermis.

In accordance with the disclosure, a pharmaceutical or cosmetic composition can optionally include one or more agents such as, without limitation, emulsifying agents, wetting agents, sweetening or flavoring agents, tonicity adjusters, preservatives, buffers antioxidants and flavonoids. Tonicity adjustors useful in a pharmaceutical composition of the present disclosure include, but are not limited to, salts such as sodium acetate, sodium chloride, potassium chloride, mannitol or glycerin and other pharmaceutically acceptable tonicity adjusters. Preservatives useful in the pharmaceutical compositions described herein include, without limitation, benzalkonium chloride, chlorobutanol, thimerosal, phenyl mercuric acetate, and phenyl mercuric nitrate. Various buffers and means for adjusting pH can be used to prepare a pharmaceutical composition, including but not limited to, acetate buffers, citrate buffers, phosphate buffers and borate buffers. Similarly, antioxidants useful in pharmaceutical compositions are well known in the art and include for example, sodium metabisulfite, sodium thiosulfate, acetylcysteine, butylated hydroxyanisole and butylated hydroxytoluene. Flavonoids are compounds found in plants that are well known to have diverse beneficial biochemical and antioxidant effects. Subcategories of flavonoids include: flavones, flavonols, flavanonse and flavanonols. Examples of flavonoids include: luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannis, condensed tannis, and hydrolysable tannis. It is understood that these and other substances known in the art can be included in a pharmaceutical or cosmetic composition disclosed herein.

As used herein, the term "therapeutically effective amount" means the amount of the pharmaceutical or cosmetic composition that will elicit the biological, medical, or cosmetic response of a subject in need thereof that is being sought by the researcher, veterinarian, medical doctor or other clinician. In some embodiments, the subject in need thereof is a mammal. In certain embodiments, the mammal is human. Effective amounts of the compound may be determined by one of ordinary skill in the art but will vary depending on the compound employed, frequency of application and desired result, and will generally range from about 0.0000001% to about 50%, by weight, of the composition, preferably from about 0.001% to about 50%, by weight, of total composition, more preferably from about 0.001% to about 30%, by weight of the composition. In certain embodiments, the compound is about 0.004% by weight of the composition.

The compounds described herein may be administered at least in the minimum dose necessary to achieve the desired therapeutic effect. Generally, such doses will be in the range of about 1 mg/day to about 1000 mg/day; more preferably in the range of about 10 mg/day to about 500 mg/day. In another example embodiment, the compound or compounds may be present in a composition or formulation in a range of about 0.0001 mg/kg/day to about 100 mg/kg/day or about 0.01 mg/kg/day to about 100 mg/kg/day. However, the actual amount of the compound to be administered in any given case will be determined by a physician taking into account the relevant circumstances, such as the age and weight of a patient, patient's general physical condition, severity of the skin blemish, and route of administration. In some instances, dosing is evaluated on a case-by-case basis.

Additionally, compositions may be designed to delay release of the compound over a given period of time, or to carefully control the amount of compound released at a given time during the course of treatment.

The pH of the disclosed compositions can be about 3 to about 8.0, or about 6.5 to about 7.5. In certain embodiments, the pH of the formulation is about 7.0 to about 7.4 or about 7.1 to about 7.3.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

Scheme 1 (Representative Procedures for Entries 1-8, Table 1)

Methyl 4-(2-(indolin-7-yl)ethyl)benzoate. A solution of methyl 4-vinyl benzoate (536 mg, 3.33 mmol) and 9-BBN dimer (812 mg, 3.33 mmol) in THF (10 mL) was stirred at room temperature for 19 h and then 0.5 mL $H_2O$ was added. After 30 minutes, the solution was cannula transferred to a mixture of 7-bromoindoline (527 mg, 2.66 mmol) and $PdCl_2$(dppf) (448 mg, 0.55 mmol) in 10 mL DMF. $K_3PO_4$ solution (1.4 mL, 3 M) was added after 5 minutes and the dark mixture was stirred at room temperature overnight. The mixture was then partitioned between 50 mL ethyl acetate and 50 mL $H_2O$ and the ethyl acetate solution was further washed with $H_2O$ (3×50 mL). The solution was then dried ($Na_2SO_4$), filtered and evaporated. Purification of the residue by flash chromatography on silica gel using a Combiflash unit by Teledyne Isco (0% ethyl acetate/hexanes→40%) followed by another flash chromatography (0% ethyl acetate/$CH_2Cl_2$→10%) gave the title compound (320 mg, 33%).

Methyl 4-(2-(1-(3-fluorobenzyl)indolin-7-yl)ethyl)benzoate. A mixture of methyl 4-(2-(indolin-7-yl)ethyl)benzoate (22 mg, 0.078 mmol), 3-fluorobenzyl bromide (12 μL, 0.10 mmol) and $K_2CO_3$ (20 mg, 0.14 mmol) in 0.2 mL DMF was stirred at room temperature. After 22 h, 20 mL ethyl acetate was added and the resulting mixture was washed with $H_2O$ (4×25 mL) and then was dried ($Na_2SO_4$), filtered and evaporated to give the title compound (10 mg) which was used directly in the next step.

4-(2-(1-(3-fluorobenzyl)indolin-7-yl)ethyl)benzoic acid. A mixture of methyl 4-(2-(1-(3-fluorobenzyl) indolin-7-yl) ethyl)benzoate (10 mg, 0.026 mmol), LiOH solution (0.2 mL, 0.2 mmol, 1 M) and 1,4-dioxane (1 mL) was heated at 80° C. for 19 h. HCl solution (10 mL, 0.1 M) was added and the resulting mixture was extracted with $CH_2Cl_2$ (3×15 mL). The combined organic solution was then dried ($Na_2SO_4$), filtered and evaporated to give the title compound (10 mg).

Scheme 2 (Entry 9, Table 1)

tert-Butyl 3,4-dihydroquinoline-1(2H)-carboxylate. Di-tert-butyl dicarbonate (1.181 g, 5.4 mmol) was added to a solution of 1,2,3,4-tetrahydroquinoline (626 mg, 4.7 mmol), triethylamine (1.3 mL, 9.3 mmol) and DMAP (112 mg, 0.19 mmol) in $CH_3CN$ (15 mL). The reaction was stirred for 1.5 h at room temperature and then was heated overnight at 55° C. The solution was allowed to cool to room temperature and then was evaporated. The residue was partitioned between 25 mL ethyl acetate and 25 mL 1 M HCl. The ethyl acetate solution was further washed with 1 M HCl (2×25 mL) and 25 mL brine and then was dried ($Na_2SO_4$), filtered and evaporated. Purification of the residue by flash chromatography on silica gel using a Combiflash unit by Teledyne Isco (0% ethyl acetate/hexanes→40%) gave the title compound (139 mg, 13%).

tert-Butyl 8-iodo-3,4-dihydroquinoline-1(2H)-carboxylate. A similar procedure to that described in Peter Beak, Won-Koo Lee *Tetrahedron Letters* 1989, 30, 1197-1200 was used: sec-Butyllithium (0.51 mL, 0.71 mmol) was added to a −78° C. solution of tert-butyl 3,4-dihydroquinoline-1(2H)-carboxylate (139 mg, 0.59 mmol) and N,N,N',N'-tetramethylethylenediamine (TMEDA, 0.2 mL, 1.33 mmol) in diethyl ether (1.2 mL). After 3 h, a solution of 1,2-diiodoethane (201 mg, 0.71 mL) in 1 mL diethyl ether was added by cannula and the reaction was allowed to warm to room temperature. After 19 h, the mixture was partitioned between 20 mL $H_2O$ and 20 mL diethyl ether. The aqueous layer was further extracted with 20 mL diethyl ether and the combined ether solution was dried ($Na_2SO_4$), filtered and evaporated. Purification of the residue by flash chromatography on silica gel using a Combiflash unit by Teledyne Isco (0% ethyl acetate/hexanes→40%) gave the title compound (154 mg, 73%).

8-Iodo-1,2,3,4-tetrahydroquinoline. A solution of tert-butyl 8-iodo-3,4-dihydroquinoline-1 (2H)-carboxylate (82 mg, 0.23 mmol) in 4 M HCl/dioxane (1 mL, 4 mmol) was stirred at room temperature. After 1 h, 20 mL 1 M NaOH solution was added and the resulting mixture was extracted with ethyl acetate (2×20 mL). The combined ethyl acetate solution was dried ($Na_2SO_4$), filtered and evaporated to give the title compound as a clear, colorless oil (57 mg, 0.22 mmol, 96%).

Methyl 4-(2-(1,2,3,4-tetrahydroquinolin-8-yl)ethyl)benzoate. The procedure described above for methyl 4-(2-(indolin-7-yl)ethyl)benzoate was used, starting with 8-iodo-1,2,3,4-tetrahydroquinoline (57 mg, 0.22 mmol) and methyl 4-vinylbenzoate (46 mg, 0.29 mmol) which gave the title compound (31 mg, 0.10 mmol, 48%).

Methyl 4-(2-(1-(3,5-dimethoxybenzyl)-1,2,3,4-tetrahydroquinolin-8-yl)ethyl)benzoate. A mixture of methyl 4-(2-(1,2,3,4-tetrahydroquinolin-8-yl)ethyl)benzoate (18 mg, 0.061 mmol), $K_2CO_3$ (18 mg, 0.13 mmol), and 3,5-dimethoxybenzyl bromide (14 mg, 0.061 mmol) in DMF (0.2 mL) was stirred at room temperature. After 20 h, 20 mL ethyl acetate was added and the resulting mixture was washed with $H_2O$ (4×25 mL) and then was dried ($Na_2SO_4$), filtered and evaporated which gave the title compound contaminated with the other starting materials. The residue was taken up in 0.2 mL DMF and $K_2CO_3$ (21 mg) and 3,5-dimethoxybenzyl bromide (6 mg) were added and the resulting mixture was stirred at 50° C. for 2 h and at 70° C. for 2.5 h. The resulting mixture was allowed to cool to room temperature and was then worked-up as before. Purification of the residue by flash chromatography on silica gel using a Combiflash unit by Teledyne Isco (0% ethyl acetate/hexanes→2%) followed by further purification by preparative thin layer chromatography (silica gel, $CH_2Cl_2$) gave the title compound (7 mg, 26%).

4-(2-(1-(3,5-Dimethoxybenzyl)-1,2,3,4-tetrahydroquinolin-8-yl)ethyl)benzoic acid. The procedure described above for 4-(2-(1-(3-fluorobenzyl)indolin-7-yl)ethyl)benzoic acid was used with methyl 4-(2-(1-(3,5-dimethoxybenzyl)-1,2,3,4-tetrahydroquinolin-8-yl)ethyl)benzoate (7 mg, 0.016 mmol) and 1 M LiOH (0.2 mL) in 1 mL dioxane. The crude residue was purified by preparative thin layer chromatography on silica gel (50% ethyl acetate/hexanes) which gave the title compound (2 mg, 29%).

Scheme 3 (Entries 10-11, Table 1)

4-Bromo-2-(3-methoxybenzyl)isoindoline. A mixture of 4-bromoisoindoline (98 mg, 0.49 mmol), 3-methoxybenzyl bromide (69 μL, 0.49 mmol) and $K_2CO_3$ (66 mg, 0.48 mmol) in 2 mL acetone was stirred at room temperature. After overnight stirring, the mixture was partitioned between 25 mL $H_2O$/25 mL $CH_2Cl_2$. The aqueous layer was further extracted with $CH_2Cl_2$ (25 mL) and the combined organic solution was dried ($Na_2SO_4$), filtered and evaporated. Purification of the residue by flash chromatography on silica gel using a Combiflash unit by Teledyne Isco (0% ethyl acetate/hexanes→40%) gave the title compound (32 mg, 20%).

Methyl 4-(2-(2-(3-methoxybenzyl)isoindolin-4-yl)ethyl)benzoate. The procedure described above for methyl 4-(2-(indolin-7-yl)ethyl)benzoate was used, starting with 4-bromo-2-(3-methoxybenzyl)isoindoline (32 mg, 0.10 mmol) and methyl 4-vinylbenzoate (19 mg, 0.12 mmol) which gave the title compound (23 mg, 0.057 mmol, 57%).

4-(2-(2-(3-Methoxybenzyl)isoindolin-4-yl)ethyl)benzoic acid. The procedure described above for 4-(2-(1-(3-fluorobenzyl)indolin-7-yl)ethyl)benzoic acid was used with methyl 4-(2-(2-(3-methoxybenzyl)isoindolin-4-yl)ethyl) benzoate (11 mg, 0.027 mmol) and 1 M LiOH (0.1 mL) in 1 mL dioxane, heating overnight at 60° C. This gave the title compound (11 mg, 100%).

4-Bromo-2-(3-methoxyphenethyl)isoindoline. A mixture of 4-bromoisoindoline (107 mg, 0.54 mmol), 1-(2-bromoethyl)-3-methoxybenzene (89 μL, 0.57 mmol) and $K_2CO_3$ (75 mg, 0.54 mmol) in 1 mL DMF was stirred at room temperature. After overnight stirring, the mixture was partitioned between 25 mL $H_2O$/25 mL ethyl acetate. The ethyl acetate layer was washed with water (3×25 mL) and the combined organic solution was dried ($Na_2SO_4$), filtered and evaporated. Purification of the residue by flash chromatography on silica gel using a Combiflash unit by Teledyne Isco (0% ethyl acetate/hexanes→50%) gave the title compound (26 mg, 14%).

Methyl 4-(2-(2-(3-methoxyphenethyl)isoindolin-4-yl) ethyl)benzoate. The procedure described above for methyl 4-(2-(indolin-7-yl)ethyl)benzoate was used, starting with 4-bromo-2-(3-methoxyphenethyl)isoindoline (26 mg, 0.078 mmol) and methyl 4-vinylbenzoate (17 mg, 0.11 mmol) which gave the title compound (19 mg, 0.046 mmol, 59%).

4-(2-(2-(3-Methoxyphenethyl)isoindolin-4-yl)ethyl)benzoic acid. The procedure described above for 4-(2-(1-(3-fluorobenzyl)indolin-7-yl)ethyl)benzoic acid was used with methyl 4-(2-(2-(3-methoxyphenethyl)isoindolin-4-yl)ethyl) benzoate (10 mg, 0.024 mmol) and 1 M LiOH (0.1 mL) in 1 mL dioxane, heating overnight at 60° C. Purification of the crude product by preparative thin layer chromatography on silica gel (5% methanol/$CH_2Cl_2$) gave the title compound (6 mg, 62%).

Scheme 4 (Entry 12, Table 1)

Methyl 4-(2-(isoindolin-4-yl)ethyl)benzoate. The procedure described above for methyl 4-(2-(indolin-7-yl) ethyl) benzoate was used, starting with 4-bromoisoindoline (252 mg, 0.1.27 mmol) and methyl 4-vinylbenzoate (246 mg, 1.53 mmol). Purification of the crude product by flash chromatography on silica gel (2% methanol/$CH_2Cl_2$ (0.5% triethylamine)→4%) gave the title compound (155 mg, 43%).

Methyl 4-(2-(2-(3,5-dimethoxyphenyl)isoindolin-4-yl) ethyl)benzoate. The procedure described in Wolfe, J. P.; Buchwald, S. L. *Angew. Chem. Int. Ed. Engl.* 1999, 38, 2413 was used. A mixture of methyl 4-(2-(isoindolin-4-yl)ethyl) benzoate (64 mg, 0.23 mmol), Pd(OAc)2 (1 mg, 0.0045 mmol), 1-bromo-3,5-dimethoxybenzene (62 mg, 0.29 mmol), Johnphos (3 mg, 0.01 mmol), and tert-BuONa (32 mg, 0.33 mmol) in toluene was stirred at room temperature. After 20 h, the mixture was partitioned between 10 mL $H_2O$/20 mL ethyl acetate. The aqueous layer was further extracted with 20 mL ethyl acetate and the combined ethyl acetate solution was dried ($Na_2SO_4$), filtered and evaporated. Purification of the residue by flash chromatography on silica gel using a Combiflash unit by Teledyne Isco (0% ethyl acetate/hexanes→30%) gave the title compound (17 mg, 18%).

4-(2-(2-(3,5-Dimethoxyphenyl)isoindolin-4-yl)ethyl) benzoic acid. The procedure described above for 4-(2-(1-(3-fluorobenzyl)indolin-7-yl)ethyl)benzoic acid was used with methyl 4-(2-(2-(3,5-dimethoxyphenyl)isoindolin-4-yl) ethyl)benzoate (9 mg, 0.021 mmol) and 1 M LiOH (0.2 mL) in 1 mL dioxane, heating overnight at 80° C. Purification of the crude product by preparative thin layer chromatography on silica gel (5% methanol/$CH_2Cl_2$) gave the title compound (6 mg, 69%).

Scheme 5 (Entries 13-14, Table 1)

Methyl 5-bromothiophene-2-carboxylate. A solution of 5-bromothiophene-2-carboxylic acid (4.995 g, 24.1 mmol)

in 30 mL CH₃OH/8 mL acetyl chloride was heated at 65° C. After 22 h, the reaction was allowed to cool to room temperature and then was evaporated. The residue was partitioned between 100 mL saturated NaHCO$_3$ solution/75 mL ethyl acetate. The ethyl acetate layer was further washed with saturated NaHCO$_3$ solution (75 mL) and then was dried (Na$_2$SO$_4$), filtered and evaporated to give the title compound (4.921 g, 22.3 mmol, 93%).

Methyl 5-vinylthiophene-2-carboxylate. A procedure described in Molander, G. A.; Brown, A. R. *J. Org. Chem.* 2006, 71, 9681 was used: A mixture of methyl 5-bromothiophene-2-carboxylate (104 mg, 0.47 mmol), potassium vinyltrifluoroborate (67 mg, 0.50 mmol), PdCl$_2$ (9 mg, 0.05 mmol), PPh$_3$ (42 mg, 0.16 mmol), and Cs$_2$CO$_3$ (380 mg, 1.2 mmol) in 9:1 THF/H$_2$O (1 mL) was stirred at 85° C. After 20 h, the reaction was allowed to cool to room temperature and then was partitioned between 10 mL H$_2$O/25 mL CH$_2$Cl$_2$. The aqueous layer was further extracted with CH$_2$Cl$_2$ (2×15 mL) and the combined CH$_2$Cl$_2$ solution was dried (Na$_2$SO$_4$), filtered and evaporated. Purification of the residue by flash chromatography on silica gel using a Combiflash unit by Teledyne Isco (0% ethyl acetate/hexanes→40%) gave the title compound (52 mg, 66%).

This intermediate was taken on to the final compounds using analogous procedures as those shown in Scheme 1 and described above.

Scheme 6 (Entry 15, Table 1)

7-Iodo-1-(3-methoxybenzyl)-1H-indole. NaH (54 mg, 1.3 mmol, 60% in mineral oil) was added to a solution of 7-iodo-1H-indole (273 mg, 1.1 mmol). After 15 minutes, 3-methoxybenzyl bromide (169 µL, 1.2 mmol) was added and the mixture was stirred at room temperature. After 20 h, the reaction was partitioned between 30 mL ethyl acetate/25 mL H$_2$O. The organic layer was further washed with H$_2$O (3×25 mL) and then was dried (Na$_2$SO$_4$), filtered and evaporated. Purification of the residue by flash chromatography on silica gel using a Combiflash unit by Teledyne Isco (0% ethyl acetate/hexanes→40%) gave the title compound (314 mg, 79%).

Methyl 4-(2-(1-(3-methoxybenzyl)-1H-indol-7-yl)ethyl) benzoate. The procedure described above for methyl 4-(2-(indolin-7-yl)ethyl)benzoate was used, starting with 7-iodo-1-(3-methoxybenzyl)-1H-indole (94 mg, 0.26 mmol) and methyl 4-vinylbenzoate (46 mg, 0.29 mmol) which gave the title compound (18 mg, 17%).

4-(2-(1-(3-Methoxybenzyl)-1H-indol-7-yl)ethyl)benzoic acid. The procedure described above for 4-(2-(1-(3-fluorobenzyl)indolin-7-yl)ethyl)benzoic acid was used with methyl 4-(2-(1-(3-methoxybenzyl)-1H-indol-7-yl)ethyl) benzoate (9 mg, 0.023 mmol) and 1 M LiOH (0.1 mL) in 1 mL dioxane, heating overnight at 60° C. This gave the title compound (7 mg, 78%).

Scheme 7 (Entries 16-17, Table 1)

1-(7-Bromoindolin-1-yl)-2-(3-methoxyphenyl)ethanone. 2-(3-Methoxyphenyl)acetic acid (124 mg, 0.75 mmol) was added to a mixture of 7-bromoindoline (137 mg, 0.69 mmol) and N-(3-dimethylaminopropyl)-N'-ethylcarbodiimide (EDCI, 191 mg, 1.0 mmol) in 2 mL CH$_2$Cl$_2$. After 23 h, 10 mL saturated NaHCO$_3$ solution was added and the resulting mixture was extracted with CH$_2$Cl$_2$ (2×20 mL). The organic layer was dried (Na$_2$SO$_4$), filtered and evaporated. Purification of the residue by flash chromatography on silica gel using a Combiflash unit by Teledyne Isco (0% ethyl acetate/hexanes→60%) gave the title compound (177 mg, 51%).

7-Bromo-1-(3-methoxyphenethyl)indoline. BH$_3$.THF (0.5 mL, 0.5 mmol) was added to a solution of 1-(7-bromoindolin-1-yl)-2-(3-methoxyphenyl)ethanone (55 mg, 0.16 mmol) in 1 mL THF. After 20 h, 5 mL 2.5 M HCl was added slowly and the mixture was stirred for 45 minutes. NaOH (5 mL, 3 M) was added, the resulting mixture was extracted with ethyl acetate (2×20 mL) and the combined organic solution was dried (Na$_2$SO$_4$), filtered and evaporated. Purification of the residue by flash chromatography on silica gel using a Combiflash unit by Teledyne Isco (0% ethyl acetate/hexanes→40%) gave the title compound (33 mg, 63%).

Methyl 4-(2-(1-(3-methoxyphenethyl)indolin-7-yl)ethyl) benzoate. The procedure described above for methyl 4-(2-(indolin-7-yl)ethyl)benzoate was used, starting with 7-bromo-1-(3-methoxyphenethyl)indoline (33 mg, 0.10 mmol) and methyl 4-vinylbenzoate (20 mg, 0.12 mmol). The title compound (14 mg, 34%) was obtained after a final purification by preparative thin layer chromatography on silica gel (CH$_2$Cl$_2$).

4-(2-(1-(3-Methoxyphenethyl)indolin-7-yl)ethyl)benzoic acid. The procedure described above for 4-(2-(1-(3-fluorobenzyl)indolin-7-yl)ethyl)benzoic acid was used with methyl 4-(2-(1-(3-methoxyphenethyl)indolin-7-yl)ethyl) benzoate (14 mg, 0.034 mmol) and 1 M LiOH (0.2 mL) in 1 mL dioxane, heating overnight at 80° C. This gave the title compound (15 mg, 100%).

Methyl 4-(2-(1-(2-(3-methoxyphenyl)acetyl)indolin-7-yl) ethyl)benzoate. The procedure described above for methyl 4-(2-(indolin-7-yl)ethyl)benzoate was used, starting with 1-(7-bromoindolin-1-yl)-2-(3-methoxyphenyl)ethanone (52 mg, 0.15 mmol) and methyl 4-vinylbenzoate (33 mg, 0.20 mmol). The title compound (8 mg, 12%) was obtained after a final purification by preparative thin layer chromatography on silica gel (40% ethyl acetate/hexanes).

4-(2-(1-(2-(3-Methoxyphenyl)acetyl)indolin-7-yl)ethyl) benzoic acid. The procedure described above for 4-(2-(1-(3-fluorobenzyl)indolin-7-yl)ethyl)benzoic acid was used with methyl 4-(2-(1-(2-(3-methoxyphenyl)acetyl)indolin-7-yl)ethyl)benzoate (8 mg, 0.019 mmol) and 1 M LiOH (0.2 mL) in 1 mL dioxane, heating overnight at 80° C. This gave the title compound (5 mg, 63%) after purification by preparative thin layer chromatography on silica gel (50% ethyl acetate/hexanes).

Scheme 8 (Entry 18, Table 1)

Methyl 4-(2-(1-(3,5-dimethoxybenzoyl)indolin-7-yl) ethyl)benzoate. Triethylamine (18 µL, 0.13 mmol) was added to a solution of methyl 4-(2-(indolin-7-yl)ethyl)benzoate (19 mg, 0.066 mmol) and 3,5-dimethoxybenzoyl chloride (13 mg, 0.065 mmol) in CH$_2$Cl$_2$ (0.75 mL). After 3 h, 10 ml 1 M HCl solution was added and the resulting mixture was extracted with CH$_2$Cl$_2$ (2×20 mL). The combined organic solution was dried (Na$_2$SO$_4$), filtered and evaporated. Purification of the residue by flash chromatography on silica gel using a Combiflash unit by Teledyne Isco (0% ethyl acetate/hexanes→20%) gave the title compound (26 mg, 90%).

4-(2-(1-(3,5-Dimethoxybenzoyl)indolin-7-yl)ethyl)benzoic acid. The procedure described above for 4-(2-(1-(3-fluorobenzyl)indolin-7-yl)ethyl)benzoic acid was used with methyl 4-(2-(1-(3,5-dimethoxybenzoyl)indolin-7-yl)ethyl) benzoate (11 mg, 0.025 mmol) and 1 M LiOH (0.2 mL) in 1 mL dioxane, heating overnight at 60° C. This gave the title compound (11 mg, 100%).

Scheme 9 (Entries 19-20, Table 1)

Methyl 4-(2-(1-((3-methoxyphenyl)sulfonyl)indolin-7-yl)ethyl)benzoate. Pyridine (26 µL, 0.32 mmol) was added to a solution of methyl 4-(2-(indolin-7-yl)ethyl)benzoate (23 mg, 0.080 mmol) and 3-methoxybenzene-1-sulfonyl chloride (12 µL, 0.085 mmol) in THF (0.5 mL). After 22 h, 15 mL 1 M HCl solution was added and the resulting mixture was extracted with ethyl acetate (20 mL). The organic solution was then dried (Na$_2$SO$_4$), filtered and evaporated. Purification of the residue by flash chromatography on silica gel using a Combiflash unit by Teledyne Isco (0% ethyl acetate/hexanes→40%) gave the title compound (32 mg, 89%).

4-(2-(1-((3-Methoxyphenyl)sulfonyl)indolin-7-yl)ethyl) benzoic acid. The procedure described above for 4-(2-(1-(3-fluorobenzyl)indolin-7-yl)ethyl)benzoic acid was used with heating at 60° C. instead of 80° C.

Methyl 4-(2-(1-((3,5-dimethoxyphenyl)sulfonyl)indolin-7-yl)ethyl)benzoate. The procedure described for methyl 4-(2-(1-((3-methoxyphenyl)sulfonyl)indolin-7-yl)ethyl) benzoate was used.

4-(2-(1-((3,5-Dimethoxyphenyl)sulfonyl)indolin-7-yl) ethyl)benzoic acid. The procedure described above for 4-(2-(1-(3-fluorobenzyl)indolin-7-yl)ethyl)benzoic acid was used with heating at 60° C. instead of 80° C.

Scheme 10 (Entries 21-23, Table 1)

7-Bromo-1-(3-methoxybenzyl)indoline. A mixture of 7-bromoindoline (152 mg, 0.77 mmol), 3-methoxybenzyl bromide (107 µL, 0.76 mmol) and K$_2$CO$_3$ (170 mg, 1.2 mmol) in 1.2 mL DMF was stirred at room temperature for 3 h and for 20 h at 50° C. The mixture was then allowed to cool to room temperature and was partitioned between 25 mL ethyl acetate and 25 mL H2O. The organic layer was further washed with H$_2$O (3×25 mL) and then was dried (Na$_2$SO$_4$), filtered and evaporated to give the title compound which was used directly in the next step.

7-Bromo-1-(3-(trifluoromethyl)benzyl)indoline. The procedure described above for methyl 4-(2-(1-(3-fluorobenzyl) indolin-7-yl)ethyl)benzoate was followed using 7-bromoindoline (126 mg, 0.63 mmol), 3-(trifluoromethyl)benzyl bromide (97 µL, 0.63 mmol) and K$_2$CO$_3$ (148 mg, 1.1 mmol) in 1 mL DMF. Purification of the crude product by flash chromatography on silica gel using a Combiflash unit by Teledyne Isco (0% ethyl acetate/hexanes→50%) gave the title compound (194 mg, 87%).

7-Bromo-1-phenethylindoline. A mixture of 7-bromoindoline (70 mg, 0.35 mmol), 2-phenylethylbromide (48 µL, 0.35 mmol) and K$_2$CO$_3$ (100 mg, 0.72 mmol) was stirred for 3 h at 50° C. and for 19 h at 80° C. At this time, the mixture was partitioned between H$_2$O/ethyl acetate and the ethyl acetate solution was washed with H$_2$O (3×). The solution was then dried (Na$_2$SO$_4$), filtered and evaporated. Purification of the residue by preparative TLC (10% ethyl acetate/ hexanes) gave the title compound (22 mg, 21%).

These substituted bromoindoline compounds were processed to the final compounds as shown in Scheme 10 using procedures described for 4-(2-(1-(3-fluorobenzyl)indolin-7-yl)ethyl)benzoic acid (Scheme 1).

Scheme 11 (Entry 24, Table 1)

tert-Butyl 5-fluoroindoline-1-carboxylate. A procedure similar to that described in Iwao, M.; Kuraishi, T. *Heterocycles* 1992, 34, 1031 was used. A solution of 5-fluoroindoline (100 mg, 0.73 mmol) and di-tert-butyl dicarbonate (188 mg, 0.86 mmol) in 2 mL THF was stirred at room temperature overnight. At this time, 20 mL saturated NaHCO$_3$ solution was added and the mixture was extracted with ethyl acetate (20 mL). The ethyl acetate solution was then dried (Na$_2$SO$_4$), filtered and evaporated. Purification of the residue by flash chromatography on silica gel using a Combiflash unit by Teledyne Isco (0% ethyl acetate/ hexanes→20%) gave the title compound (140 mg, 81%).

tert-Butyl 5-fluoro-7-iodoindoline-1-carboxylate. A similar procedure as that described for tert-butyl 8-iodo-3,4-dihydroquinoline-1(2H)-carboxylate was used.

5-Fluoro-7-iodoindoline. A solution of tert-butyl 5-fluoro-7-iodoindoline-1-carboxylate (70 mg, 0.19 mmol) in 4 M HCl/dioxane (1 mL) was stirred at 60° C. After 1 h, 1 M NaOH (20 mL) was added and the resulting mixture was extracted with ethyl acetate (3×20 mL). The combined organic solution was washed with brine and was then dried (Na$_2$SO$_4$), filtered and evaporated. Purification of the residue by flash chromatography on silica gel using a Combiflash unit by Teledyne Isco (ethyl acetate/hexanes) gave the title compound (30 mg, 60%).

Methyl 4-(2-(5-fluoroindolin-7-yl)ethyl)benzoate. The procedure described above for methyl 4-(2-(indolin-7-yl) ethyl)benzoate was used, starting with 5-fluoro-7-iodoindoline (30 mg, 0.11 mmol) and methyl 4-vinylbenzoate (27 mg, 0.17 mmol). Purification of the residue by flash chromatography on silica gel using a Combiflash unit by Teledyne Isco (ethyl acetate/hexanes) gave the title compound (28 mg, 85%).

Methyl 4-(2-(1-(3,5-dimethoxybenzyl)-5-fluoroindolin-7-yl)ethyl)benzoate. A mixture of methyl 4-(2-(5-fluoroindolin-7-yl)ethyl)benzoate (28 mg, 0.096 mmol), 3,5-dimethoxybenzyl bromide (25 mg, 0.11 mmol) and K$_2$CO$_3$ (35 mg, 0.25 mmol) in 1.3 mL DMF was stirred at room temperature overnight. The mixture was then partitioned between 25 mL H$_2$O/20 mL ethyl acetate. The aqueous layer was further extracted with ethyl acetate (3×20 mL) and the combined ethyl acetate solution was washed with water (3×20 mL) and brine. The solution was then dried (Na$_2$SO$_4$), filtered and evaporated. Purification of the residue by flash chromatography on silica gel using a Combiflash unit by Teledyne Isco (ethyl acetate/hexanes) gave the title compound (28 mg, 65%).

4-(2-(1-(3,5-Dimethoxybenzyl)-5-fluoroindolin-7-yl) ethyl)benzoic acid. The procedure described above for 4-(2-(1-(3-fluorobenzyl)indolin-7-yl)ethyl)benzoic acid was followed using methyl 4-(2-(1-(3,5-dimethoxybenzyl)-5-fluoroindolin-7-yl)ethyl)benzoate (28 mg, 0.063 mmol), 1 M LiOH (0.34 mL, 0.34 mmol) and 3.4 mL THF as solvent with overnight heating at 60° C. Purification of the crude product by preparative thin layer chromatography on silica gel (methanol/CH$_2$Cl$_2$) gave the title compound as a white solid (21 mg, 77%).

Representative Procedures for Entries 1-3, Table 2:

7-Bromo-1-(3,5-dimethoxybenzyl)-2,3-dihydro-1H-inden-1-ol. A solution of 7-bromo-2,3-dihydro-1H-inden-1-one (102 mg, 0.48 mmol) in 0.5 mL THF was added dropwise by cannula to a 0° C. solution of 3,5-dimethoxybenzylmagnesium bromide (3.8 mL, 0.95 mmol, 0.25 M/2-methyltetrahydrofuran, from Novel Chemical Solutions), rinsing with 0.5 mL THF. The reaction was stirred for 30 minutes at 0° C. and then was allowed to warm to room temperature. After 2 h, 30 mL saturated NH$_4$Cl solution was added and the resulting mixture was extracted with ethyl acetate (3×20 mL). The combined ethyl acetate solution was dried (Na$_2$SO$_4$), filtered and evaporated. Purification of the residue by flash chromatography on silica gel using a Combiflash unit by Teledyne Isco (ethyl acetate/hexanes) gave the title compound (145 mg, 83%).

4-Bromo-3-(3,5-dimethoxybenzyl)-1H-indene/(E)-7-bromo-1-(3,5-dimethoxybenzylidene)-2,3-dihydro-1H-indene Mixture. A mixture of 7-bromo-1-(3,5-dimethoxybenzyl)-2,3-dihydro-1H-inden-1-ol (145 mg, 0.40 mmol) and p-toluenesulfonic acid (12 mg, 0.063 mmol) in 1.8 mL toluene was heated to reflux for 1.5 h. The reaction was then allowed to cool to room temperature and evaporated. The residue was purified by flash chromatography on silica gel using a Combiflash unit by Teledyne Isco (ethyl acetate/hexanes) which gave the title compound (110 mg, 80%) as a mixture of the two alkene isomers in a 2:1 ratio (internal/external).

Methyl 4-(2-(3-(3,5-dimethoxybenzyl)-1H-inden-4-yl)ethyl)benzoate/(E)-methyl 4-(2-(3-(3,5-dimethoxybenzylidene)-2,3-dihydro-1H-inden-4-yl)ethyl)benzoate Mixture. A solution of methyl 4-vinyl benzoate (75 mg, 0.46 mmol) and 9-BBN dimer (108 mg, 0.44 mmol) in THF (1.3 mL) was stirred at room temperature for 4 h and then 110 µL $H_2O$ was added at 0° C. After 45 minutes at room temperature, the solution was cannula transferred to a mixture of 4-bromo-3-(3,5-dimethoxybenzyl)-1H-indene (110 mg, 0.32 mmol) and $PdCl_2(dppf) \cdot CH_2Cl_2$ (30 mg, 0.041 mmol) in 1.2 mL DMF. After 5 minutes, $K_3PO_4$ solution (170 µL, 3 M) was added and the dark mixture was stirred at 60° C. overnight. At this time, the mixture was allowed to cool to room temperature and then was partitioned between ethyl acetate/$H_2O$. The ethyl acetate layer was further washed with $H_2O$ (3×) and brine and then was dried ($Na_2SO_4$), filtered and evaporated. Purification of the residue by flash chromatography on silica gel using a Combiflash unit by Teledyne Isco (ethyl acetate/hexanes) gave slightly contaminated title compound (165 mg) as a 2:1 mixture of alkene isomers (internal/external).

Separation of the alkene isomers was accomplished at this stage (This was accomplished by Lotus Separations, Princeton, N.J.) using a Chiralpak AS-H column (2×25 cm, 15% MeOH/$CO_2$ 100 bar, 70 mL/min., 5 mg/mL MeOH, 1 mL injection volume) giving methyl 4-(2-(3-(3,5-dimethoxybenzyl)-1H-inden-4-yl)ethyl)benzoate (2.8 min.) and (E)-methyl 4-(2-(3-(3,5-dimethoxybenzylidene)-2,3-dihydro-1H-inden-4-yl)ethyl)benzoate (3.5 min.). Xray quality crystals of (E)-methyl 4-(2-(3-(3,5-dimethoxybenzylidene)-2,3-dihydro-1H-inden-4-yl)ethyl)benzoate were grown from hexanes and the structure was confirmed by xray crystallography.

4-(2-(3-(3,5-Dimethoxybenzyl)-1H-inden-4-yl)ethyl) benzoic Acid/(E)-4-(2-(3-(3,5-dimethoxybenzylidene)-2,3-dihydro-1H-inden-4-yl)ethyl)benzoic Acid Mixture. A mixture of methyl 4-(2-(3-(3,5-dimethoxybenzyl)-1H-inden-4-yl)ethyl)benzoate (48 mg, 0.11 mmol) and 1 M LiOH (0.60 mL, 0.60 mmol) in THF (6 mL) was stirred at 60° C. overnight. The mixture was then allowed to cool to room temperature and 10 mL 1 M HCl was added. The resulting mixture was extracted with $CH_2Cl_2$ (3×20 mL) and the combined organic solution was washed with brine and then was dried ($Na_2SO_4$), filtered and evaporated. Purification of the residue by flash chromatography on silica gel using a Combiflash unit by Teledyne Isco (ethyl acetate/hexanes) gave the title compounds (33 mg, 89% from 4-bromo-3-(3,5-dimethoxybenzyl)-1H-indene).

(E)-4-(2-(3-(3,5-dimethoxybenzylidene)-2,3-dihydro-1H-inden-4-yl)ethyl)benzoic Acid. The above procedure was followed using pure (E)-methyl 4-(2-(3-(3,5-dimethoxybenzylidene)-2,3-dihydro-1H-inden-4-yl)ethyl)benzoate. $^1$H NMR (300 MHz, $CDCL_3$) δ=8.04 (br. s., 2H), 7.38-7.30 (m, 2H), 7.26 (s, 1H), 7.21-7.12 (m, 2H), 7.01 (d, J=7.0 Hz, 1H), 6.91 (br. s., 1H), 6.55 (s, 2H), 6.38 (s, 1H), 3.82 (s, 6H), 3.32-3.22 (m, 2H), 3.15-2.98 (m, 6H).

4-(2-(3-(3,5-Dimethoxybenzyl)-2,3-dihydro-1H-inden-4-yl)ethyl)benzoic Acid. A mixture of 4-(2-(3-(3,5-dimethoxybenzyl)-1H-inden-4-yl)ethyl)benzoic acid/(E)-4-(2-(3-(3,5-dimethoxybenzylidene)-2,3-dihydro-1H-inden-4-yl)ethyl) benzoic acid (27 mg, 0.065 mmol) and 5% Pd/C (15 mg) in 1.4 mL ethyl acetate was evacuated and filled with $H_2$ (5×) and then was stirred at room temperature with a $H_2$ balloon overnight. The mixture was then filtered through Celite and evaporated to give the title compound (16 mg, 59%). $^1$H NMR (300 MHz, $CDCL_3$) δ=8.0 (d, J=7.6 Hz, 2H), 7.27 (d, J=7.6 Hz, 2H), 7.21-6.94 (m, 3H), 6.40-6.21 (m, 3H), 3.73 (s, 6H), 3.37 (br. s., 1H), 3.05-2.70 (m, 7H), 2.51 (dd, J=10.0, 13.5 Hz, 1H), 2.0-1.9 (m, 2H).

Representative Procedures for Entries 4-12, Table 2:

Methyl 4-(2-(3-oxo-2,3-dihydro-1H-inden-4-yl)ethyl)benzoate. A similar procedure as described above for methyl 4-(2-(3-(3,5-dimethoxybenzyl)-1H-inden-4-yl)ethyl)benzoate was followed using methyl 4-vinyl benzoate (500 mg, 3.08 mmol) and 9-BBN dimer (755 mg, 3.09 mmol) in THF (12 mL) followed by 7-bromo-2,3-dihydro-1H-inden-1-one (503 mg, 2.38 mmol), $PdCl_2(dppf) \cdot CH_2Cl_2$ (177 mg, 0.24 mmol) and 3 M $K_3PO_4$ solution (1.1 mL, 3.3 mmol) in 7.6 mL DMF. This gave the title compound (803 mg, >100%) which was used in the next step.

Methyl 4-(2-(3-(2,5-dimethoxybenzyl)-3-hydroxy-2,3-dihydro-1H-inden-4-yl)ethyl)benzoate. A solution of methyl 4-(2-(3-oxo-2,3-dihydro-1H-inden-4-yl)ethyl)benzoate (50 mg, 0.17 mmol) in 0.5 mL THF was added dropwise by cannula to an ice-cold solution of 2,5-dimethoxybenzylmagnesium chloride (1.4 mL. 0.35 mmol, 0.25 M/THF, Rieke), rinsing with 0.5 mL THF. The reaction was stirred for 30 minutes at 0° C. and for 2.5 h at room temperature. Saturated $NH_4Cl$ solution was then added and the resulting mixture was extracted with ethyl acetate (3×20 mL). The combined ethyl acetate solution was then dried ($Na_2SO_4$), filtered and evaporated. Purification of the residue by flash chromatography on silica gel using a Combiflash unit by Teledyne Isco (0% 40% ethyl acetate/hexanes) gave the title compound (45 mg, 59%).

Methyl 4-(2-(3-(2,5-dimethoxybenzyl)-1H-inden-4-yl)ethyl)benzoate/(E)-methyl 4-(2-(3-(2,5-dimethoxybenzylidene)-2,3-dihydro-1H-inden-4-yl)ethyl)benzoate. A similar procedure to that described for the synthesis of 4-bromo-3-(3,5-dimethoxybenzyl)-1H-indene was followed using methyl 4-(2-(3-(2,5-dimethoxybenzyl)-3-hydroxy-2,3-dihydro-1H-inden-4-yl)ethyl)benzoate (45 mg, 0.10 mmol) and p-toluenesulfonic acid (3 mg, 0.016 mmol) in 1 mL toluene. This gave the title compound (35 mg, 82%).

4-(2-(3-(2,5-Dimethoxybenzyl)-1H-inden-4-yl)ethyl) benzoic Acid/(E)-4-(2-(3-(2,5-dimethoxybenzylidene)-2,3-dihydro-1H-inden-4-yl)ethyl)benzoic Acid (Entry 5, Table 1). The procedure described for 4-(2-(3-(3,5-dimethoxybenzyl)-1H-inden-4-yl)ethyl)benzoic acid was followed using methyl 4-(2-(3-(2,5-dimethoxybenzyl)-1H-inden-4-yl)ethyl)benzoate (35 mg, 0.082 mmol) and 1 M LiOH (0.44 mL, 0.44 mmol) in 4.4 mL THF. This gave the title compound (16 mg, 47%). MS [m/e 413.18 (M-1)].

4-(2-(3-(3-Methoxybenzyl)-1H-inden-4-yl)ethyl)benzoic Acid/(E)-4-(2-(3-(3-methoxybenzylidene)-2,3-dihydro-1H-inden-4-yl)ethyl)benzoic Acid (Entry 6, Table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl)benzoic acid. MS [m/e 383.17 (M-1)].

4-(2-(3-(2,3-Dimethoxybenzyl)-1H-inden-4-yl)ethyl) benzoic Acid/(E)-4-(2-(3-(2,3-dimethoxybenzylidene)-2,3-dihydro-1H-inden-4-yl)ethyl)benzoic Acid (Entry 7, Table 1). The title compounds were synthesized as described above for 4-(2-(3-(2,5-Dimethoxybenzyl)-1H-inden-4-yl) ethyl)benzoic acid/(E)-4-(2-(3-(2,5-dimethoxybenzylidene)-2,3-dihydro-1H-inden-4-yl)ethyl)benzoic acid. MS [m/e 413.18 (M-1)].

4-(2-(3-(3,4-Dimethoxybenzyl)-1H-inden-4-yl)ethyl)benzoic Acid/(E)-4-(2-(3-(3,4-dimethoxybenzylidene)-2,3-dihydro-1H-inden-4-yl)ethyl)benzoic Acid (Entry 8, Table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl)benzoic acid. MS [m/e 413.17 (M-1)].

4-(2-(3-(2-Methoxybenzyl)-1H-inden-4-yl)ethyl)benzoic Acid/(E)-4-(2-(3-(2-methoxybenzylidene)-2,3-dihydro-1H-inden-4-yl)ethyl)benzoic Acid (Entry 9, Table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl)benzoic acid. MS [m/e 383.16 (M-1)].

4-(2-(3-(4-Methoxybenzyl)-1H-inden-4-yl)ethyl)benzoic Acid/(E)-4-(2-(3-(4-methoxybenzylidene)-2,3-dihydro-1H-inden-4-yl)ethyl)benzoic Acid (Entry 10, Table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl)benzoic acid. MS [m/e 383.16 (M-1)].

4-(2-(3-(3,5-Dichlorobenzyl)-1H-inden-4-yl)ethyl)benzoic Acid/(E)-4-(2-(3-(3,5-dichlorobenzylidene)-2,3-dihydro-1H-inden-4-yl)ethyl)benzoic Acid (Entry 11, Table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl)benzoic acid. MS [m/e 421.07 (M-1)].

4-(2-(3-(3,5-Dimethylbenzyl)-1H-inden-4-yl)ethyl)benzoic Acid/(E)-4-(2-(3-(3,5-dimethylbenzylidene)-2,3-dihydro-1H-inden-4-yl)ethyl)benzoic Acid (Entry 12, Table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl)benzoic acid. MS [m/e 381.18 (M-1)].

4-(2-(3-(3,5-Dimethoxybenzyl)-7-fluoro-1H-inden-4-yl)ethyl)benzoic Acid/(E)-4-(2-(3-(3,5-dimethoxybenzylidene)-7-fluoro-2,3-dihydro-1H-inden-4-yl)ethyl)benzoic Acid (Entry 13, table 1). The title compounds were synthesized as described above for 4-(2-(3-(2,5-Dimethoxybenzyl)-1H-inden-4-yl)ethyl)benzoic acid/(E)-4-(2-(3-(2,5-dimethoxybenzylidene)-2,3-dihydro-1H-inden-4-yl)ethyl) benzoic acid. MS [m/e 431.17 (M-1)].

Representative Procedures for Entries 13-14, Table 2:

7-((tert-Butyldimethylsilyl)oxy)-2,3-dihydro-1H-inden-1-one. A solution of 7-hydroxy-2,3-dihydro-1H-inden-1-one (0.501 g, 3.38 mmol), tert-butyldimethylsilylchloride (1.033 g, 6.85 mmol), triethylamine (0.62 mL, 4.45 mmol) and 4-dimethylaminopyridine (DMAP, 232 mg, 1.90 mmol) in $CH_2Cl_2$ (10 mL) was stirred at room temperature overnight. The reaction was then treated with 40 mL saturated $NH_4Cl$ solution and the resulting mixture was extracted with $CH_2Cl_2$ (3×20 mL). The combined $CH_2Cl_2$ solution was dried ($Na_2SO_4$), filtered and evaporated. Purification of the residue by flash chromatography on silica gel using a Combiflash unit by Teledyne Isco (ethyl acetate/hexanes) gave the title compound (1.014 g, >100%).

7-((tert-Butyldimethylsilyl)oxy)-1-(3,5-dimethoxybenzyl)-2,3-dihydro-1H-inden-1-ol. A procedure similar to that described for 7-bromo-1-(3,5-dimethoxybenzyl)-2,3-dihydro-1H-inden-1-ol was followed using 7-((tert-butyldimethylsilyl)oxy)-2,3-dihydro-1H-inden-1-one (260 mg, 0.99 mmol) and 3,5-dimethoxybenzylmagnesium bromide (7.6 mL, 1.90 mmol, 0.25 M/2-methyltetrahydrofuran, from Rieke) in 2 mL THF. This gave the title compound (266 mg, 65%).

(E)-tert-Butyl((3-(3,5-dimethoxybenzylidene)-2,3-dihydro-1H-inden-4-yl)oxy)dimethylsilane/tert-butyl((3-(3,5-dimethoxybenzyl)-1H-inden-4-yl)oxy)dimethylsilane. A procedure similar to that described for 4-bromo-3-(3,5-dimethoxybenzyl)-1H-indene was followed using 7-((tert-butyldimethylsilyl)oxy)-1-(3,5-dimethoxybenzyl)-2,3-dihydro-1H-inden-1-ol (266 mg, 0.64 mmol) and p-toluenesulfonic acid (26 mg, 0.14 mmol) in 3 mL toluene. This gave the title compounds (136 mg, 53%) as a 4:1 mixture favoring (E)-tert-butyl((3-(3,5-dimethoxybenzylidene)-2,3-dihydro-1H-inden-4-yl)oxy)dimethylsilane.

(E)-3-(3,5-Dimethoxybenzylidene)-2,3-dihydro-1H-inden-4-ol/3-(3,5-Dimethoxybenzyl)-1H-inden-4-ol. A solution of tert-butyl((3-(3,5-dimethoxybenzyl)-1H-inden-4-yl)oxy)dimethylsilane (136 mg, 0.34 mmol) and tetrabutylammonium fluoride (TBAF, 1.3 mL, 1.3 mmol, 1 M/THF) in THF (13 mL) was stirred at room temperature. After 1.5 h, 40 mL saturated $NH_4Cl$ solution was added and the resulting mixture was extracted with ethyl acetate (3×60 mL). The combined ethyl acetate solution was then dried ($Na_2SO_4$), filtered and evaporated. Purification of the residue by flash chromatography on silica gel using a Combiflash unit by Teledyne Isco (ethyl acetate/hexanes) gave the title compounds (73 mg, 76%) with the mixture being predominately (E)-3-(3,5-dimethoxybenzylidene)-2,3-dihydro-1H-inden-4-ol, with only a trace of the internal alkene isomer.

(E)-methyl 4-(((3-(3,5-dimethoxybenzylidene)-2,3-dihydro-1H-inden-4-yl)oxy)methyl)benzoate. A mixture of 3-(3,5-dimethoxybenzyl)-1H-inden-4-ol (73 mg, 0.26 mmol), methyl 4-(bromomethyl)benzoate (75 mg, 0.33 mmol) and $K_2CO_3$ (55 mg, 0.40 mmol) in DMF (1 mL) was stirred at room temperature overnight. The mixture was then partitioned between ethyl acetate/$H_2O$ and the organic layer was further washed with $H_2O$ (2×) and brine. The ethyl acetate solution was then dried ($Na_2SO_4$), filtered and evaporated. Purification of the residue by flash chromatography on silica gel using a Combiflash unit by Teledyne Isco (ethyl acetate/hexanes) gave the title compound as a single alkene isomer (79 mg, 71%).

(E)-4-(((3-(3,5-dimethoxybenzylidene)-2,3-dihydro-1H-inden-4-yl)oxy)methyl)benzoic acid. The procedure described for 4-(2-(3-(3,5-dimethoxybenzyl)-1H-inden-4-yl)ethyl)benzoic acid was followed using methyl 4-(((3-(3,5-dimethoxybenzyl)-1H-inden-4-yl)oxy)methyl)benzoate (41 mg, 0.096 mmol) and 1 M LiOH (0.52 mL, 0.52 mmol) in 5.2 mL THF. This gave the title compound (39 mg, 97%). $^1$H NMR (300 MHz, $d_6$-DMSO) δ=8.01-7.98 (d, 2H), 7.67-7.64 (m, 2H), 7.49 (s, 1H), 7.29-7.09 (m, 1H), 6.95-6.93 (m, 2H), 6.45 (s, 2H), 6.35 (s, 1H), 5.32 (s, 2H), 3.72 (s, 6H), 3.02 (s, 4H).

Methyl 4-(((3-(3,5-dimethoxybenzyl)-2,3-dihydro-1H-inden-4-yl)oxy)methyl)benzoate. A similar procedure to that described for 4-(2-(3-(3,5-dimethoxybenzyl)-2,3-dihydro-1H-inden-4-yl)ethyl)benzoic acid was followed using methyl 4-(((3-(3,5-dimethoxybenzyl)-1H-inden-4-yl)oxy)methyl)benzoate (38 mg, 0.088 mmol) and 5% Pd/C (22 mg) in 4 mL ethyl acetate. Purification of the crude product by flash chromatography on silica gel using a Combiflash unit by Teledyne Isco (ethyl acetate/hexanes) gave the title compound (19 mg, 50%).

4-(((3-(3,5-Dimethoxybenzyl)-2,3-dihydro-1H-inden-4-yl)oxy)methyl)benzoic acid. The procedure described for 4-(2-(3-(3,5-dimethoxybenzyl)-1H-inden-4-yl)ethyl)benzoic acid was followed using methyl 4-(((3-(3,5-dimethoxybenzyl)-2,3-dihydro-1H-inden-4-yl)oxy)methyl)benzoate (19 mg, 0.044 mmol) and 1 M LiOH (0.24 mL, 0.24 mmol) in 2.4 mL THF. This gave the title compound (13 mg, 71%). $^1$H NMR (300 MHz, CDCl$_3$) δ=8.14-8.12 (m, 2H), 7.59-7.56 (d, J=6.7 Hz, 2H), 7.13-7.10 (t, J=7.6 Hz, 1H), 6.86-6.84 (d, J=7.3 Hz, 1H), 6.73-6.70 (d, J=8.2 Hz, 1H), 6.30 (br. s., 3H), 5.18 (s, 2H), 3.71 (s, 6H), 3.7-3.6 (br s, 1H), 3.24-3.18 (dd, J=3.5, 13.5 Hz, 1H), 2.93-2.72 (m, 2H), 2.54 (dd, J=10.3, 12.9 Hz, 1H), 2.13-1.88 (m, 2H)

Representative Procedures for Entries 15-19, Table 2:

Methyl 4-(2-(3-(((trifluoromethyl)sulfonyl)oxy)-1H-inden-4-yl)ethyl)benzoate. Triflic anhydride (170 μL, 1.0 mmol) was added to a solution of methyl 4-(2-(3-oxo-2,3-dihydro-1H-inden-4-yl)ethyl)benzoate (281 mg, 0.96 mmol) in 1,2-dichloroethane (2.2 mL). After 5 min., 2,6-di-tert-butyl-4-methylpyridine (140 μL, 1.0 mmol) was added. The reaction was stirred at room temperature for 1 h and then was quenched by addition of 10 mL 1 M HCl. The mixture was extracted with dichloromethane and the organic layer washed with 30 mL 1 M HCl and brine. The organic solution was then dried (Na$_2$SO$_4$), filtered and evaporated. Purification of the crude product by flash chromatography on silica gel using a Combiflash unit by Teledyne Isco (ethyl acetate/hexanes) gave the title compound (251 mg, 61%).

Methyl 4-(2-(3-(3,5-difluorobenzyl)-1H-inden-4-yl)ethyl)benzoate. 3,5-Difluorozinc chloride (0.9 mL, 0.45 mmol, 0.5 M/THF, Rieke) was added to a mixture of methyl 44243-(((trifluoromethyl)sulfonyl)oxy)-1H-inden-4-yl)ethyl)benzoate (55 mg, 0.13 mmol) and (Ph$_3$P)$_4$Pd (24 mg, 0.02 mmol) in 0.65 mL THF. The mixture was heated at 70° C. overnight. The reaction was allowed to cool to room temperature and saturated NH$_4$Cl solution was added. The mixture was extracted with ethyl acetate and the organic solution was dried (Na$_2$SO$_4$), filtered and evaporated. Purification of the crude product by flash chromatography on silica gel using a Combiflash unit by Teledyne Isco (ethyl acetate/hexanes) gave the title compound (10 mg, 19%).

4-(2-(3-(3,5-difluorobenzyl)-1H-inden-4-yl)ethyl)benzoic Acid (Entry 18, Table 1). The procedure described for 4-(2-(3-(3,5-dimethoxybenzyl)-1H-inden-4-yl)ethyl)benzoic acid was followed using methyl 4-(2-(3-(3,5-difluorobenzyl)-1H-inden-4-yl)ethyl)benzoate (10 mg, 0.025 mmol) and 1 M LiOH (0.1 mL, 0.1 mmol) in 1 mL THF. This gave the title compound (5 mg, 51%, MS m/e=389.13, M-1).

4-(2-(3-(3,5-Dimethoxybenzyl)-1H-inden-4-yl)ethyl) benzoic Acid (Entry 15, Table 1). The sequence described for 4-(2-(3-(3,5-difluorobenzyl)-1H-inden-4-yl)ethyl)benzoic acid was followed. $^1$H NMR (300 MHz, CDCl$_3$) δ=7.93 (d, J=7.6 Hz, 2H), 7.34 (d, J=7.3 Hz, 1H), 7.15 (d, J=8.8 Hz, 3H), 7.06-7.01 (m, 1H), 6.31 (s, 3H), 6.15 (s, 1H), 3.99 (s, 2H), 3.91 (s, 3H), 3.70 (s, 6H), 3.34 (s, 2H), 3.11-3.04 (m, 2H), 2.93-2.85 (m, 2H).

4-(2-(3-(3,5-Bis(trifluoromethyl)benzyl)-1H-inden-4-yl) ethyl)benzoic Acid (Entry 17, Table 1). The sequence described for 4-(2-(3-(3,5-difluorobenzyl)-1H-inden-4-yl)ethyl)benzoic acid was followed. MS [m/e 489.1209 (M-1)].

4-(2-(3-(3,5-Dimethoxybenzyl)-5-methoxy-1H-inden-4-yl)ethyl)benzoic Acid (Entry 16, Table 1). The sequence described for 4-(2-(3-(3,5-difluorobenzyl)-1H-inden-4-yl)ethyl)benzoic acid was followed. MS [m/e 443.1899 (M-1)].

4-(2-(3-(3,5-Dimethoxybenzyl)-6-fluoro-1H-inden-4-yl) ethyl)benzoic Acid (Entry 19, Table 1)

The sequence described for 4-(2-(3-(3,5-difluorobenzyl)-1H-inden-4-yl)ethyl)benzoic acid was followed. MS [m/e 431.1686 (M-1)].

Representative Procedure for Entry 20, Table 2:

(E)-ethyl 3-(3-(3-oxo-2,3-dihydro-1H-inden-4-yl)phenyl) acrylate. A mixture of 7-bromo-2,3-dihydro-1H-inden-1-one (100 mg, 0.48 mmol), (E)-(3-(3-ethoxy-3-oxoprop-1-en-1-yl)phenyl)boronic acid (210 mg, 0.95 mmol), and K$_2$CO$_3$ (133 mg, 0.96 mmol) in toluene (66 mL)/EtOH (22 mL) was purged with N$_2$. (Ph$_3$P)$_4$Pd (55 mg, 0.048 mmol) was added and the mixture was heated in a sealed tube at 80° C. overnight. The mixture was allowed to cool to room temperature and the volume was reduced in half H$_2$O (100 mL) was added and the resulting mixture was extracted with ethyl acetate (3×40 mL). The combined organic solution was washed with brine and then was dried (Na$_2$SO$_4$), filtered and evaporated. Purification of the crude product by flash chromatography on silica gel using a Combiflash unit by Teledyne Isco (ethyl acetate/hexanes) gave the title compound (133 mg, 90%).

(E)-ethyl 3-(3-(3-(((trifluoromethyl)sulfonyl)oxy)-1H-inden-4-yl)phenyl)acrylate. A similar procedure to that described for methyl 4-(2-(3-(((trifluoromethyl)sulfonyl) oxy)-1H-inden-4-yl)ethyl)benzoate was followed.

(E)-ethyl 3-(3-(3-(3,5-dimethoxybenzyl)-1H-inden-4-yl) phenyl)acrylate. An analogous procedure to that described for methyl 4-(2-(3-(3,5-difluorobenzyl)-1H-inden-4-yl) ethyl)benzoate was followed.

(E)-3-(3-(3-(3,5-dimethoxybenzyl)-1H-inden-4-yl)phenyl)acrylic Acid. The procedure described for 4-(2-(3-(3,5-dimethoxybenzyl)-1H-inden-4-yl)ethyl)benzoic acid was followed. MS [m/e 411.15 (M-1)].

Representative Procedure for Entry 21, Table 2:

Methyl 4-((3-oxo-2,3-dihydro-1H-inden-4-yl)ethynyl) benzoate. A mixture of 7-bromo-2,3-dihydro-1H-inden-1-one (411 mg, 1.95 mmol), methyl 4-ethynylbenzoate (361 mg, 2.25 mmol), Pd(CH$_3$CN)$_2$Cl$_2$ (50 mg, 0.19 mmol), Cs$_2$CO$_3$ (1.220 g, 3.75 mmol) and X-phos (180 mg, 0.38 mmol) in 5 mL CH$_3$CN was heated to 80° C. overnight in a sealed tube. The mixture was then allowed to cool to room temperature, H$_2$O was added and the resulting mixture was extracted with ethyl acetate (3×). The combined ethyl acetate solution was washed with brine and then was dried (Na$_2$SO$_4$), filtered and evaporated. Purification of the crude product by flash chromatography on silica gel using a Combiflash unit by Teledyne Isco (ethyl acetate/hexanes) gave the title compound (147 mg, 26%).

(E)-Methyl 4-(2-(3-oxo-2,3-dihydro-1H-inden-4-yl)vinyl)benzoate. Formic acid (180 μL, 0.98 mmol, 25% aqueous solution) was added to a Schlenk tube containing Pd$_2$(dba)$_3$ (7 mg, 0.008 mmol), 1,4-Bis(diphenylphosphino) butane (7 mg, 0.015 mmol), methyl 4-((3-oxo-2,3-dihydro-1H-inden-4-yl)ethynyl)benzoate (98 mg, 0.34 mmol), THF (1.5 mL) and dichloromethane (1 mL). The tube was sealed under N$_2$ and was heated at 80° C. overnight. The mixture was allowed to cool to room temperature and was diluted with dichloromethane. The resulting mixture was dried (Na$_2$SO$_4$), filtered and evaporated. Purification of the crude product by flash chromatography on silica gel using a Combiflash unit by Teledyne Isco (ethyl acetate/hexanes) gave the title compound (58 mg, 58%).

(E)-Methyl 4-(2-(3-(((trifluoromethyl)sulfonyl)oxy)-1H-inden-4-yl)vinyl)benzoate. A similar procedure to that described for methyl 4-(2-(3- (((trifluoromethyl)sulfonyl) oxy)-1H-inden-4-yl)ethyl)benzoate was followed.

(E)-Methyl 4-(2-(3-(3,5-dimethoxybenzyl)-1H-inden-4-yl)vinyl)benzoate. An analogous procedure to that described for methyl 4-(2-(3-(3,5-difluorobenzyl)-1H-inden-4-yl) ethyl)benzoate was followed.

(E)-4-(2-(3-(3,5-dimethoxybenzyl)-1H-inden-4-yl)vinyl) benzoic Acid. The procedure described for 4-(2-(3-(3,5-dimethoxybenzyl)-1H-inden-4-yl)ethyl)benzoic acid was followed. MS [m/e 411.1595 (M-1)].

Representative Procedures for Entries 22 and 23, Table 2:

Ethyl 2-(4-(3-(3-oxo-2,3-dihydro-1H-inden-4-yl)phenoxy) acetate. The procedure described for (E)-ethyl 3-(3-(3-oxo-2,3-dihydro-1H-inden-4-yl)phenyl)acrylate was followed.

Ethyl 2-(4-(3-(((trifluoromethyl)sulfonyl)oxy)-1H-inden-4-yl)phenoxy)acetate. A similar procedure to that described for methyl 4-(2-(3-(((trifluoromethyl)sulfonyl)oxy)-1H-inden-4-yl)ethyl)benzoate was followed.

Ethyl 2-(4-(3-(3,5-dimethoxybenzyl)-1H-inden-4-yl)phenoxy)acetate. An analogous procedure to that described for methyl 4-(2-(3-(3,5-difluorobenzyl)-1H-inden-4-yl)ethyl) benzoate was followed.

2-(4-(3-(3,5-Dimethoxybenzyl)-1H-inden-4-yl)phenoxy) acetic Acid. The procedure described for 4-(2-(3-(3,5-dimethoxybenzyl)-1H-inden-4-yl)ethyl)benzoic acid was followed at room temperature. MS [m/e 415.1551 (M-1)].

2-(3-(3-(3,5-Dimethoxybenzyl)-1H-inden-4-yl)phenoxy) acetic Acid. A similar sequence to that described for 2-(4-(3-(3,5-Dimethoxybenzyl)-1H-inden-4-yl)phenoxy)acetic acid (scheme 7) was used. MS [m/e 415.15 (M-1)].

Representative Procedure for Entry 24, Table 2:

Methyl 4-((3-(3,5-dimethoxybenzyl)-3-hydroxy-2,3-dihydro-1H-inden-4-yl)ethynyl)benzoate. A similar procedure to that described for methyl 4-(2-(3-(2,5-dimethoxybenzyl) 3-hydroxy-2,3-dihydro-1H-inden-4-yl)ethyl)benzoate was followed using methyl 4-((3-oxo-2,3-dihydro-1H-inden-4-yl)ethynyl)benzoate (preparation described above) and 3,5-dimethoxybenzylmagnesium bromide.

Methyl 4-((3-(3,5-dimethoxybenzyl)-1H-inden-4-yl) ethynyl)benzoate/(E)-methyl 4-((3-(3,5-dimethoxybenzylidene)-2,3-dihydro-1H-inden-4-yl)ethynyl)benzoate. A similar procedure to that described for the synthesis of 4-bromo-3-(3,5-dimethoxybenzyl)-1H-indene was followed.

4-((3-(3,5-Dimethoxybenzyl)-1H-inden-4-yl)ethynyl) benzoic Acid/(E)-4-((3-(3,5-dimethoxybenzylidene)-2,3-dihydro-1H-inden-4-yl)ethynyl)benzoic Acid. The procedure described for 4-(2-(3-(3,5-dimethoxybenzyl)-1H-inden-4-yl)ethyl)benzoic acid was followed. MS [m/e 409.1499 (M-1)].

Binding Data (Ki)

Competition binding experiments were performed in a medium containing Hank's balanced salt solution, Hepes 20 mM, pH 7.3, membranes (~60 µg protein) or $2 \times 10^5$ cells from HEK 293 cells stably expressing human EP2 receptors, [$^3$H]PGE2 (10 nM) and various concentrations of test compounds in a total volume of 300 µl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 µM). Binding data fitted to the binding model for a single class of binding sites, using nonlinear regression analysis. $IC_{50}$ values thus obtained were converted to Ki using the equation of Ki= $(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H—] $PGE_2$ (specific activity 180 Ci mmol) was used as the radioligand for EP receptors. [$^3$H] 17-phenyl $PGF_{2\alpha}$ was employed for FP receptor binding studies. Binding studies employing $EP_1$, $EP_2$, $EP_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 g/ml geneticin (G418) and 200 mg/ml hygromycin B as selection markers, and 100 units/ml penicillin G, 100 g/ml streptomycin and 0.25 mg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 mM, plates were washed four times with HBSS-HEPES buffer to remove excess dye leaving 100 ml in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

TABLE 1

| Entry | STRUCTURE | EP2 cAMP EC50 (nM) | EP2 Ki (nM) | EP4 cAMP EC50 (nM) | EP4 Ki EC50 (nM) | OTHER RECEPTORS FLIPR EC50 (nM) |
|---|---|---|---|---|---|---|
| 1 | | 35 | 38 | 123 | 897 | NA: DP, EP1, EP3, FP, IP, TP |
| 2 | | 29 | 14 | 450 | 616 | |
| 3 | | 12 | 12 | 205 | 412 | NA: DP, EP1, EP3, FP, IP, TP |
| 4 | | 11 | 0.3 | | 1203 | |

TABLE 1-continued

| Entry | STRUCTURE | EP2 cAMP EC50 (nM) | EP2 Ki (nM) | EP4 cAMP EC50 (nM) | EP4 Ki EC50 (nM) | OTHER RECEPTORS FLIPR EC50 (nM) |
|---|---|---|---|---|---|---|
| 5 | | 13 | 15 | 3 | 19 | NA: DP, EP1, EP3, FP, IP, TP |
| 6 | | | | 174 | | |
| 7 | | | | 5847 | | |
| 8 | | | | 453 | | |

TABLE 1-continued

| Entry | STRUCTURE | EP2 cAMP EC50 (nM) | EP2 Ki (nM) | EP4 cAMP EC50 (nM) | EP4 Ki EC50 (nM) | OTHER RECEPTORS FLIPR EC50 (nM) |
|---|---|---|---|---|---|---|
| 9 | 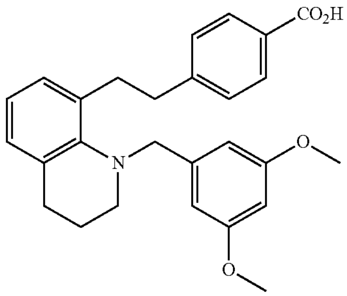 [SMILES: COc1cc(CN2CCCc3cccc(CCc4ccc(C(=O)O)cc4)c32)cc(OC)c1] | | | | 453 | |
| 10 | 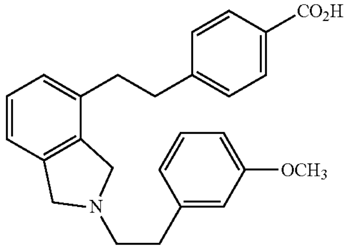 [SMILES: COc1cccc(CCN2Cc3cccc(CCc4ccc(C(=O)O)cc4)c3C2)c1] | 1128 | >10K | >10K | | |
| 11 | 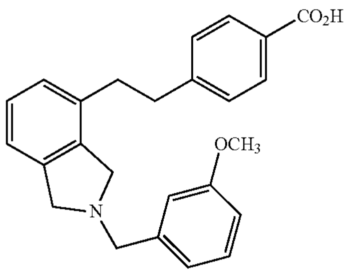 [SMILES: COc1cccc(CN2Cc3cccc(CCc4ccc(C(=O)O)cc4)c3C2)c1] | 6880 | >10K | 9561 | | |
| 12 | 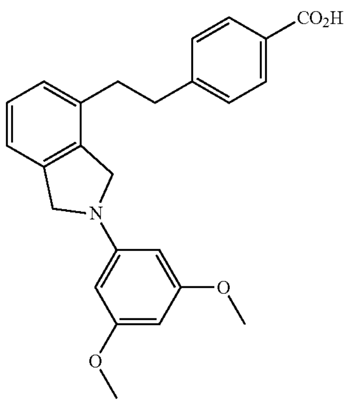 [SMILES: COc1cc(OC)cc(N2Cc3cccc(CCc4ccc(C(=O)O)cc4)c3C2)c1] | | | | 3905 | |
| 13 | 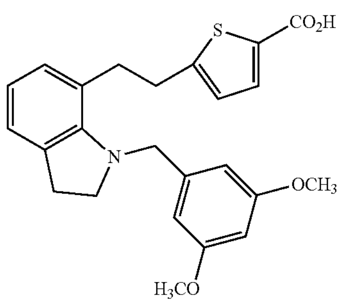 [SMILES: COc1cc(CN2CCc3cccc(CCc4ccc(C(=O)O)s4)c32)cc(OC)c1] | | | 47 | 161 | |

TABLE 1-continued

| Entry | STRUCTURE | EP2 cAMP EC50 (nM) | EP2 Ki (nM) | EP4 cAMP EC50 (nM) | EP4 Ki EC50 (nM) | OTHER RECEPTORS FLIPR EC50 (nM) |
|---|---|---|---|---|---|---|
| 14 | 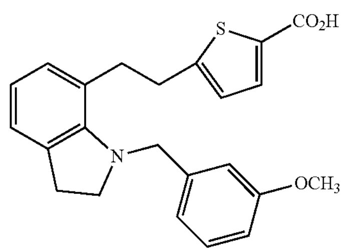 [SMILES: COc1cccc(CN2CCc3cccc(CCc4ccc(C(=O)O)s4)c32)c1] | 50 | | 714 | | |
| 15 | 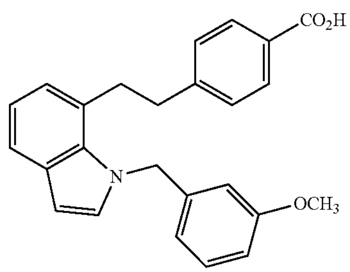 [SMILES: COc1cccc(Cn2ccc3cccc(CCc4ccc(C(=O)O)cc4)c32)c1] | 259 | | 1619, 3127 | 1682 | |
| 16 | 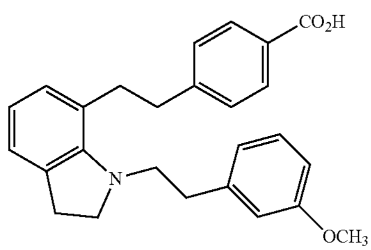 [SMILES: COc1cccc(CCN2CCc3cccc(CCc4ccc(C(=O)O)cc4)c32)c1] | 41 | | 1257 | 373 | |
| 17 | 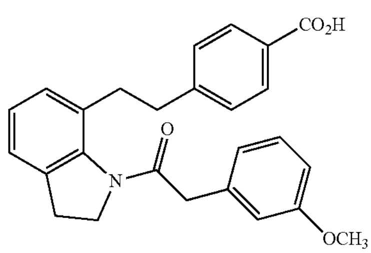 [SMILES: COc1cccc(CC(=O)N2CCc3cccc(CCc4ccc(C(=O)O)cc4)c32)c1] | >10K | | >10K | 449 | |
| 18 | 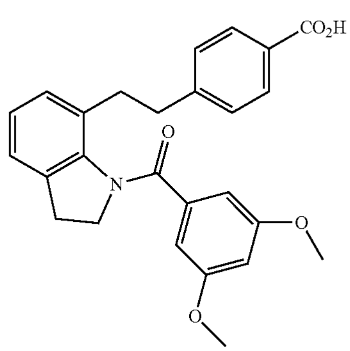 [SMILES: COc1cc(OC)cc(C(=O)N2CCc3cccc(CCc4ccc(C(=O)O)cc4)c32)c1] | 183 | | 821 | 4855 | |

TABLE 1-continued
| Entry | STRUCTURE | EP2 cAMP EC50 (nM) | EP2 Ki (nM) | EP4 cAMP EC50 (nM) | EP4 Ki EC50 (nM) | OTHER RECEPTORS FLIPR EC50 (nM) |
|---|---|---|---|---|---|---|
| 19 | 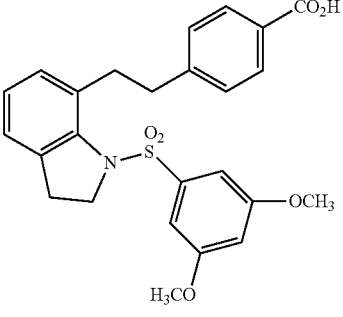 [SMILES: COc1cc(OC)cc(S(=O)(=O)N2CCc3cccc(CCc4ccc(C(=O)O)cc4)c32)c1] | 776 | >10K | 8234 | | |
| 20 | 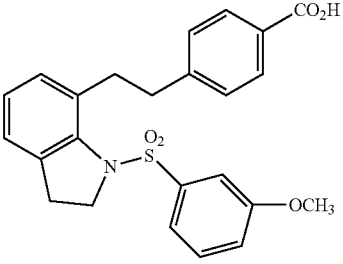 [SMILES: COc1cccc(S(=O)(=O)N2CCc3cccc(CCc4ccc(C(=O)O)cc4)c32)c1] | 571 | >10K | >10K | | |
| 21 | 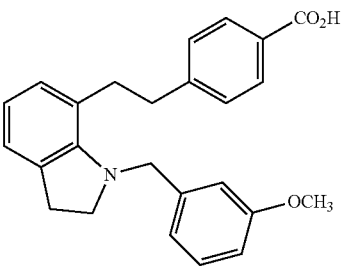 [SMILES: COc1cccc(CN2CCc3cccc(CCc4ccc(C(=O)O)cc4)c32)c1] | 23 | 178 | 123 | | |
| 22 | 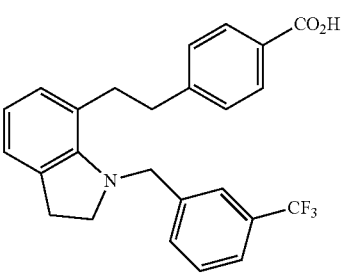 [SMILES: O=C(O)c1ccc(CCc2cccc3c2N(Cc2cccc(C(F)(F)F)c2)CC3)cc1] | 15 | 7 | 187 | 424 | NA: DP, EP1, EP3, FP, IP, TP |
| 23 | 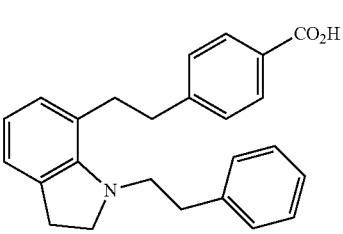 [SMILES: O=C(O)c1ccc(CCc2cccc3c2N(CCc2ccccc2)CC3)cc1] | 202 | 1582 | 1092 | | |

TABLE 1-continued

| | | EP2 | | EP4 | | |
| --- | --- | --- | --- | --- | --- | --- |
| | | cAMP EC50 (nM) | Ki (nM) | cAMP EC50 (nM) | Ki EC50 (nM) | OTHER RECEPTORS FLIPR EC50 (nM) |
| Entry | STRUCTURE | | | | | |
| 24 | *structure* | | 14 | 2 | 2 | |

TABLE 2

| Entry | STRUCTURE | cAMP EC50 (nM) | Ki (nM) | cAMP EC50 (nM) | Ki EC50 (nM) | FLIPR EC50 (nM) |
| --- | --- | --- | --- | --- | --- | --- |
| 1 | *structure* | | 2 | 7.2 | 3 | |
| 2 | *structure* | 28 | 95 | 7 | 42 | |
| 3 | *structure* | 130 | 116 | 43 | 90 | NA: EP1, EP3, DP, FP, IP, TP |

TABLE 2-continued

| Entry | STRUCTURE | cAMP EC50 (nM) | Ki (nM) | cAMP EC50 (nM) | Ki EC50 (nM) | FLIPR EC50 (nM) |
|---|---|---|---|---|---|---|
| 4 | 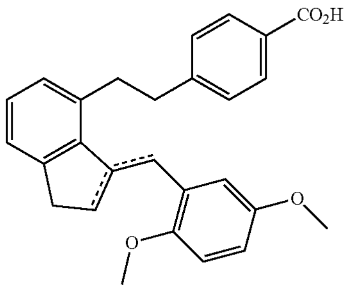 | | 61 | 71 | 52 | |
| 5 | 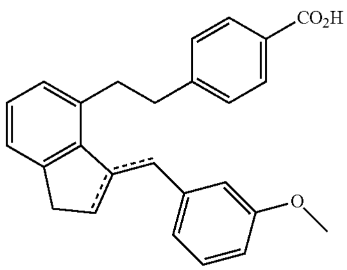 | 11 | 2 | 41 | 6 | NA: DP, EP1, EP3, FP. IP, TP |
| 6 | 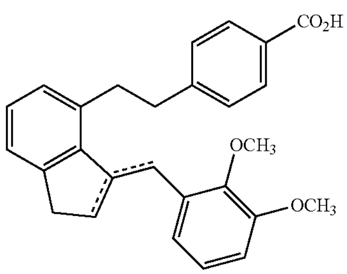 | | 53 | 562 | 251 | |
| 7 | 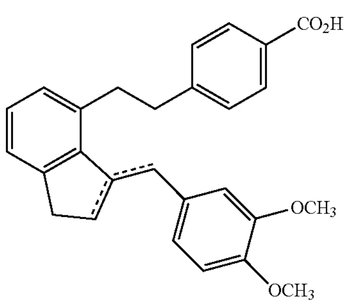 | 161 | 20 | 33 | 34 | NA: EP1, EP3, DP, FP, IP, TP |
| 8 | 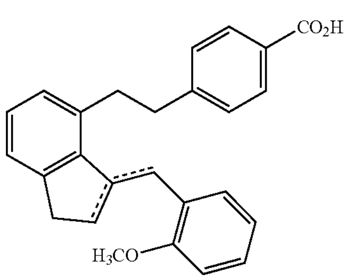 | 57 | 67 | 107 | 71 | NA: EP1, EP3, DP, FP, IP, TP |

TABLE 2-continued
| Entry | STRUCTURE | cAMP EC50 (nM) | Ki (nM) | cAMP EC50 (nM) | Ki EC50 (nM) | FLIPR EC50 (nM) |
|---|---|---|---|---|---|---|
| 9 | 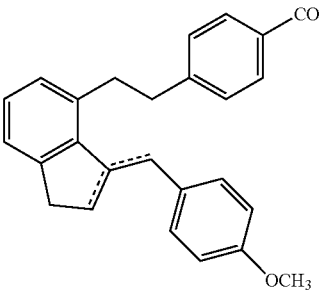 | 114 | 27 | 93 | 195 | NA: EP1, EP3, DP, FP, IP, TP |
| 10 | 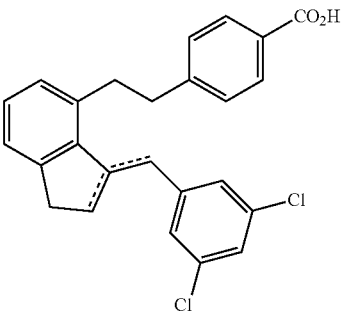 | 2 | 18 | 23 | 56 | |
| 11 | 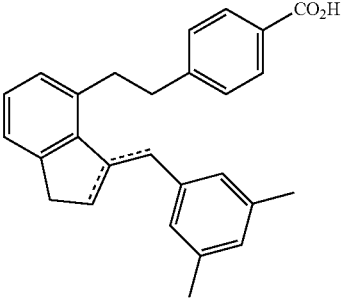 | 13 | 6 | 220 | 240 | NA: EP1, EP3, DP, FP, IP, TP |
| 12 | 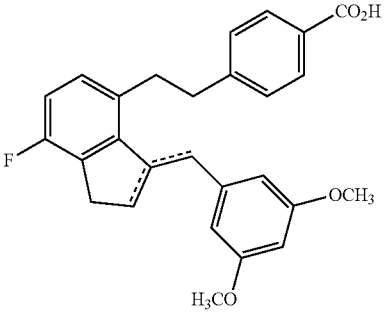 | 25 | 83 | 41 | 52 | NA: EP1, EP3, DP, FP, IP, TP |

TABLE 2-continued

| Entry | STRUCTURE | cAMP EC50 (nM) | Ki (nM) | cAMP EC50 (nM) | Ki EC50 (nM) | FLIPR EC50 (nM) |
|---|---|---|---|---|---|---|
| 13 | 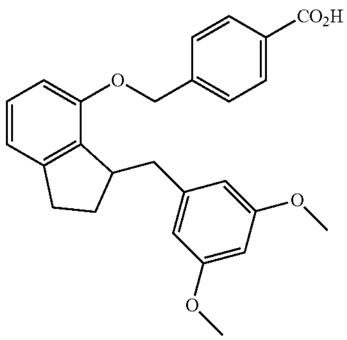 [SMILES: COc1cc(CC2CCc3cccc(OCc4ccc(C(=O)O)cc4)c32)cc(OC)c1] | 469 | 16 | 154 | | |
| 14 | 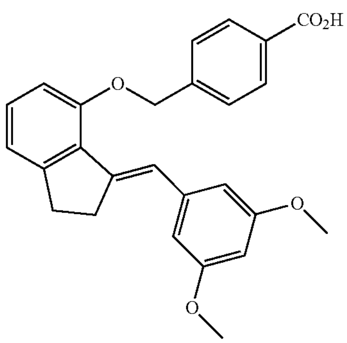 [SMILES: COc1cc(/C=C2\CCc3cccc(OCc4ccc(C(=O)O)cc4)c32)cc(OC)c1] | >10K | >10K | 1486 | | |
| 15 | 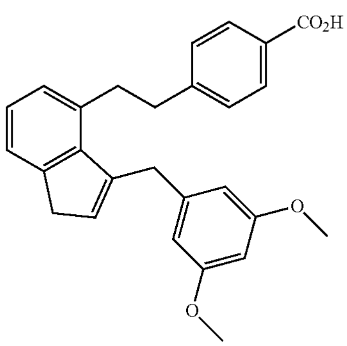 [SMILES: COc1cc(CC2=CCc3cccc(CCc4ccc(C(=O)O)cc4)c32)cc(OC)c1] | 11 | 3(2) | 1(7) | 0.8 (5) | NA: EP1, EP3, DP, FP, IP, TP |
| 16 | 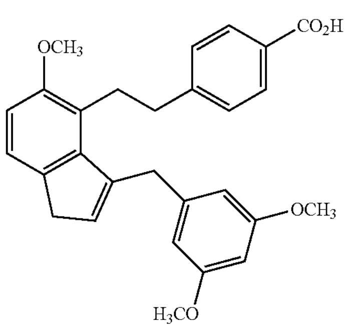 [SMILES: COc1cc(CC2=CCc3ccc(OC)c(CCc4ccc(C(=O)O)cc4)c32)cc(OC)c1] | 1698 | 469 | | | |

TABLE 2-continued

| Entry | STRUCTURE | cAMP EC50 (nM) | Ki (nM) | cAMP EC50 (nM) | Ki EC50 (nM) | FLIPR EC50 (nM) |
|---|---|---|---|---|---|---|
| 17 | 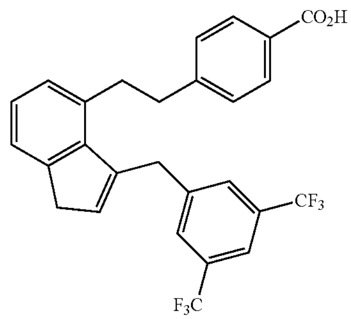 [SMILES: O=C(O)c1ccc(CCc2cccc3c2C(Cc2cc(C(F)(F)F)cc(C(F)(F)F)c2)=CC3)cc1] | | 8 | 296 | 736 | |
| 18 | 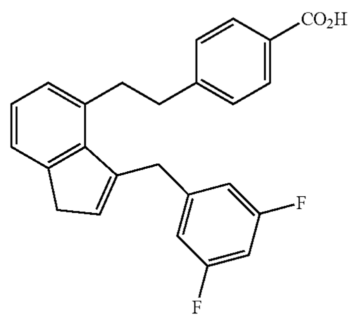 [SMILES: O=C(O)c1ccc(CCc2cccc3c2C(Cc2cc(F)cc(F)c2)=CC3)cc1] | 6 | 27 | 57 | 134 | |
| 19 | 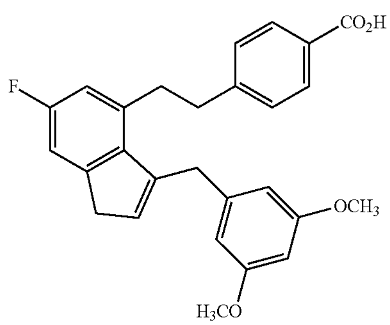 [SMILES: COc1cc(CC2=CCc3cc(F)cc(CCc4ccc(C(=O)O)cc4)c32)cc(OC)c1] | 36 | 18 | 2 | 0.4 | |
| 20 | 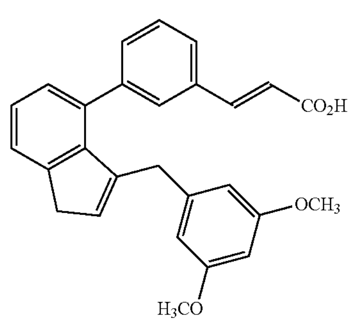 [SMILES: COc1cc(CC2=CCc3cccc(-c4cccc(/C=C/C(=O)O)c4)c32)cc(OC)c1] | | >10K | 1231 | | |

TABLE 2-continued

| Entry | STRUCTURE | cAMP EC50 (nM) | Ki (nM) | cAMP EC50 (nM) | Ki EC50 (nM) | FLIPR EC50 (nM) |
|---|---|---|---|---|---|---|
| 21 | 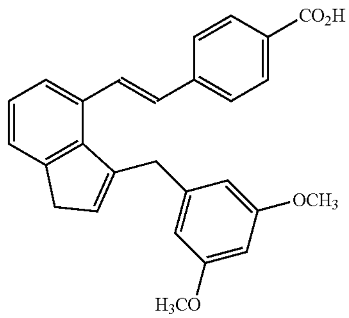 [SMILES: COc1cc(CC2=CCc3cccc(/C=C/c4ccc(C(=O)O)cc4)c32)cc(OC)c1] | 4772 | >10K | 1203 | | |
| 22 | 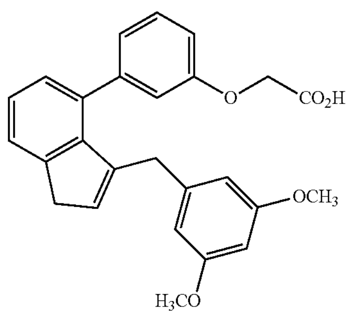 [SMILES: COc1cc(CC2=CCc3cccc(-c4cccc(OCC(=O)O)c4)c32)cc(OC)c1] | >10K | 1173 | | | |
| 23 | 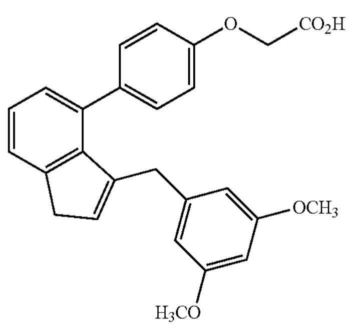 [SMILES: COc1cc(CC2=CCc3cccc(-c4ccc(OCC(=O)O)cc4)c32)cc(OC)c1] | >10K | >10K | 4467 | | |
| 24 | 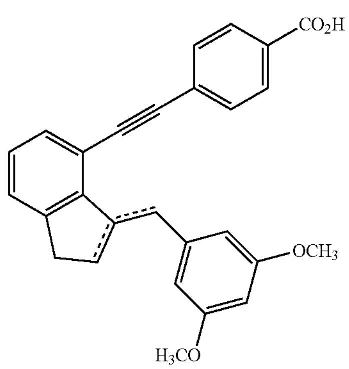 | >10K | >10K | 3603 | | |

While this invention has been described with respect to these specific examples, it is understood that other modifications and variations are possible without departing from the spirit of the invention.

What follows are non-limiting embodiments of the invention:

1. A compound of formula (I):

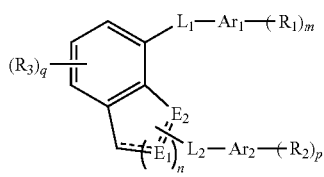

wherein:
- the dashed lines represents optional bonds, provided that only one optional bond to $E_1$ is present;
- $E_1$ and $E_2$ are each independently C or N;
- $L_1$ is a bond, $C_1$-$C_4$ alkylene, $C_2$-$C_4$ alkenylene, or $C_2$-$C_4$ alkynylene;
- $L_2$ is a bond, $C_1$-$C_4$ alkylene,

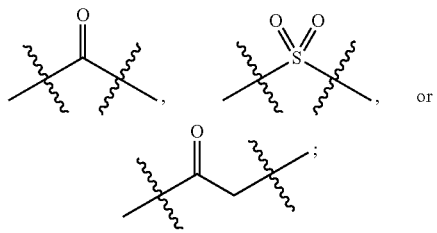

- $Ar_1$ and $Ar_2$ are each independently aryl or heteroaryl;
- $R_1$, $R_2$ and $R_3$ are each independently —$CO_2H$, halogen, —$CF_3$, alkoxy, benzyloxy, $C_1$-$C_4$ alkyl, —OH, —$OCH_2CO_2H$, —CH=$CHCO_2H$ or $NR_aR_b$, wherein $R_a$ and $R_b$ are each independently H or lower alkyl;
- n is 1 or 2;
- m and p are each independently 1 to 5; and
- q is 0 to 3.

2. The compound of embodiment 1 of formula (II):

(II)

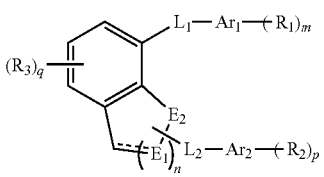

wherein:
- the dashed line represents an optional bond;
- $E_1$ and $E_2$ are each independently C or N;
- $L_1$ is $C_1$-$C_4$ alkylene, $C_2$-$C_4$ alkenylene, or $C_2$-$C_4$ alkynylene;
- $L_2$ is $C_0$-$C_4$ alkylene,

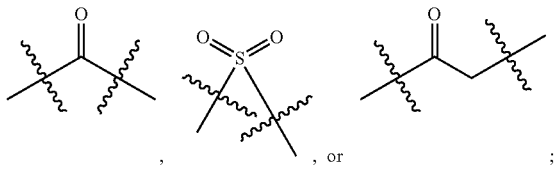

- $Ar_1$ and $Ar_2$ are each independently aryl or heteroaryl;
- $R_1$, $R_2$ and $R_3$ are each independently —$CO_2H$, halogen, —$CF_3$, alkoxy, benzyloxy, $C_1$-$C_4$ alkyl, —OH, or $NR_aR_b$, wherein $R_a$ and $R_b$ are each independently H or lower alkyl;
- n is 1 or 2;
- m and p are each independently 1 to 5; and
- q is 0 to 3.

3. The compound of embodiment 1 or 2 wherein $L_1$ is $C_2$ alkylene.

4. The compound of embodiment 1 or 2 wherein $L_2$ is $C_1$-$C_4$ alkylene.

5. The compound of embodiment 4 wherein $L_2$ is $C_1$ alkylene.

6. The compound of embodiment 1 or 2 wherein $Ar_1$ is aryl.

7. The compound of embodiment 6 wherein $Ar_1$ is phenyl or naphthyl.

8. The compound of embodiment 1 or 2 wherein $Ar_1$ is heteroaryl.

9. The compound of embodiment 8 wherein $Ar_1$ is furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl thiophenyl, furylene, pyridinylene, oxazolylene, or thiazolene.

10. The compound of embodiment 8, wherein $Ar_1$ is thiophenyl.

11. The compound of embodiment 1 or 2 wherein $Ar_2$ is aryl.

12. The compound of embodiment 10 wherein $Ar_2$ is phenyl or naphthyl.

13. The compound of embodiment 1 or 2 wherein $Ar_2$ is heteroaryl.

14. The compound of embodiment 13 wherein $Ar_2$ is benzo[d][1,3]dioxole, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl thiophenyl, furylene, pyridinylene, oxazolylene, or thiazolene.

15. The compound of embodiment 14 wherein $Ar_2$ is benzo[d][1,3]dioxole.

16. The compound of embodiment 1 or 2 wherein m and p are each independently 1 or 2.

17. The compound of embodiment 1 or 2 wherein $R_1$ is —$CO_2H$.

18. The compound of embodiment 1 or 2 wherein $R_2$ is halogen.

19. The compound of embodiment 18 wherein $R_2$ is F.

20. The compound of embodiment 1 or 2 wherein $R_2$ is alkoxy.
21. The compound of embodiment 20 wherein $R_2$ is methoxy.
22. The compound of embodiment 1 of formula (III):

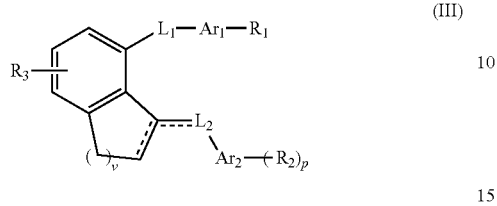

wherein:
  the dashed lines represent optional bonds, provided that only one optional bond is present;
  $L_1$ is a bond, $C_1$-$C_2$ alkylene, $C_2$ alkenylene, $C_2$ alkynylene, or —$OCH_2$—;
  $L_2$ is $CH_2$;
  $Ar_1$ and $Ar_2$ are each phenyl;
  $R_1$ is —$CO_2H$, —$OCH_2CO_2H$ or —CH=CHCO$_2$H;
  each $R_2$ is independently halogen, —$CF_3$, $C_1$-$C_4$ alkyl, or $C_1$-$C_4$ alkoxy;
  $R_3$ is H, halogen, or $C_1$-$C_4$ alkoxy; and
  p and v are each independently 1 or 2.

23. The compound of embodiment 22 wherein $L_1$ is $C_2$ alkylene, $R_1$ is —$CO_2H$, each $R_2$ is halogen, methyl or methoxy, and $R_3$ is H.
24. The compound of embodiment 22 wherein $L_1$ is $C_2$ alkylene, $R_1$ is —$CO_2H$, each $R_2$ is halogen, methyl or methoxy, $R_3$ is H, and v is 1.
25. The compound of embodiment 22 wherein $L_1$ is $C_2$ alkylene, $R_1$ is —$CO_2H$, each $R_2$ is halogen, methyl or methoxy, $R_3$ is H, p is 2, and v is 1.
26. The compound of embodiment 22 wherein $L_1$ is $C_2$ alkylene, $R_1$ is —$CO_2H$, each $R_2$ is methoxy, $R_3$ is H, and v is 1.
27. The compound of embodiment 1 or 2 having any one of the following structures:

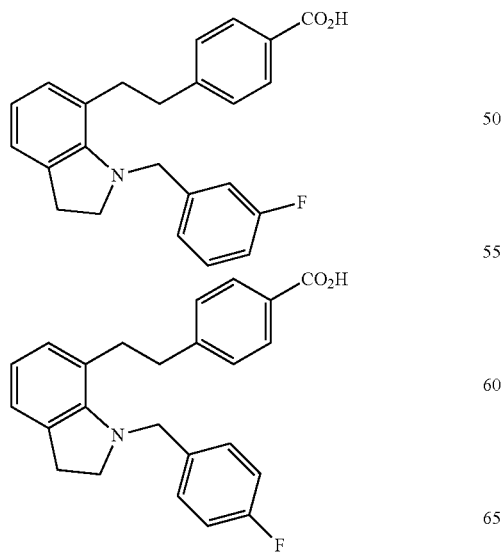

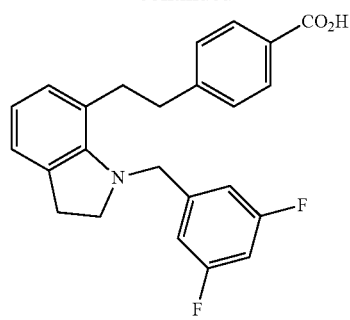

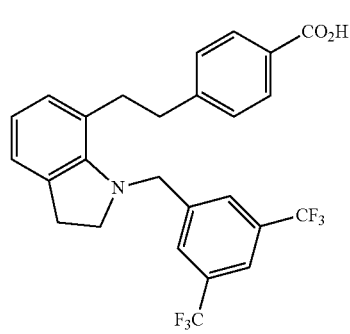

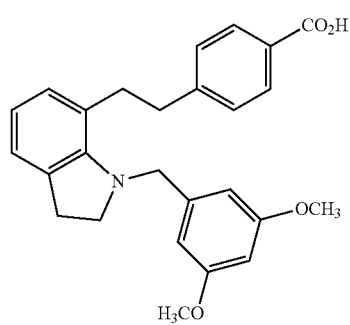

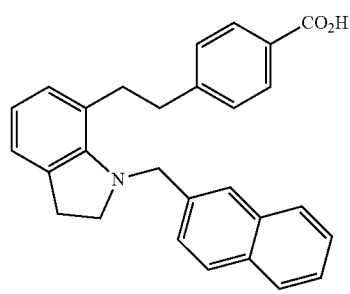

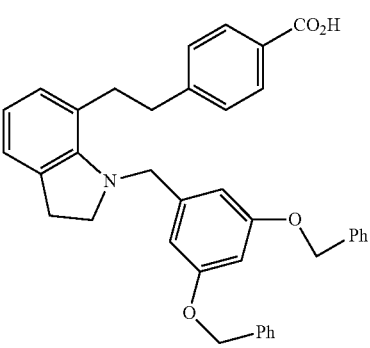

77
-continued

78
-continued

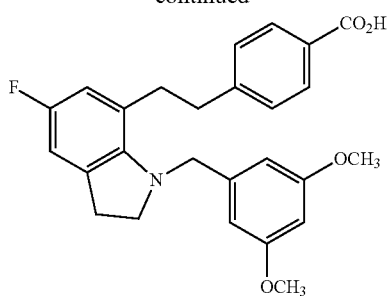
28. The compound of embodiment 1 or 2 having any one of the following structures:
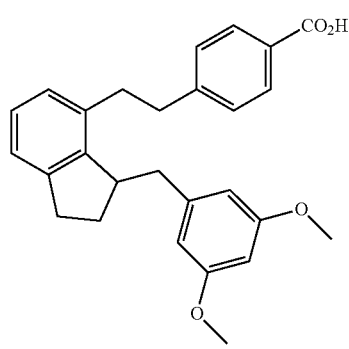
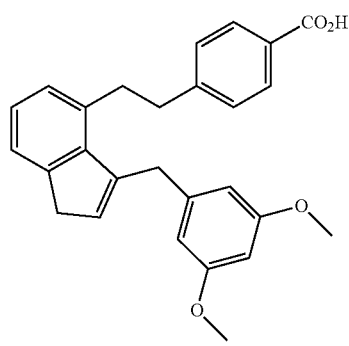
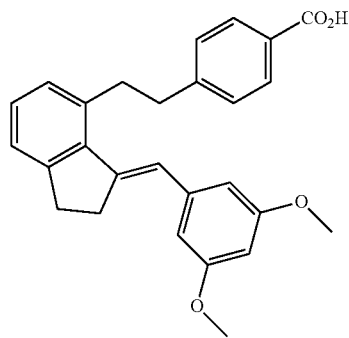
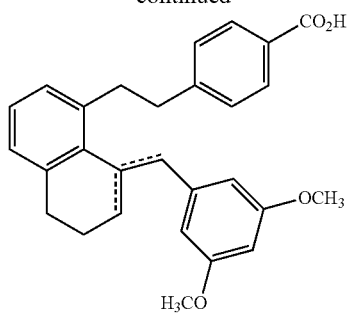
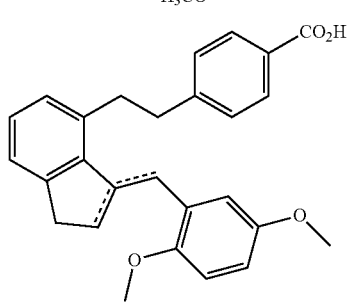
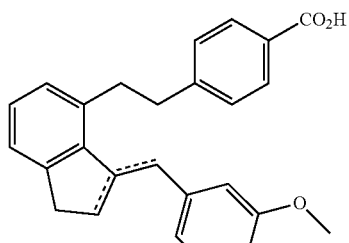
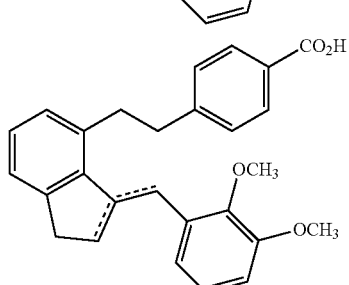
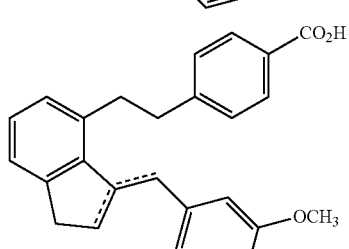
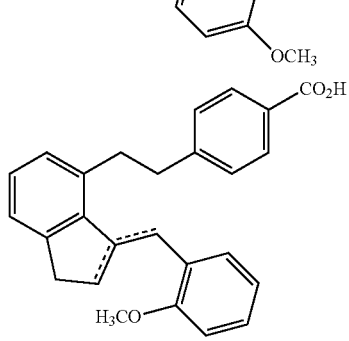

81
-continued
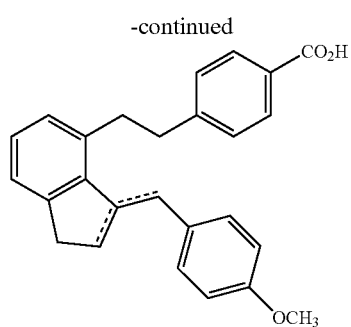
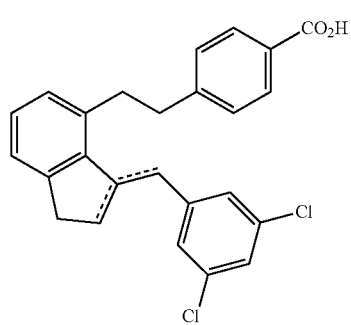
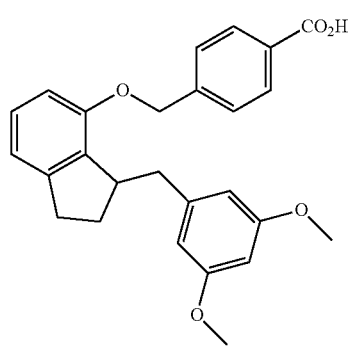
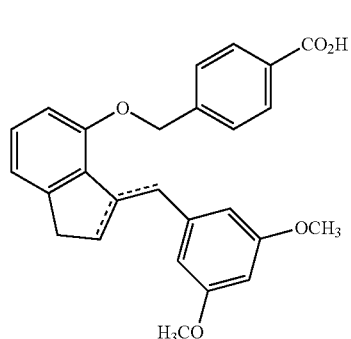
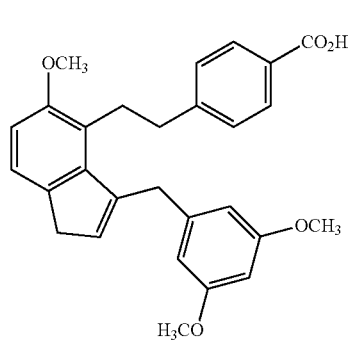
82
-continued
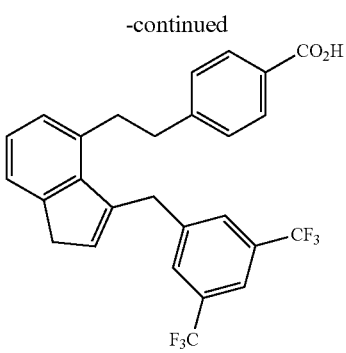
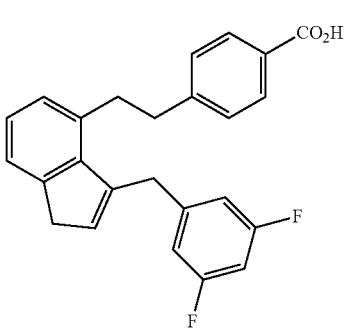
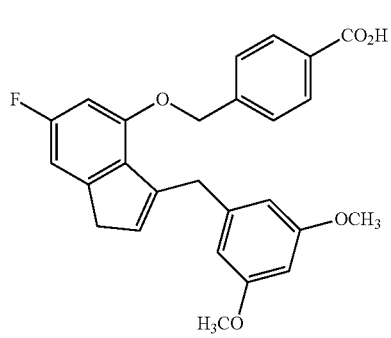
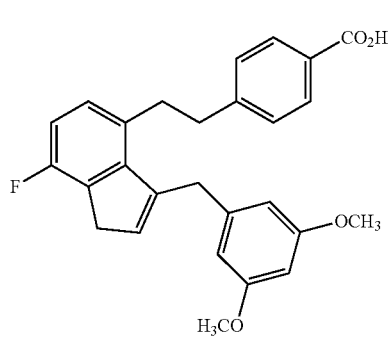
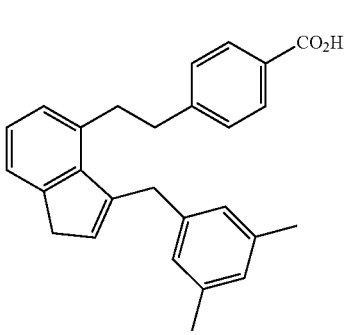

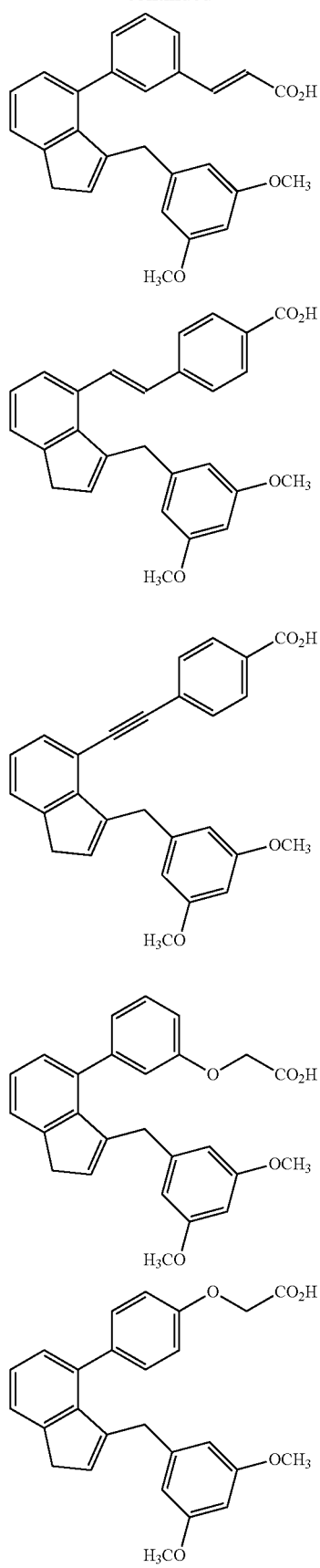
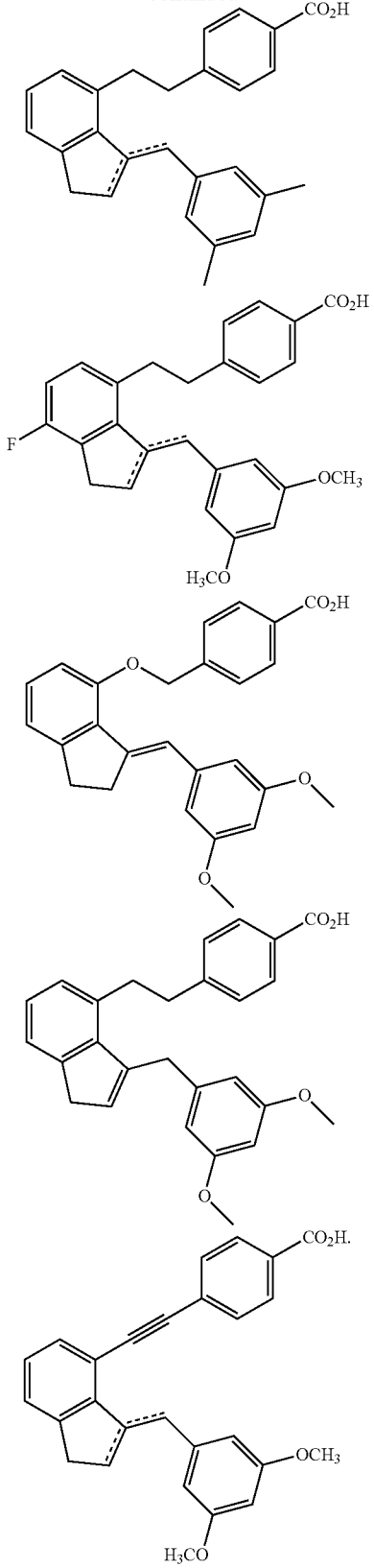
29. A pharmaceutical composition comprising at least one compound of any one of embodiments 1-28 and a pharmaceutical acceptable carrier therefor.

30. A method of treating a skin blemish comprising administering to a subject in need thereof a composition comprising a therapeutically effective amount of a compound of any one of embodiments 1-28.
31. The method of embodiment 30, wherein the administration reduces formation of a scar type selected from the group consisting of hypertrophic scar, recessed scar, stretch mark, and a combination thereof
32. The method of embodiment 30, wherein the skin blemish is a wrinkle
33. The method of embodiment 30, wherein the composition is administered to a region selected from the group consisting of a face, neck, arms, torso, back, legs, and a combination thereof.
34. The method of embodiment 30, wherein the composition is administered at a time selected from the group consisting of prior to surgical incision, during surgery, postoperatively, and a combination thereof.
35. The method of embodiment 30, wherein said administration minimizes scar formation.
36. The method of embodiment 30, wherein said administration prevents scar formation.
37. The method of embodiment 30, wherein said administration prevents wrinkle formation.
38. The method of embodiment 30, wherein said administration reduces the appearance of an existing wrinkle.
39. A compound of embodiment 1 or 2 having the any one of the following structures:

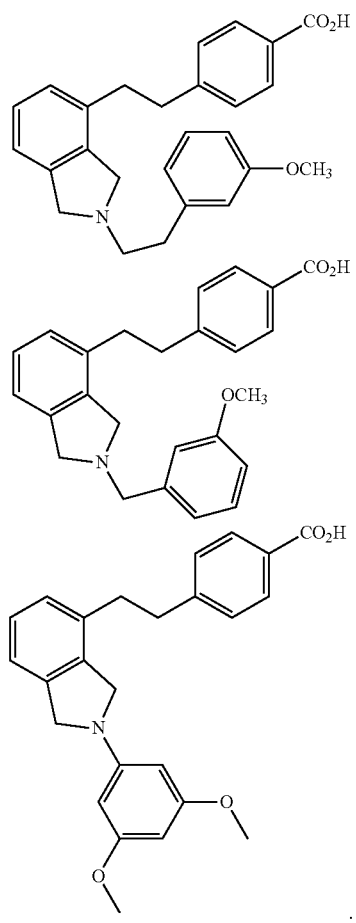

40. A compound of embodiment 1 or 2 having the any one of the following structures:

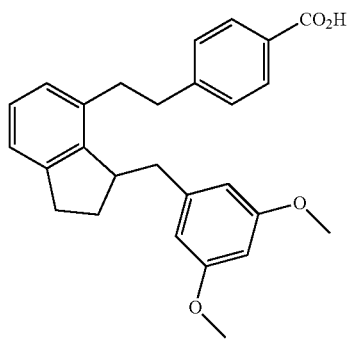

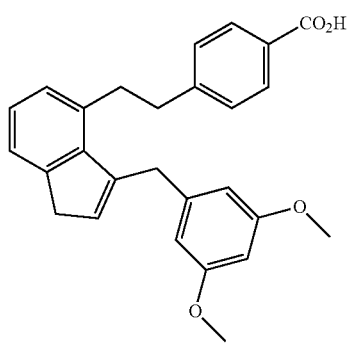

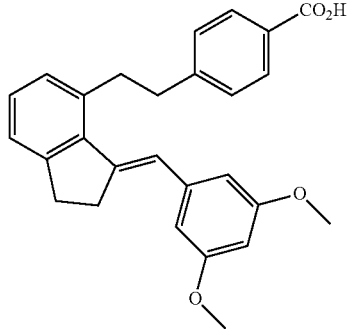

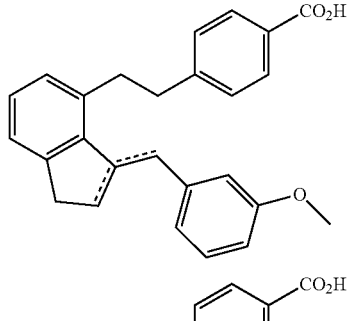

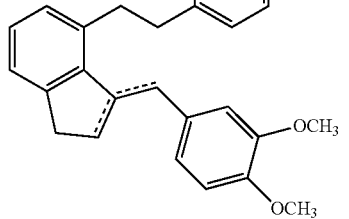

87
-continued
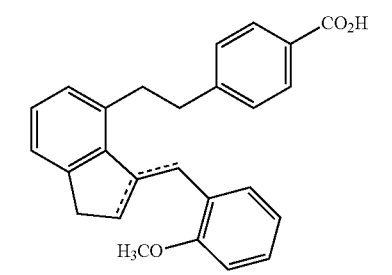
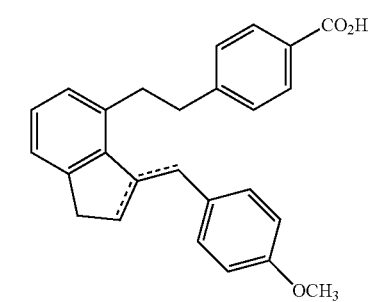
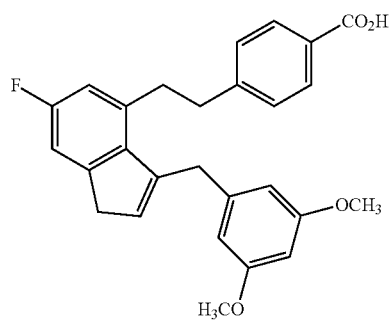
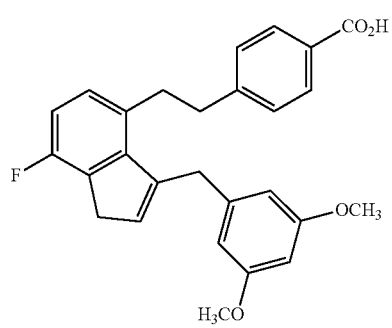
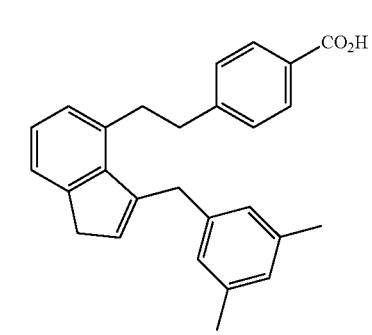
88
-continued
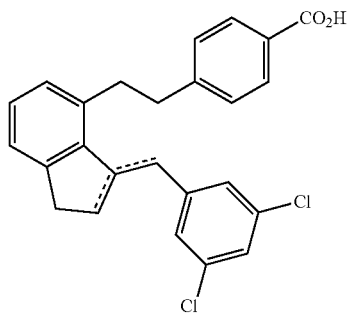
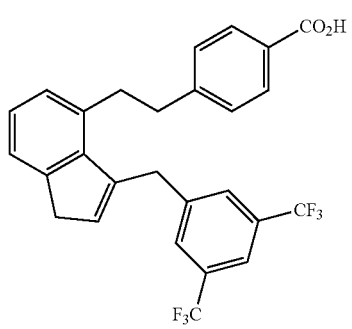
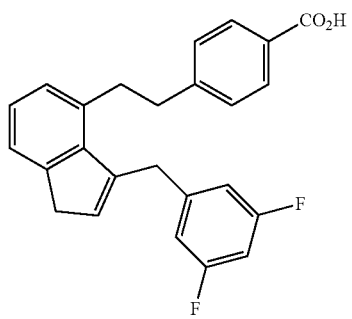
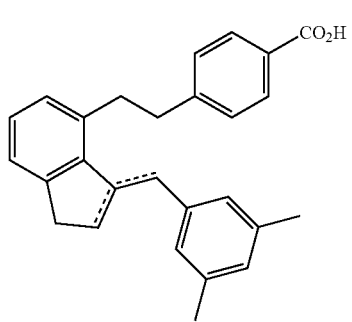
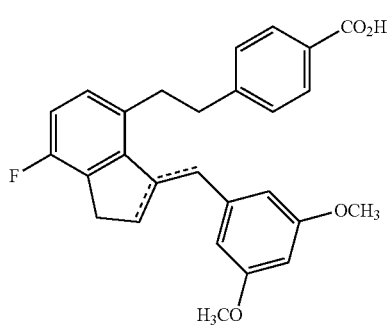

-continued

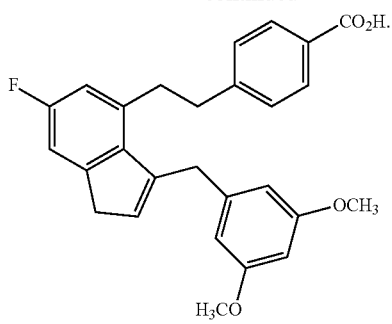

What is claimed is:

1. A compound of formula (I):

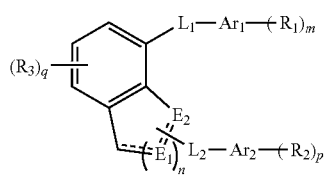

wherein:

the dashed lines represents optional bonds, provided that only one optional bond to $E_I$ is present;

$E_I$ and $E_2$ are each independently C or N;

$L_1$ is $C_2$ alkylene, $C_2$ alkenylene, or $C_2$ alkynylene;

$L_2$ is $C_1$-$C_2$ alkylene,

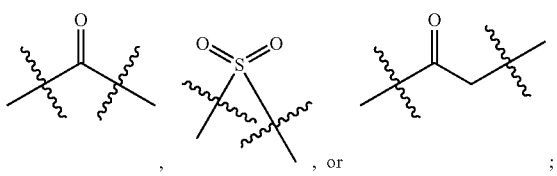

$Ar_1$ and $Ar_2$ are each independently phenyl, naphthyl, thiophenyl, or benzoro[d][1,3]dioxolyl;

$R_1$, $R_2$ and $R_3$ are each independently —$CO_2H$, halogen, —$CF_3$, alkoxy, benzlyoxy, $C_1$-$C_4$ alkyl, or —$OCH_2CO_2H$;

n is 1 or 2;

m and p are each independently 1 or 2; and q is 0 or 1.

2. The compound of claim 1, wherein $L_1$ is $C_2$ alkylene.
3. The compound of claim 1, wherein $L_2$ is $C_2$ alkylene.
4. The compound of claim 3, wherein $L_2$ is $C_1$ alkylene.
5. The compound of claim 1, wherein $R_1$ is —$CO_2H$.
6. The compound of claim 1, wherein $R_2$ is halogen.
7. The compound of claim 6, wherein $R_2$ is F.
8. The compound of claim 1, wherein $R_2$ is alkoxy.
9. The compound of claim 8, wherein $R_2$ is methoxy.

10. The compound of claim 1 of formula (III):

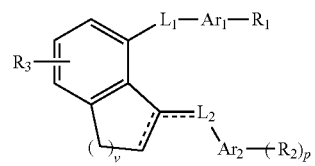

wherein:

the dashed lines represent optional bonds, provided that only one optional bond is present;

$L_1$ is $C_2$ alkylene, $C_2$ alkenylene, $C_2$ alkynylene, or —$OCH_2$—;

$L_2$ is $CH_2$;

$Ar_1$ and $Ar_2$ are each phenyl;

$R_1$ is —$CO_2H$ or —$OCH_2CO_2H$;

each $R_2$ is independently halogen, —$CF_3$, $C_1$-$C_4$ alkyl, or $C_1$-$C_4$ alkoxy;

$R_3$ is H, halogen, or $C_1$-$C_4$ alkoxy; and p and v are each independently 1 or 2.

11. The compound of claim 10, wherein $L_1$ is $C_2$ alkylene, $R_1$ is —$CO_2H$, each $R_2$ is halogen, methyl or methoxy, and $R_3$ is H.

12. The compound of claim 10, wherein $L_1$ is $C_2$ alkylene, $R_1$ is —$CO_2H$, each $R_2$ is halogen, methyl or methoxy, $R_3$ is H, and v is 1.

13. The compound of claim 10, wherein $L_1$ is $C_2$ alkylene, $R_1$ is —$CO_2H$, each $R_2$ is halogen, methyl or methoxy, $R_3$ is H, p is 2, and v is 1.

14. The compound of claim 10, wherein $L_1$ is $C_2$ alkylene, $R_1$ is —$CO_2H$, each $R_2$ is methoxy, $R_3$ is H, and v is 1.

15. A pharmaceutical composition comprising at least one compound of claim 1 and a pharmaceutical acceptable carrier therefor.

16. The compound of claim 1, wherein the compound is selected from the group consisting of

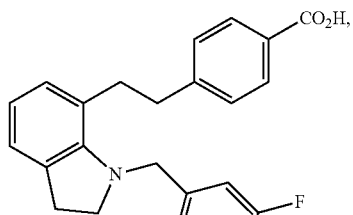

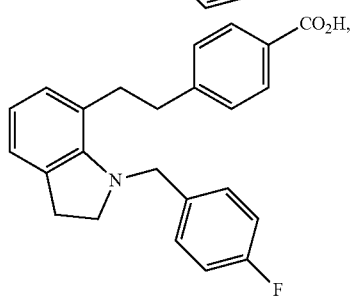

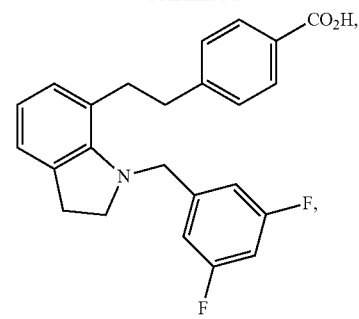
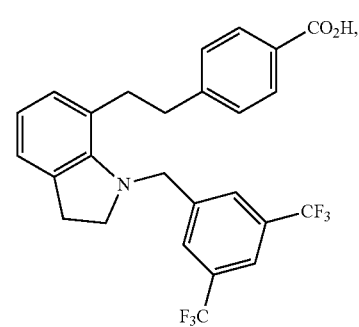
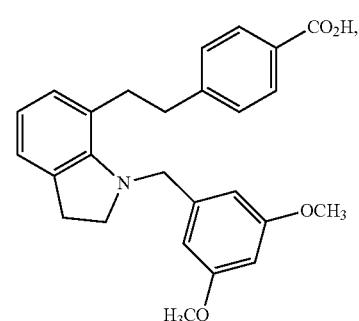
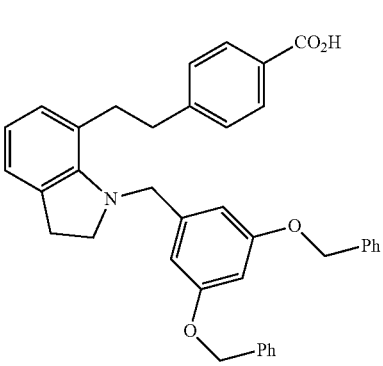
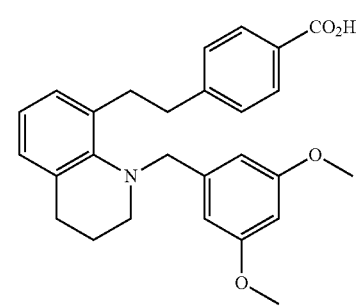
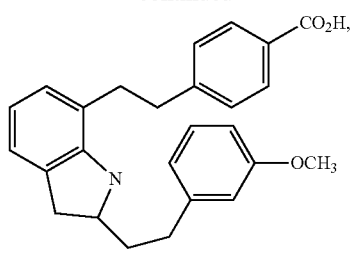
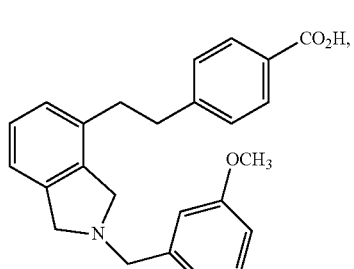
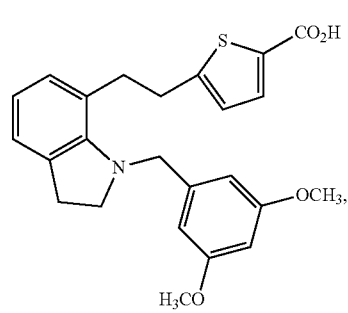
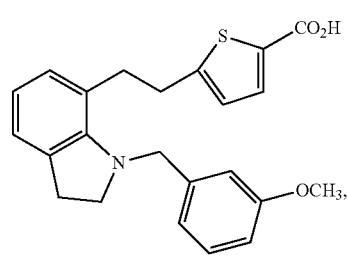
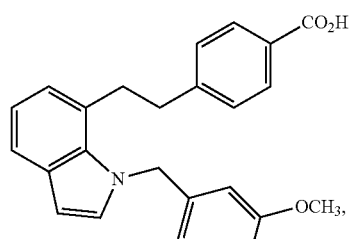
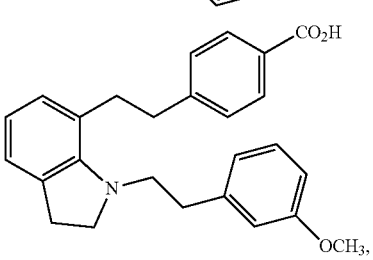

-continued
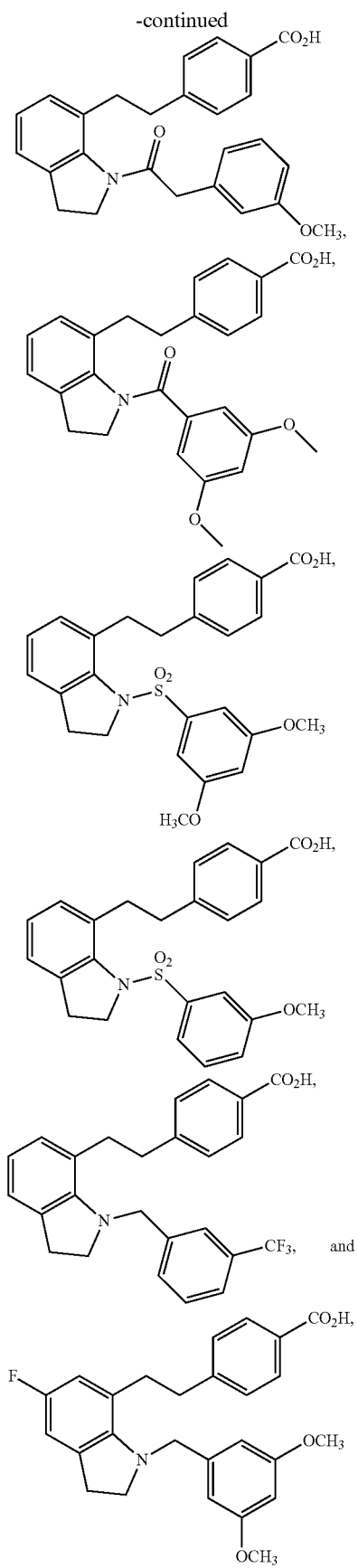
17. The compound of claim 10, wherein the compound is selected from the group consisting of
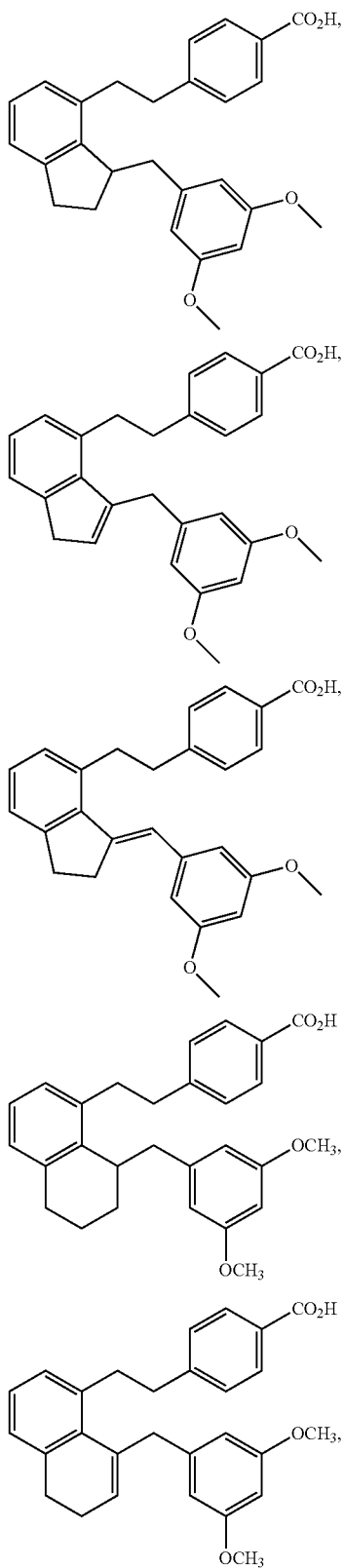

95
-continued
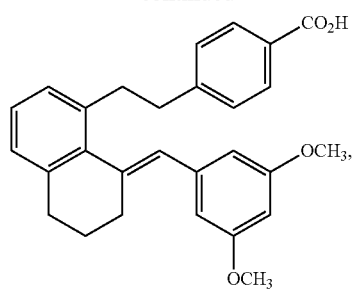
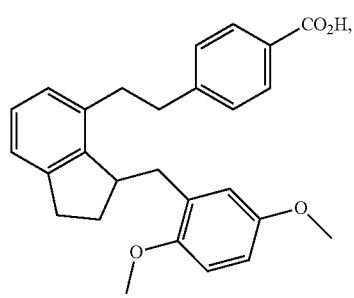
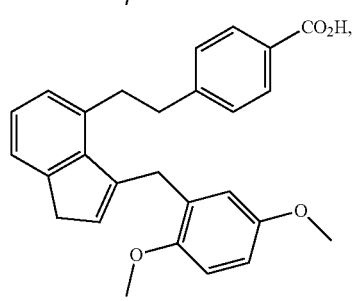
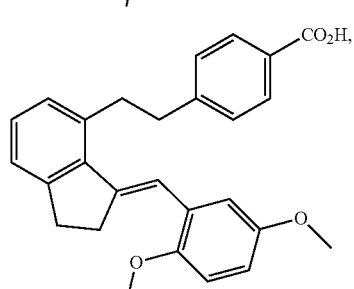
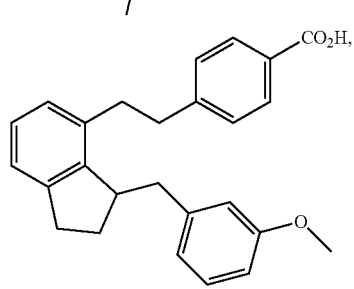
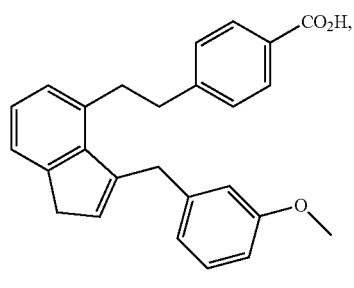
96
-continued
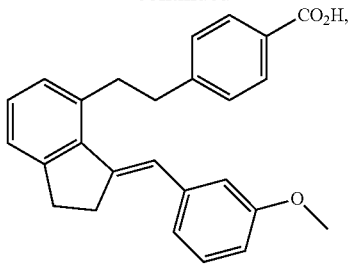
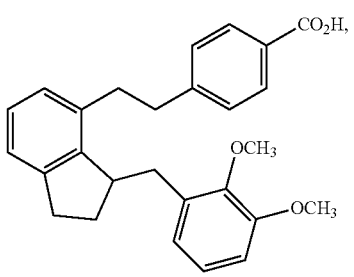
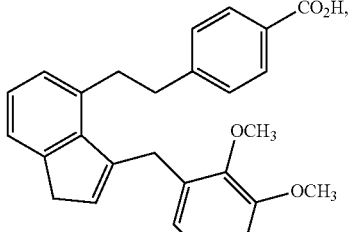
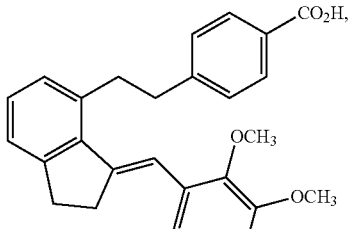
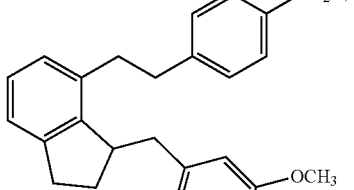
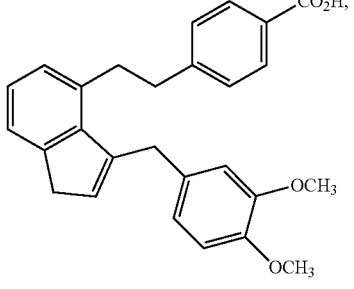

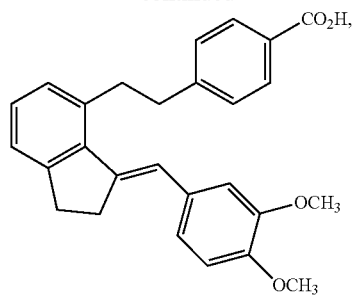
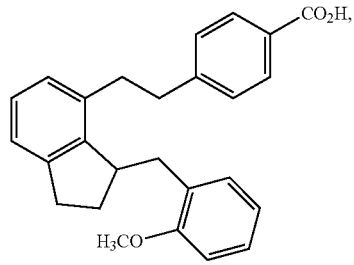
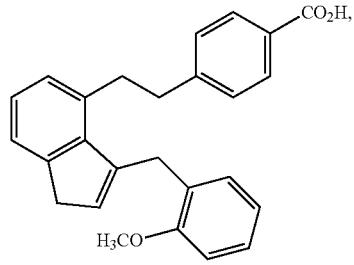
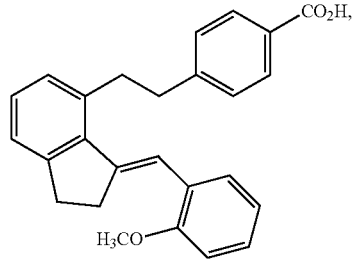
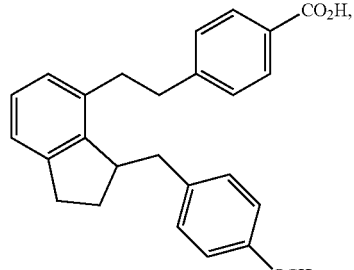
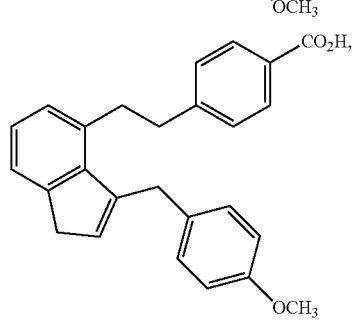
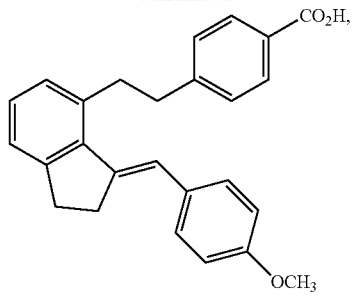
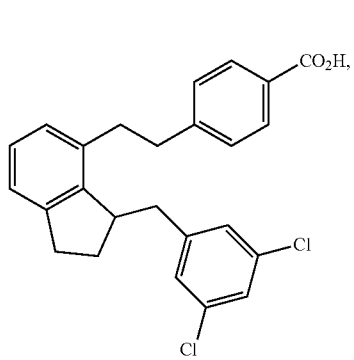
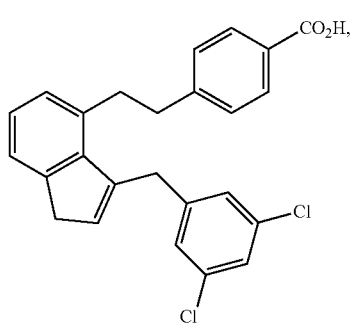
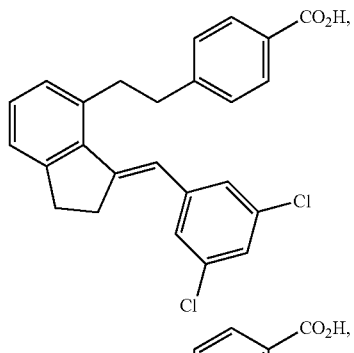
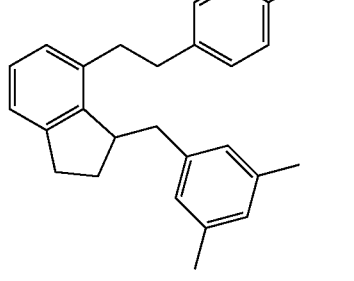

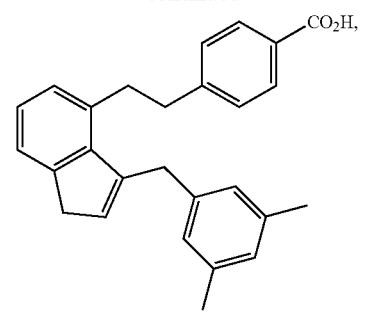
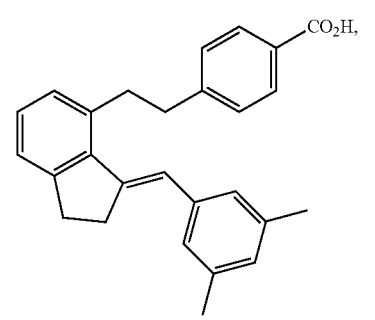
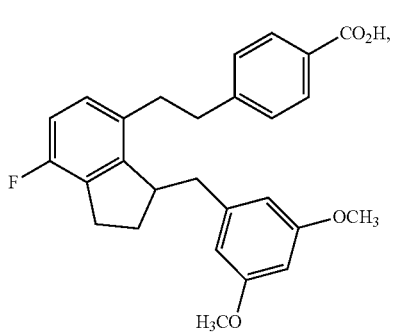
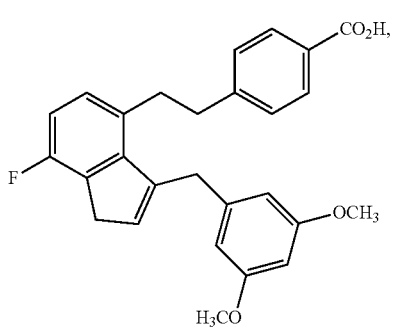
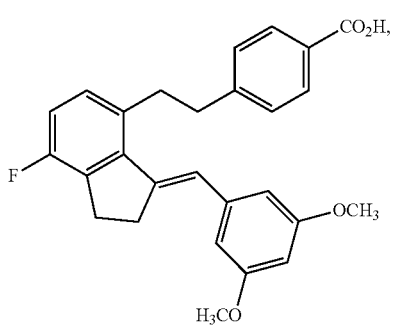
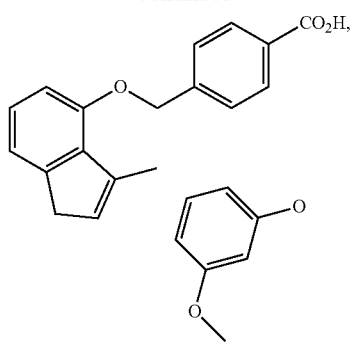
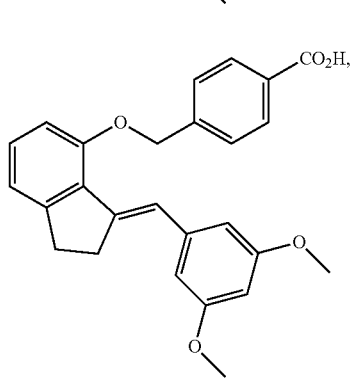
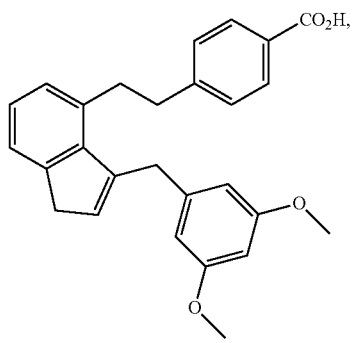
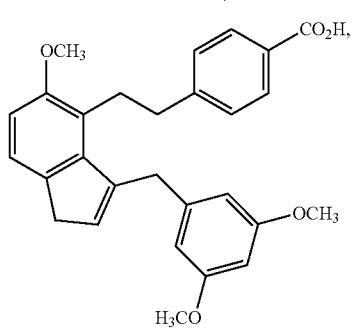
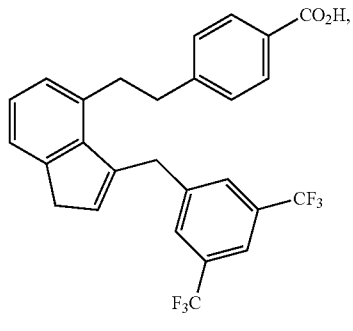

-continued

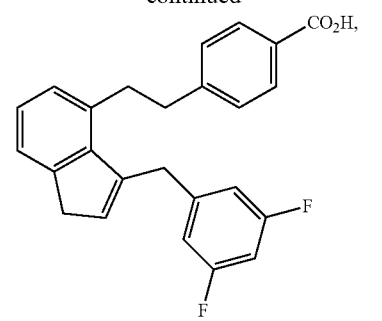

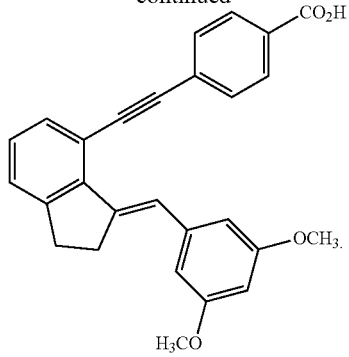

18. A method of minimizing the formation of a scar comprising administering to a subject in need thereof a composition comprising a therapeutically effective amount of a compound of claim 1.

19. The method of claim 18, wherein the scar is of a type selected from the group consisting of hypertrophic scars, recessed scars, and stretch marks, or a combination thereof.

20. The method of claim 18, wherein the composition is administered to a region selected from the group consisting of a face, neck, arms, torso, back, and legs, or a combination thereof.

21. The method of claim 18, wherein the composition is administered at a time selected from the group consisting of prior to surgical incision, during surgery, and post-operatively, or a combination thereof.

22. A method of reducing the appearance of an existing wrinkle comprising administering to a subject in need thereof a composition comprising a therapeutically effective amount of a compound of claim 1.

23. The method of claim 22, wherein the composition is administered to a region selected from the group consisting of a face, neck, arms, torso, back, and legs, or a combination thereof.

24. A compound selected from the group consisting of

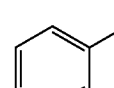

103
-continued

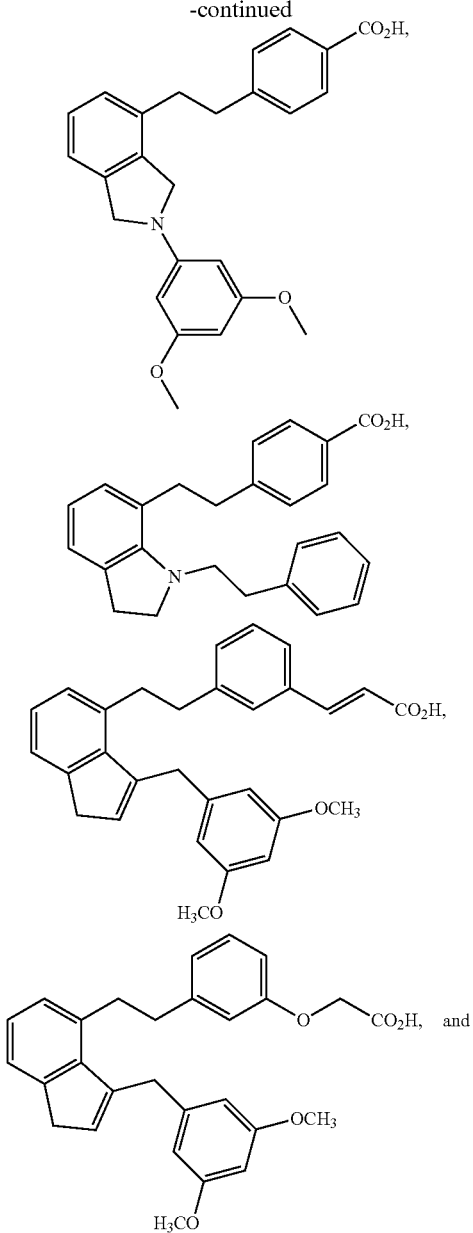

104
-continued

25. A method of minimizing the formation of a scar comprising administering to a subject in need thereof a composition comprising a therapeutically effective amount of a compound of claim 24.

26. The method of claim 25, wherein the scar is of a type selected from the group consisting of hypertrophic scars, recessed scars, and stretch marks, or a combination thereof.

27. The method of claim 25, wherein the composition is administered to a region selected from the group consisting of a face, neck, arms, torso, back, and legs, or a combination thereof.

28. The method of claim 25, wherein the composition is administered at a time selected from the group consisting of prior to surgical incision, during surgery, and post-operatively, or a combination thereof.

29. A method of reducing the appearance of an existing wrinkle comprising administering to a subject in need thereof a composition comprising a therapeutically effective amount of a compound of claim 24.

30. The method of claim 29, wherein the composition is administered to a region selected from the group consisting of a face, neck, arms, torso, back, and legs, or a combination thereof.

31. A pharmaceutical composition comprising at least one compound of claim 24 and a pharmaceutical acceptable carrier therefor.

* * * * *

UNITED STATES PATENT AND TRADEMARK OFFICE
CERTIFICATE OF CORRECTION

PATENT NO. : 9,546,162 B2
APPLICATION NO. : 14/498380
DATED : January 17, 2017
INVENTOR(S) : Yariv Donde et al.

Page 1 of 2

It is certified that error appears in the above-identified patent and that said Letters Patent is hereby corrected as shown below:

On the Title Page

In item (57), in Column 2, in "Abstract", Line 4, delete "and or" and insert -- and/or --, therefor.

In the Specification

In Column 1, Line 42, delete "others" and insert -- others. --, therefor.

In Column 1, Line 62, delete "and or" and insert -- and/or --, therefor.

In Column 3, Line 33, delete "meaning" and insert -- meaning. --, therefor.

In Column 6, Line 1, before "pyrazolyl," delete "pyrazinyl,".

In Column 6, Line 3, delete "thiadiazolyl" and insert -- thiadiazolyl, --, therefor.

In Column 6, Line 16, before "pyrazolyl," delete "pyrazinyl,".

In Column 6, Line 18, delete "thiadiazolyl" and insert -- thiadiazolyl, --, therefor.

In Column 9, Lines 1-11, delete " 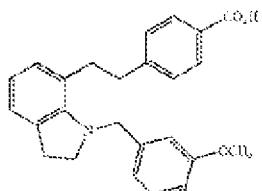 " and insert -- 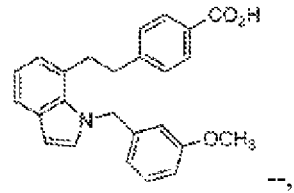 --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)

In Column 24, Line 40, delete "DMf" and insert -- DMF --, therefor.

In Column 33, Line 49, delete "antiypyrin," and insert -- antipyrine, --, therefor.

In Column 33, Line 54, delete "chrondroitin" and insert -- chondroitin --, therefor.

In Column 33, Line 55, delete "Inamarin," and insert -- linamarin, --, therefor.

In Column 47, Line 11, delete "2H)" and insert -- 2H). --, therefor.

In Column 47, Line 30, delete "44243-" and insert -- 4-(2-(3- --, therefor.

In Columns 63-64, Line 6 (TABLE 2-continued), delete "FP." and insert -- FP, --, therefor.

In Column 74, Line 35, after "pyrrolyl," delete "pyrazinyl,".

In Column 74, Line 38, delete "thiadiazolyl" and insert -- thiadiazolyl, --, therefor.

In Column 74, Line 54, after "pyrrolyl," delete "pyrazinyl,".

In Column 74, Lines 56-57, delete "thiadiazolyl" and insert -- thiadiazolyl, --, therefor.

In Column 77, Lines 45-56, delete " " and insert -- --, therefor.

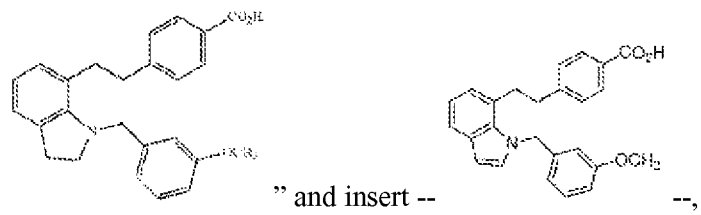

In Column 85, Line 8, delete "thereof" and insert -- thereof. --, therefor.

In Column 85, Line 10, delete "wrinkle" and insert -- wrinkle. --, therefor.

In the Claims

In Column 89, Line 32, in Claim 1, delete "E$_l$" and insert -- $E_1$ --, therefor.

In Column 89, Line 33, in Claim 1, delete "E$_l$" and insert -- $E_1$ --, therefor.

In Column 89, Line 36, in Claim 1, after "alkylene," insert --  --.

In Column 90, Line 22, in Claim 10, delete "C$_l$-C$_4$" and insert -- $C_1$-$C_4$ --, therefor.